United States Patent [19]

Naito et al.

[11] Patent Number: 4,642,365
[45] Date of Patent: Feb. 10, 1987

[54] METHOD FOR PRODUCTION OF 1,3,2-DIOXAPHOSPHOLES

[75] Inventors: Kenzo Naito, Soraku; Masayasu Kato, Ashiya; Kazuo Tsukamura, Kawabe, all of Japan

[73] Assignee: Takeda Chemical Industries, Ltd., Osaka, Japan

[21] Appl. No.: 795,743

[22] Filed: Nov. 7, 1985

Related U.S. Application Data

[60] Continuation of Ser. No. 631,801, Jul. 17, 1985, abandoned, which is a division of Ser. No. 415,318, Sep. 17, 1982, abandoned.

[30] Foreign Application Priority Data

Sep. 10, 1981 [JP] Japan ............................. 56-143302
Jan. 18, 1982 [JP] Japan ............................. 57-6668

[51] Int. Cl.[4] .............................................. C07F 9/21
[52] U.S. Cl. .............................................. 558/83; 558/86
[58] Field of Search .................. 260/973; 558/86, 83

[56] References Cited

U.S. PATENT DOCUMENTS 2,791,574  5/1957  Lanham ............................ 260/937
2,883,411  4/1959  Lanham ............................ 260/937
3,294,872  12/1966 Allcock ............................ 260/973
3,686,367  8/1972  Cowling ........................... 260/936
3,773,711  11/1973 Dever et al. .

OTHER PUBLICATIONS

Anschutz et al., "Chemical Abstracts", vol. 26, (1932) 2437.
Kosolapoff et al., "Organic Phosphorus Compounds", vol. 6, (1973), pp. 265-266.
Berlin et al., Condensation of Catechol with Phenylphosphonous Dischloride, A Novel Ring-Cleavage Reaction, J. Org. Chem. 29(5), p. 2056, 1964.

Primary Examiner—Anton H. Sutto
Attorney, Agent, or Firm—Wegner & Bretschneider

[57] ABSTRACT

A method is provided for producing a 1,3,2-dioxaphosphole of the formula

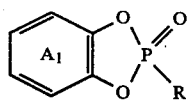

wherein

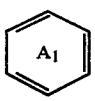

respresents a benzene ring which may be substituted and R represents an aryl, alkoxy or aralkyloxy group which may be substituted, which comprises reacting a catechol compound of the formula

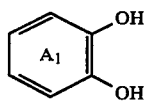

wherein

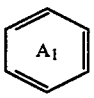

is an defined above, with a compound of the formula

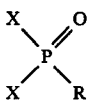

wherein X is a halogen atom and R is as defined above, at a temperature not higher than about 30° C. in the presence of a base.

10 Claims, No Drawings

METHOD FOR PRODUCTION OF 1,3,2-DIOXAPHOSPHOLES

This application is a continuation of Ser. No. 631,801, filed July 17, 1985, which is a division of Ser. No. 415,318, filed Sept. 17, 1982, both now abandoned.

This invention relates to a novel method of producing of cephalosporin compound of the formula

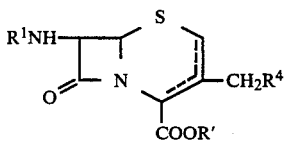

[I]

wherein $R^1$ is a hydrogen atom or an acyl group; R' is a hydrogen atom or an ester residue; the dotted line means a double bond in 2- or 3-position of the cephem ring; and $R^4$ is a nucleophilic compound residue, or a salt thereof, directly in one step from a compound of the formula

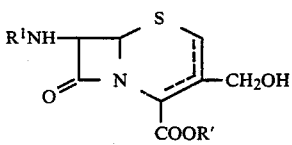

[II]

wherein $R^1$, R' and the dotted line have the same meanings as defined above, or a salt thereof, being useful in an industrial production.

The cephalosporin compound [I] is not only a valuable antimicrobial compound but also is an important intermediate compound for the production of such cephalosporin compounds. There are known a variety of processes for the production of the compounds [I], but yet not known a satisfactory process for preparing the compounds [I] directly from the compounds [II] as the starting material.

Among the known processes for the production of the compounds [I], are (i) the processes wherein a cephem compound having an acyloxymethyl group in 3-position of the cephem ring and a thiol compound are (1) reacted in water or a mixture of water with an organic solvent under acidic to weakly alkaline conditions (Japanese Published Examined Patent Application Nos. 17936/1964 and 13023/1971, U.S. Pat. No. 3,641,021, B.P. Nos. 1283811 and 1321412, and OLS No. 2262477, etc.), (2) heated in an organic solvent (Japanese Published Unexamined Patent Application No. 43043/1980, etc.), (3) reacted in the presence of an acid or an acid complex (OLS No. 2804896, B.P. Nos. 1565941, 2027429 and 2048257, Japanese Published Unexamined Patent Application Nos. 20724/1980, 49383/1980 and 153790/1980, etc.), (ii) the process in which the acetoxy group in the 3-acetoxymethyl group of the cephem nucleus is substituted with a nucleophilic reagent [A. B. Taylor: Journal of the Chemical Society, p. 7020 (1965)], (iii) the process in which the hydroxy group in the 3-hydroxymethyl group of the cephem ring is converted into a halogen and the latter is then substituted with a nucleophilic compound [A. B. Bywood et al, Recent Advances in the Chemistry of β-Lactam Antibiotics, 139, 1977], (iv) the process in which the 3-hydroxymethyl group of the cephem nucleus is acylated to an acyloxymethyl group followed by substitution with a nucleophilic reagent [Tsushima et al: Chemical and Pharmaceutical Bulletin 27, 696 (1979)] and so forth. However, in the processes (i) (1) and (2), the quality and yield of the product compound are low due to hydrolysis of the β-lactam ring under the reaction conditions, for instance. In the process (i) (3), side reactions such as lactonization and fission of the β-lactam ring are liable to take place. Moreover, when a Lewis acid or a complex thereof is used as said acid, the reaction equipment is subject to limitations and post-treatments are complicated. Furthermore, after the reaction, the acid must be separated by neutralization with an alkali which is liable to cause decomposition and coloration of the product. The yield of the product compound [I] is also very poor depending on the types of starting material and acid. If lactonization, decomposition of the β-lactam ring or coloration takes place, the corresponding impurities derived therefrom tend to find their way into the product [I] and removal of such impurities would be troublesome and cause a decrease of yield. Moreover, in the process (i) (3), the starting material must be low in moisture content in order to avoid infiltration of moisture but this requires a drying step and the dry power tends to be scattered to affect the working environment. For example, since 7-aminocephalosporanic acid has the property to cause contact dermatitis in humans [Kirk-Othmar, Encyclopedia of Chemical Technology, The Third Edition, 1978, Volume 2, p. 907–908], the process is disadvantageous from industrial points of view. In the process (ii) which involves severe reaction conditions, the starting material and product compound are liable to be decomposed. In the process (iii), in order that lactonization may be avoided, the 4-carboxy group must be esterified or otherwise protected, and the esterified or protected compounds are easily subject to isomerization of the double bond in the cephem ring. In the process (iv), the reaction conditions may be somewhat mild as compared with the process (ii) but are not sufficiently mild. Further, excepting the case in which a special acylating agent is employed, it is generally necessary to carry out an acylation reaction and a substitution reaction in distinct phases, thus detracting from the yield and quality of the final compound. Thus, the process is time-consuming, requires additional equipment and is, therefore, not satisfactory for industrial purposes.

After a thorough exploration of possible processes for the production of cephalosporin compounds [I], using as the starting material compounds of the formula [II] including deacetyl-cephalosporin C (DCPC) and a compound which is obtainable by chemical or enzymatic treatment of DCPC or cephalosporin C, the present inventors found surprisingly that it is possible to react in an organic solvent a compound [II] or a salt thereof, a nucleophilic compound or a salt thereof and (1) a trivalent or pentavalent cyclic phosphorus compound having a partial structure of formula [III]

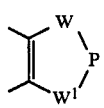

[III]

wherein W is an oxygen atom, a sulfur atom or $NR^2$; $W^1$ is an oxygen atom, a sulfur atom or $NR^3$; $R^2$ and $R^3$ are the same or different and each is a hydrogen atom or a hydrocarbon group, or a salt thereof, or (2) a reaction product of a compound of formula [IV]

 [IV]

wherein W and W¹ have the same meanings as defined above, or a salt thereof, with a phosphorus oxyhalide, phosphorus trihalide or phosphorus pentahalide, that the reaction proceeds under very mild conditions (i.e., in a short time, at low temperature, atmospheric pressure, etc.) to give the cephalosporin compound [I] in good yield, that the subject compound [I] obtained from the anhydrous reaction system can be used without complex drying steps required, when the compound [I] is subjected to an acylation or deacylation reaction under anhydrous conditions in the subsequent step, and that therefore the reaction is useful in a method for preparing the compound [I] directly in one step from the compound [II] in an industrial production. The above finding and subsequent study led to the perfection of this invention. So, this invention can provide the compounds [I] in a lower cost.

In the above formulas, $R^1$ is a hydrogen atom or an acyl group. The acyl group represented by $R^1$ includes, among others, those acyl groups which are the substituents on the amino group at the 6-position in so far known penicillin derivatives or at the 7-position in cephalosporin derivatives. Such acyl groups may be represented, for example, by the formula

 [V]

wherein $R^5$ is a hydrogen atom or an alkyl, phenyl* or heterocyclic* group, or by the formula

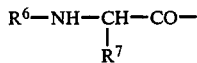 [VI]

wherein $R^6$ is a hydrogen atom, an amino acid residue, an amino-protecting group or a group of the formula $R^8-(CH_2)_{n_1}-CO-$ (in which $R^8$ is a heterocyclic* group and $n_1$ is an integer of 0–2) and $R^7$ is an alkyl, phenyl* or heterocyclic group, or by the formula

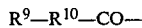 [VII]

wherein $R^9$ is a group of the formula

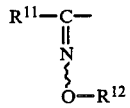

in which $R^{11}$ is an alkyl*, heterocyclic* or phenyl* group and $R^{12}$ is a hydrogen atom or a group of the formula $-R^{13}-R^{14}$ ($R^{13}$ being an alkylene or alkenylene* group and $R^{14}$ being a phenyl*, carboxyl, esterified carboxyl or mono- or dialkylamino), and $R^{10}$ is a bond of the formula $-CO-NH-CH(R^{15})-$ ($R^{15}$ being an alkyl, phenyl* or thiazolyl* group, or by the formula

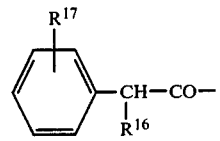 [VIII]

wherein $R^{16}$ is a hydroxy, hydroxysulfonyloxy, carboxy, ureido*, sulfamoyl*, sulfo, phenoxy*carbonyl or formyloxy and $R^{17}$ is hydrogen, alkyl, alkoxy, halogen, nitro or hydroxy, or by the formula

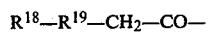 [IX]

wherein $R^{18}$ is a cyano, phenyl*, phenoxy*, alkyl*, acyloxy, alkenyl* or heterocyclic* group and $R^{19}$ is a bond or $-S-$.

When the above-mentioned groups represented by symbols $R^5$ to $R^{19}$ are "groups which may optionally be substituted", the names of such groups herein shall be designated by a superscript asterisk. Thus, for example, "an alkyl which may optionally be substituted" shall be denoted as "alkyl*". In such case, the number of substituents is not limited to one but the relevant substituted group may have two to several substituents which may be the same or different. The alkyl is preferably a straight or branched lower alkyl containing 1–6 carbon atoms, such as methyl, ethyl, n-propyl, isopropyl, n-butyl, isobutyl, sec-butyl, tert-butyl, n-pentyl, isopentyl, n-hexyl or isohexyl. The alkenyl is preferably a straight or branched lower alkenyl containing 2–6 carbon atoms, such as vinyl, allyl, isopropenyl, 2-methallyl, 2-butenyl or 3-butenyl. The heterocyclic group includes, among others, groups derived from 5- to 8-membered rings containing one to several hetero atoms such as nitrogen (which may be in the form of N-oxide), oxygen and/or sulfur atom or atoms or fused ring corresponding thereto, such as 2- or 3-pyrrolyl, 2- or 3-furyl, 2- or 3-thienyl, 2- or 3-pyrrolidinyl, 2-, 3- or 4-pyridyl, N-oxido-2-, 3- or 4-pyridyl, 2-, 3- or 4-piperidinyl, 2-, 3- or 4-pyranyl, 2-, 3- or 4-thiopyranyl, pyrazinyl, 2-, 4- or 5-thiazolyl, 2-, 4- or 5-oxazolyl, 3-, 4- or 5-isothiazolyl, 3-, 4- or 5-isoxazolyl, 2-, 4- or 5-imidazolyl, 3-, 4- or 5-pyrazolyl, 3- or 4-pyridazinyl, N-oxido-3- or 4-pyridazinyl, 2-, 4- or 5-pyrimidinyl, N-oxido-2-, 4- or 5-pyrimidinyl, piperazinyl, 4- or 5-(1,2,3-thiadiazolyl), 3- or 5-(1,2,4-thiadiazolyl), 1,3,4-thiadiazolyl, 1,2,5-thiadiazolyl, 4- or 5-(1,2,3-oxadiazolyl), 3- or 5-(1,2,4-oxadiazolyl), 1,3,4-oxadiazolyl, 1,2,5-oxadiazolyl, 1,2,3- or 1,2,4-triazolyl, 1H or 2H-tetrazolyl, pyrido[2,3-d]pyrimidyl, benzopyranyl, 1,8-, 1,5-, 1,6-, 1,7-, 2,7- or 2,6-nphthyridyl, quinoyl and thieno[2,3-b]pyridyl, which are frequently used. The alkoxy is preferably a straight or branched lower alkoxy containing 1–6 carbon atoms, such as methoxy, ethoxy, n-propoxy, isopropoxy, n-butoxy, isobutoxy, sec-butoxy, tert-butoxy, n-pentyloxy, isopentyloxy, n-hexyloxy or isohexyloxy. The halogen includes fluorine, chlorine, bromine and iodine. The amino acid residue includes glycyl, alanyl, valyl, leucyl, isoleucyl, seryl, threonyl, cysteyl, cystyl, methionyl, α- or β-aspartyl, α- or γ-glutamyl, lysyl, arginyl, phenylalanyl, phenylglycyl, tyrosyl, histidyl, tryptophanyl, prolyl and so on. The alkylene is preferably a lower alkylene containing 1–6 carbon atoms, such as methylene, ethylene, propylene or isopropylene. The alkenylene is preferably a straight or branched lower alkenylene containing 2–4 carbon atoms, such as vinylene or propenylene. The ester-forming group for the carboxyl group is, for example, a lower alkyl group containing 1-6 carbon atoms such as methyl, ethyl, propyl, n-butyl, isobutyl or tert-butyl. The amino-protecting group may be any of the conventional ones used for the same purpose in the fields of beta-lactam chemistry and peptide syntheses and thus includes aromatic acyl groups, such as phthaloyl, toluoyl, naphthoyl, benzoyl, chlorobenzoyl, p-nitrobenzoyl, p-tert-butylbenzoyl, p-tert-butylbenzenesulfonyl, benzenesulfonyl, toluenesulfonyl and phenylacetyl, aliphatic acyl groups, such as formyl, acetyl, propionyl, valeryl, caprylyl, n-decanoyl, acryloyl, pivaloyl, monochloroacetyl, dichloroacetyl, trichloroacetyl, methanesulfonyl, ethanesulfonyl, camphorsulfonyl, trifluoroacetyl, maleyl and succinyl, esterified carboyl groups, such as methoxycarbonyl, ethoxycarbonyl, tert-butyoxycarbonyl, isopropoxycarbonyl, 2-cyanoethoxycarbonyl, $\beta,\beta,\beta$-trichloroethoxycarbonyl, $\beta$-trimethylsilylethoxycarbonyl, $\beta$-methylsulfonylethoxycarbonyl, benzyloxycarbonyl, p-nitrobenzyloxycarbonyl, p-methoxybenzyloxycarbonyl, diphenylmethyloxycarbonyl, methoxymethyloxycarbonyl, acetylmethyloxycarbonyl, isobornyloxycarbonyl and phenyloxycarbonyl, substituted carbamoyl groups, such as methylcarbamoyl, phenylcarbamoyl and naphthylcarbamoyl, further trityl, 2-nitrophenylthio, benzylidene, 4-nitrobenzylidene, trialkylsilyl, benzyl, p-nitrobenzyl, phosphoryl groups, such as diethylphosphoryl, dimethylphosphoryl, diphenylphosphoryl, diisopropylphosphoryl, diisobutylphophoryl, dibutylphosphoryl, o-hydroxyphenylphosphoryl and methyl(o-hydroxyphenyl)phosphoryl, phosphinyl groups, scuh as dimethylphosphinyl and diphenylphosphinyl, phosphonyl groups, such as phenylphosphonyl and butylphosphonyl, and like amino-protecting groups other than acyl groups. The selection of the amino-protecting group is not critical in practicing the invention. The acyl moiety of the acyloxy group is as mentioned below in $R^{20}$ to $R^{22}$.

Among these, the alkyl and alkenyl may be substituted by one to three substituents, for example, cycloalkyl*, cycloalkenyl*, aryl*, heterocyclic group*, alkoxycarbonyl, acyl, oxo, halogen, cyano, trifluoromethyl, hydroxy, alkoxy, aryl*oxy, acyloxy, carbamoyloxy, hydroxysulfonyloxy, alkylsulfonyloxy, aryl*sulfonyloxy, nitro, amino, carboxy, aminocarbonyl, alkylthiocarbonyl, mercapto, alkylthio, aminoalkylthio, acylaminoalkylthio, aralkyl*thio, aryl*thio, heterocycle*thio and/or quaternary ammonium*. The substituted alkyl group may be the one represented, for example, by the formula

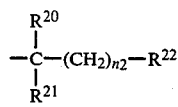
[X]

wherein $n_2$ is an integer of 0 to 3, $R^{20}$ and $R^{21}$ are the same or different and each is hydrogen atom, alkyl, cycloalkyl*, aralkyl*, aryl*, heterocyclic* group, alkoxycarbonyl or acyl, or $R^{20}$ and $R^{21}$ combinedly represent oxo, and $R^{22}$ is hydrogen atom, alkyl, cycloalkyl*, aryl*, heterocyclic* group, halogen, cyano, hydroxy, alkoxy, aryl*oxy, acyloxy, carbamoyloxy, hydroxysulfonyloxy, alkylsulfonyloxy, aryl*sulfonyloxy, nitro, amino, carboxy, alkoxycarbonyl, aminocarbonyl, alkylthiocarbonyl, acyl, mercapto, alkylthio, aminoalkylthio, acylaminoalkylthio, aralkyl*thio, aryl*thio, heterocycle*thio or quaternary ammonium*. Referring to $R^{20}$, $R^{21}$ and $R^{22}$, the cycloalkyl preferably contains 3-8 carbon atoms and is, for example, cyclopropyl, cyclobutyl, cyclopentyl, cyclohexyl, cycloheptyl or adamantyl. The aryl is, for example, phenyl, $\alpha$-naphthyl, $\beta$-naphthyl, biphenyl or anthryl; in particular, phenyl, naphthyl and the like are frequently used. The aralkyl includes benzyl, phenethyl, phenylpropyl and naphthylmethyl. The acyl group includes formyl, alkylcarbonyl, aryl*carbonyl, aralkyl*carbonyl, heterocycle*carbonyl, heterocycle*acetyl, etc. Preferred among others are acetyl, propionyl, n-butyryl, isobutyryl, n-pentanoyl, n-hexanoyl, benzoyl, 4-hydroxybenzoyl, 4-methoxybenzoyl, phenylacetyl, 4-hydroxyphenylacetyl, 4-methoxyphenylacetyl, 2-thienylcarbonyl, 2-furylcarbonyl, 2-, 4- or 5-thiazolylacetyl, 2- or 3-thienylacetyl, 2- or 3-furylacetyl, 2-amino-4- or 5-thiazolylacetyl, etc. The quaternary ammonium group is, for example, pyridinium or quinolinium. The cycloalkenyl group includes, for example, those having 3 to 8 carbon atoms such as 1-cyclopropenyl, 1-cyclohexenyl, 1-cycloheptenyl, etc.

The substituents on the cycloalkyl, cycloalkenyl, aralkyl, aryl, heterocyclic and quaternary ammonium groups include alkyl, alkoxy, alkenyl, aryl, aralkyl, mercapto, alkylthio, arylthio, aralkylthio, alkylsulfonyl, arylsulfonyl, aralkylsulfonyl, trihaloalkyl, hydroxy, oxo, thioxo, halogen, nitro, amino, cyano, carbamoyl, carboxy, acyl, acyloxy, acylamino, hydroxyalkyl, carboxyalkyl, haloalkyl, mono- or dialkylaminoalkyl, etc., wherein said alkyl, alkoxy, alkenyl, aryl, aralkyl and acyl are as above mentioned.

The phenoxy* may have the same substituents as mentioned above for the aryl*. Furthermore, the thiazoyl* may be substituted by an acylamino group containing 2-4 carbon atoms which in turn is substituted by alkyl, alkoxy, halogen, hydroxy, amino, etc. The heterocyclic* group may be substituted by a phenyl group substituted by alkyl, alkoxy, halogen, nitro, amino etc. The substituent on the ureido* is, for example, sulfo in the form of an adequate salt with sodium, potassium, etc., carbamoyl, sulfamoyl, amindino, $C_{1-3}$ alkyl, etc. The substituent on the sulfamoyl* is, for example, $C_{1-3}$ lower alkyl or amidino, The substituent on the alkenylene* is, for example, carboxy or cyano.

The formula

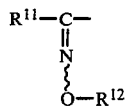

in $R^9$ represents the syn isomer having the formula

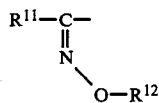

as well as the anti isomer having the formula

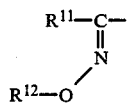

or a mixture of these.

Referring to the above acyl group, a typical one of the acyl group represented by the formula [V] is a group of the formula $$R^{5a}-CO- \quad [V]^a$$

wherein $R^{5a}$ is a hydrogen atom, $C_{1-6}$ alkyl, phenyl which may be substituted with nitro or 5- or 6-membered heterocyclic group containing O, S and/or N as a hetero atom or atoms which may be substituted with a $C_{1-6}$ alkyl, oxo, phenyl or halogenophenyl group; a typical one of the acyl group represented by the formula [VI] is a group of the formula $$R^{6a}-NH-\underset{R^{7a}}{CH}-CO- \quad [VI]^a$$

wherein $R^{6a}$ is a hydrogen atom or a group of the formula $R^{8a}-(CH_2)_{n_1}-CO-$ (wherein $R^{8a}$ is a 5- or 6-membered heterocyclic group containing O, S and/or N as a hetero atom or atoms or fused ring corresponding thereto which may be substituted with a $C_{1-6}$ alkyl, oxo, hydroxyl, carboxyl, formyl, halogen or $C_{1-6}$ alkylsulfonyl and $n_1$ is as defined above) and $R^{7a}$ is phenyl which may be substituted with hydroxyl, alkoxyl or benzyloxy, or thienyl group; a typycal one of the acyl group represented by the formula [VII] is a group of the formula $$R^{9a}-R^{10a}-CO- \quad [VII]^a$$

wherein $R^{9a}$ is a group of the formula

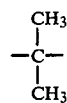

wherein $R^{11a}$ is a 5-membered heterocyclic group containing O, S and/or N as a hetero atom or atoms which may be substituted with amino group, or phenyl, and $R^{12a}$ is a hydrogen atom or a group of the formula $-R^{13a}-R^{14a}$ (wherein $R^{13a}$ is $-CH_2-$ or $$-\underset{\underset{CH_3}{|}}{\overset{\overset{CH_3}{|}}{C}}-$$

and $R^{14a}$ is carboxyl), and $R^{10a}$ is a bond; a typical one of the acyl group represented by the formula [VIII] is a group of the formula

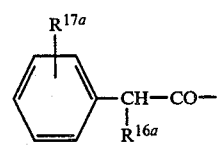

wherein $R^{16a}$ is hydroxyl, carboxyl or sulfo, and $R^{17a}$ is hydrogen or hydroxyl; a typical one of the acyl group represented by the formula [IX] is a group of the formula $$R^{18a}-R^{19a}-CH_2-CO- \quad [IX]^a$$

wherein $R^{18a}$ is cyano, phenoxy, cyano-$C_{1-6}$ alkyl or 5-membered heterocyclic group containing O, S and/or N as a hetero atom or atoms which may be substituted with amino, and $R^{19}$ is a bond.

Further, frequently used one of the above acyl group is a group of the formula $$R^a-R^b-CO- \quad [A]$$

wherein $R^a$ is an aryl, 5-membered heterocyclic group containing nitrogen and/or sulfur atom which may be substituted with amino group or a group of the formula

wherein $R^c$ is amino which may be protected and $R^d$ is carboxyl which may be protected and $R^b$ is a $C_{1-6}$ alkylene group or a group of the formula

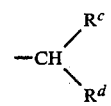

wherein $R^e$ is a $C_{1-6}$ alkyl group which may be substituted with carboxyl group; and more frequently used one thereof is a group of the formula $$R^f-R^g-CO- \quad [B]$$

wherein $R^f$ is phenyl, thienyl, thiazolyl substituted with amino, or a group of the formula

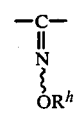

wherein $R^c$ and $R^d$ have the same meanings as defined above, and $R^g$ is a $C_{1-6}$ alkylene group or a group of the formula

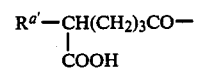

wherein $R^h$ is a $C_{1-6}$ alkyl group.

A preferable one of the acyl group represented by $R^1$ is a group of the formula:

$$R^{a'}-\underset{\underset{COOH}{|}}{CH}(CH_2)_3CO-$$

wherein $R^{a'}$ is an amino group protected, for example, with an aromatic acyl or esterified carboxyl group.

Referring to the above acyl group, examples of the acyl group represented by the formula $R^5-CO-$ are formyl, acetyl, hexanoyl, benzoyl, p-nitrobenzoyl, 3-(2,6-dichlorophenyl)-5-methylisoxazol-4-yl-carbonyl, 5-methyl-3-phenyl-4-isoxazolylcarbonyl and 4-ethyl-2,3-dioxo-1-piperazinocarbonyl.

Examples of the acyl group represented by the formula

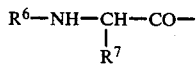

are D-alanyl, benzyl N$^\alpha$-carbobenzoxy-γ-D-glutamyl-D-alanyl, D-phenylglycyl-D-alanyl, N-carbobenzoxy-D-alanyl, N-carbobenzoxy-D-phenylglycyl, D-alanyl-D-phenylglycyl, γ-D-glutamyl-D-alanyl, 2-(4-ethyl-2,3-dioxo-1-piperazinocarboxamido)-2-phenylacetyl, 2-(4-ethyl-2,3-dioxo-1-piperazinocarboxamido)-2-(4-sulfoxyphenyl)acetyl, N-(4-ethyl-2,3-dioxo-1-piperazinocarbonyl)-D-alanyl, N-(4-ethyl-2,3-dithioxo-1-piperazinocarbonyl)-D-phenylglycyl, 2,2-bis-(4-ethyl-2,3-dioxo-1-piperazinocarboxamido)acetyl, 2-(2-amino-4-thiazolyl)-2-(4-ethyl-2,3-dioxo-1-piperazinocarboxamido)acetyl, 2-(4-hydroxy-6-methylnicotinamido)-2-phenylacetyl, 2-(4-hydroxy-6-methylnicotinamido)-2-(4-hydroxyphenyl)acetyl, 2-[5,8-dihydro-2-(4-formyl-1-piperazinyl)-5-oxopyrido[2,3-d]pyrimidine-6-carboxamido]-2-phenylacetyl, 2-(3,5-dioxo-1,2,4-triazine-6-carboxamido)-2-(4-hydroxyphenyl)acetyl, 2-(3-furfurylideneamino-2-oxoimidazolidine-1-carboxamido)-2-phenylacetyl, 2-(coumarin-3-carboxamido)-2-phenylacetyl, 2-(4-hydroxy-7-methyl-1,8-naphthyridine-3-carboxamido)-2-phenylacetyl, 2-(4-hydroxy-7-trifluoromethylquinoline-3-carboxamido)-2-phenylacetyl, N-[2-(2-amino-4-thiazolyl)acetyl]-D-phenylglycyl, 2-(6-bromo-1-ethyl-1,4-dihydro-4-oxothieno[2,3-b]pyridine-3-carboxamido)-2-phenylacetyl, 2-(4-ethyl-2,3-dioxo-1-piperazinocarboxamido)-2-thienylacetyl, 2-(4-n-pentyl-2,3-dioxo-1-piperazinocarboxamido)-2-thienylacetyl, 2-(4-n-octyl-2,3-dioxo-1-piperazinocarboxamido)-2-thienylacetyl, 2-(4-cyclohexyl-2,3-dioxo-1-piperazinocarboxamido)-2-thienylacetyl, 2-[4-(2-phenylethyl)-2,3-dioxo-1-piperazinocarboxamido]-2-thienylacetyl, 2-(3-methylsulfonyl-2-oxoimidazolidine-1-carboxamido)-2-phenylacetyl, 2-(3-furfurylideneamino-2-oxoimidazolidine-1-carboxamido)-2-(4-hydroxyphenyl)acetyl, 2-(4-ethyl-2,3-dioxo-1-piperazinocarboxamido)-2-(4-benzyloxyphenyl)acetyl, 2-(4-ethyl-2,3-dioxo-1-piperazinocarboxamido)-2-(4-methoxyphenyl)acetyl, and 2-(8-hydroxy-1,5-naphthyridine-7-carboxamido)-2-phenylacetyl.

Examples of the acyl group represented by the formula R$^9$—R$^{10}$—CO— are N-[2-(2-amino-4-thiazolyl)-2-methoxyiminoacetyl]-D-alanyl, N-[2-(2-amino-4-thiazolyl)-2-methoxyiminoacetyl]-D-phenylglycyl, 2-(2-amino-4-thiazolyl)-2-[2-(2-amino-4-thiazolyl)-2-methoxyiminoacetamido]acetyl, 2-(2-chloroacetamido-4-thiazolyl)-2-methoxyiminoacetyl, 2-(2-amino-4-thiazolyl)-2-methoxyiminoacetyl, 2-(2-amino-4-thiazolyl)-2-ethoxyiminoacetyl, 2-(2-amino-4-thiazolyl)-2-propoxyiminoacetyl, 2-(2-amino-4-thiazolyl)-2-butoxyiminoacetyl, 2-(2-amino-4-thiazolyl)-2benzyloxyiminoacetyl, 2-(2-amino-4-thiazolyl)-2-allyloxyiminoacetyl, 2-(2-amino-5-chloro-4-thiazolyl)-2-methoxyiminoacetyl, 2-(2-amino-5-bromo-4-thiazolyl)-2-methoxyiminoacetyl, 2-(2-amino-4-thiazolyl)-2-oxyiminoacetyl, 2-(2-amino-4-thiazolyl)-2-[(1-methyl-1-carboxyethyl)oxyimino]acetyl, 2-(2-amino-4-thiazolyl)-2-carboxymethyloxyiminoacetyl, 2-thienyl-2-methoxyiminoacetyl, 2-furyl-2-methoxyiminoacetyl, 2-(1,2,4-thiadiazol-3-yl)-2-methoxyiminoacetyl, 2-(1,2,4-thiazol-5-yl)-2-methoxyiminoacetyl, 2-(1,3,4-thiadiazolyl)-2-methoxyiminoacetyl, 2-(4-hydroxyphenyl)-2-methoxyiminoacetyl, 2-phenyl-2-methoxyiminoacetyl, 2-phenyl-2-oxyiminoacetyl, 2-[4-(γ-D-glutamyloxy)phenyl]-2-oxyiminoacetyl, and 2-[4-(3-amino-3-carboxypropoxy)phenyl]-2-oxyiminoacetyl.

Examples of the acyl group represented by the formula

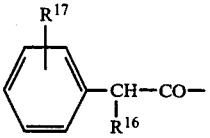

are α-sulfophenylacetyl, α-carboxyphenylacetyl, α-hydroxyphenylacetyl, α-ureidophenylacetyl, α-sulfoureidophenylacetyl, α-sulfamoylphenylacetyl, α-phenoxycarbonylphenylacetyl, α-(p-tolyloxycarbonyl)-phenylacetyl, and α-formyloxyphenylacetyl.

Examples of the acyl group represented by the formula R$^{18}$—R$^{19}$—CH$_2$—CO— are cyanoacetyl, acetoacetyl, phenylacetyl, phenoxyacetyl, 5-amino-5-carboxyvaleryl, 5-oxo-5-carboxyvaleryl, 4-carboxybutyryl, trifluoromethylthioacetyl, cyanomethylthioacetyl, 1H-tetrazolyl-1-acetyl, thienylacetyl, 2-(2-amino-4-thiazolyl)acetyl, 4-pyridylthioacetyl, 2-thienylthioacetyl, 3,5-dichloro-1,4-dihydro-4-oxopyridine-1-acetyl, β-carboxyvinylthioacetyl, and 2-(2-aminomethylphenyl)acetyl.

The amino and/or carboxyl and/or hydroxyl group in the above acyl group may have a protective group.

The protective group for said amino group may be the same as the protective group for the above-mentioned amino group. The protective group for the carboxyl group may be any of known carboxyl-protecting groups generally usable in the field of beta-lactam and organic chemistry, for example, ester residues, silyl groups and so on, such as C$_{1-6}$ alkyl (e.g. methyl, ethyl, n-propyl, isopropyl, tert-butyl, tert-amyl, etc.), aralkyl*(e.g. benzyl, 3,5-di-tert-butyl-4-hydroxybenzyl, p-nitrobenzyl, p-methoxybenzyl, etc.), 1-indanyl, aryl*-(e.g. phenyl, p-nitrophenyl, etc.), alkyl*(e.g. methoxymethyl, benzhydryl, ethoxymethyl, phenacyl, benzyloxymethyl, acetoxymethyl, pivaloyloxymethyl, β-methylsulfonylethyl, β-trimethylsilylethyl, methylthiomethyl, trityl, β,β,β-trichloroethyl, β-iodoethyl, acetylmethyl, p-nitrobenzoylmethyl, p-mesylbenzoylmethyl, phthalimidomethyl, propionyloxymethyl, 1,1-dimethylpropyl, succinimidomethyl, mesylmethyl, benzenesulfonylmethyl, phenylthiomethyl, dimethylaminoethyl, pyridine-1-oxido-2-methyl, methylsulfinylmethyl, bis(p-methoxyphenyl)methyl and 2-cyano-1,1-dimethylethyl, etc.), alkenyl*(e.g. 3-methyl-3-butenyl, etc.), silyl (e.g. trimethylsilyl, dimethylsilyl, etc.). The protective group for the hydroxyl group may be any of hydroxyl-protecting groups generally usable in the field of beta-lactam and organic chemistry, for example, ester residues such as acetyl and chloroacetyl, esterified carboxyl groups such as β,β,β-trichloroethoxycarbonyl and β-trimethylsilylethoxycarbonyl, ether residues such as tert-butyl, benzyl, p-nitrobenzyl, trityl, methylthiomethyl and β-methoxyethoxymethyl, silyl ether residues such as trimethylsilyl and tert-butyldimethylsilyl, and acetal residues such as 2-tetrahydropyranyl and 4-methoxy-4-tetrahydropyranyl. The selection of the above protective groups is not critical in practicing the invention as in the case of the amino- and carboxyl-protecting groups.

The symbol R' in formulas [I] and [II] represents a hydrogen atom or an ester residue. The ester residue represented by R' includes, among others, $C_{1-6}$ alkyl (e.g. methyl, ethyl, n-propyl, isopropyl, tert-butyl, tert-amyl, etc.), aralkyl*(e.g. benzyl, p-nitrobenzyl, p-methoxybenzyl, diphenylmethyl, bis(p-methoxyphenyl)methyl, etc.) and the like.

The symbol $R^4$ in formula [I] represents a residue of a nucleophilic compound. The nucleophilic compound includes a wide variety of nucleophilic substances so far described in the literature in the field of cephalosporin chemistry and characterized by their having, for instance, a nucleophilic nitrogen, carbon or sulfur atom. Such nucleophilic compound is, for example, a nucleophilic sulfur containing compound, a nucleophilic nitrogen containing compound or a nucleophilic carbon containing compound. The nucleophilic sulfur containing compound ($R^{4a}$—SH) includes, among others, alkyl*thiol, aryl*thiol, aralkyl*thiol or nitrogen-containing heterocyclethiols which contain 1–5 nitrogen atoms and may contain an oxygen, sulfur and/or other hetero atom or atoms than nitrogen (alkyl*, aryl* and aralkyl* have the same meaning as defined above in $R^1$). The heterocyclethiols may be substituted on their nucleus. Examples of such nitrogen-containing heterocyclic groups are 6-membered nitrogen-containing heterocyclic groups such as pyridyl, N-oxidopyridyl, pyrimidyl, pyridazinyl, N-oxidopyridazinyl and triazinyl, 5-membered nigrogen-containing heterocyclic groups such as imidazolyl, thiazolyl, thiadiazolyl, oxadiazolyl, triazolyl and tetrazolyl, and fused rings corresponding thereto.

These nitrogen-containing heterocyclic groups may have such substituents as hydroxyl, amino, carboxyl, trifluoromethyl, carbamoyl, lower alkyl (e.g. methyl, ethyl, propyl, isopropyl, butyl, isobutyl), lower alkoxy (e.g. methoxy, ethoxy, propoxy, butoxy), halogen (e.g. chloro, bromo) and various substituents having a valence through a polyvalent group such as lower alkylene, —S— or

When the polyvalent group is a lower alkylene group, the substituents may be mono- or di-lower alkylamino, morpholino, carboxyl, sulfo, carbamoyl, alkoxycarbonyl, lower alkylcarbamoyl, alkoxy, alkylthio, alkylsulfonyl, acyloxy, morpholinocarbonyl, etc. (the acyl group is as defind above in $R^1$). When the polyvalent group is —S— or

the substituents may be lower alkyl, lower alkylene having such a substituent as mentioned above, etc. Furthermore, when the polyvalent group is

an alkoxycarbonyl, acyl, carbamoyl, lower alkylcarbamoyl or like group may directly be bonded thereto. A typical one of $R^{4a}$ is a $C_{1-6}$ alkyl, phenyl which may be substituted with carboxyl or an unsubstituted or substituted 5- or 6-membered nitrogen containing heterocyclic group or its group fused with benzene, the substituent being a $C_{1-6}$ alkyl, mono- or di-$C_{1-6}$ alkylamino-$C_{1-6}$ alkyl, carboxyl-$C_{1-6}$ alkyl, oxo, hydroxyl, carboxyl, or $C_{1-6}$ alkoxycarbonyl-$C_{1-6}$ alkilthio.

Specific examples of the heterocyclethiol are pyridinethiol, pyrimidinethiol, methylpyridazinethiol, 4,5-dihydro-6-hydroxy-4-methyl-1,2,4-triazin-3-thiol, 2-methyl-5,6-dioxo-1,2,5,6-tetrahydro-1,2,4-triazin-3-thiol, 2,5-dihydro-2-methyl-5-oxo-1,2,4-triazin-3-thiol, imidazol-thiol, 1,3,4-thiadiazolethiol, 1,2,3-thiadiazol-5-thiol, 2-methyl-1,3,4-thiadiazolethiol, thiazolethiol, 5-methyl-1,3,4-oxadiazolethiol, 1,2,3-triazol-5-thiol, 1-methyltetrazolethiol, 1-(2-dimethylaminoethyl)-tetrazolethiol, 1-(2-sulfoethyl)-tetrazolethiol, 1-sulfomethyltetrazolethiol and 1-carboxymethyltetrazolethiol. There may also be used aliphatic or aromatic thiols such as methanethiol, ethanethiol and thiophenol, thiourea, thiourea derivatives such as N-methylthiourea, thioamide derivatives such as thioacetamide and thiobenzamide, and so on. These nucleophilic sulfur-containing compounds may be submitted to the reaction in the free form or in the form of salt formed between their acidic group and a base or between their basic group and an acid. The nucleophilic nitrogen-containing compound includes, among others, tertiary aliphatic, aromatic, aromatic-aliphatic and cyclic amines, for example, trialkylamines (e.g. triethylamine), pyridine bases (e.g. pyridine, alkylpyridines) and heterocyclic amines containing more than one hetero atoms at least one of which is a nitrogen atom, such as pyrimidines, purines, pyridazines, pyrazines, pyrazoles, imidazoles, triazoles and thiazoles. Preferred nucleophilic nitrogen-containing compounds are compounds of the formula

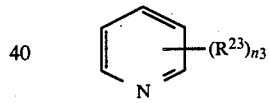

[XI]

wherein $n_3$ is an integer of 0 or 1–5 and $R^{23}$, which, when $n_3$ is 2–5, may be the same or different, is an aliphatic group such as lower alkyl (e.g. methyl, ethyl, n-propyl, isopropyl), an aryl group such as phenyl, an aromatic-aliphatic group such as phenyl-lower alkyl (e.g. benzyl, phenylethyl), alkoxymethyl such as methoxymethyl, ethoxymethyl, n-propoxymethyl or isopropoxymethyl, acyloxymethyl such as alkanoyloxymethyl (e.g. acetoxymethyl), formyl, carbamoyl, acyloxy such as alkanoyloxy (e.g. acetoxy), esterified carboxy, alkoxy such as methoxy, ethoxy, n-propoxy or isopropoxy, aryloxy such as phenoxy, aralkoxy such as benzyloxy, alkylthio such as methylthio or ethylthio, arylthio, aralkylthio, cyano, hydroxy, N-mono-lower alkylcarbamoyl such as N-methylcarbamoyl or N-ethylcarbamoyl, N,N-di-lower alkylcarbamoyl such as N,N-dimethylcarbamoyl or N,N-diethylcarbamoyl, N-(hydroxy-lower alkyl)carbamoyl such as N-(hydroxymethyl)carbamoyl or N-(hydroxyethyl)carbamoyl, carbamoyl-lower alkyl such as carbamoylmethyl or carbamoylethyl, or the like group. A frequently used one of a nucleophilic nitrogen-containing compound is a compound of the formula

wherein $R^{23a}$, $R^{23b}$ and $R^{23c}$ may be the same or different and each is a $C_{1-6}$ alkyl which may be substituted with a 5-membered nitrogen-containing heterocyclic group; or $R^{23a}$, $R^{23b}$ and $R^{23c}$ combinedly with the nitrogen atom adjacent to them represent an unsubstituted or substituted 5- or 6-membered nitrogen-containing heterocyclic group, the substituent being carbamoyl, cyano, $C_{1-6}$ alkoxycarbonyl or $C_{1-6}$ alkyl group.

Specific examples are such nitrogen-containing heterocyclic compounds as pyridine, picoline, nicotinic acid, nicotinamide, isonicotinamide, pyridinesulfonic acid, pyrazine, 2-carbamoylpyrazine, pyridazine, pyrimidine, imidazole and 1-methyl-imidazole. The nucleophilic carbon-containing compound includes inorganic cyanides, pyrroles and substituted pyrroless (e.g. indoles) and compounds capable of yielding stabilized carbanions, such as acetylenes, $\beta$-diketone compounds, e.g. acetoacetic acid esters and malonic acid esters as well as cyclohexane-1,3-diones, enamines, inamines and enols. For instance, compounds capable of introducing a group represented by the formula

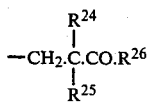 [XII]

wherein $R^{24}$ and $R^{25}$ may be the same or different and each is hydrogen, cyano, lower alkyl (e.g. methyl, ethyl), phenyl, substituted phenyl (e.g. halo-, lower alkyl-, lower alkoxy-, nitro-, amino- or lower alkylamino-phenyl), lower alkoxycarbonyl, mono- or diaryl-lower alkoxycarbonyl, lower alkylcarbonyl, aryllower alkyl or $C_5$ or $C_6$ cycloalkyl, and $R^{26}$ is hydrogen, lower alkyl (e.g. methyl, ethyl), phenyl, substituted phenyl (e.g. halo-, lower alkyl-, lower alkoxy-, nitro-, amino- or lower alkylamino-phenyl), aryl-lower alkyl or $C_5$ or $C_6$ cycloalkyl, into the substituent at the 3-position of the cephalosporin nucleus are used.

A preferable one of the nucleophilic compound is a group of the formula $$R^{4b}-SH \quad [C]$$

wherein $R^{4b}$ is a $C_{1-6}$ alkyl, phenyl which may be substituted with carboxyl or substituted or unsubstituted tetrazolyl, thiadiazolyl, benzothiazolyl, benzoxazolyl, benzoimidazolyl, pyrimidinyl, N-oxido-pyridyl or triazinyl, the substituent being a $C_{1-6}$ alkyl, di-$C_{1-6}$ alkylamino-$C_{1-6}$ alkyl, carboxy-$C_{1-6}$ alkyl, $C_{1-6}$ alkoxycarbonyl-$C_{1-6}$ alkylthio, oxo, hydroxyl or carboxyl; or a group of the formula

 [D]

wherein $R^{4c}$, $R^{4d}$ and $R^{4e}$ may be the same or different and each is a $C_{1-6}$ alkyl, or tetrazolyl-$C_{1-6}$ alkyl, or $R^{4c}$, $R^{4d}$ and $R^{4e}$ combinedly with the nitrogen atom adjacent to them represent a substituted or unsubstituted pyridine or pyrrole, the substituent being carbamoyl, cyano, $C_{1-6}$ alkoxycarbonyl or $C_{1-6}$ alkyl.

In formula [I] and [II], the dotted line

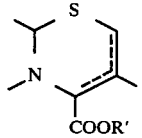

either denotes the double bond at position 2 of the cephem ring structure

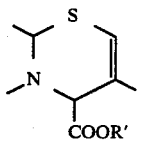

or the double bond at position 3

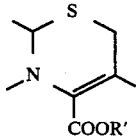

The cyclic compound of trivalent or pentavalent phosphorus to be used in the practice of the invention has the partial structure represented by formula [III] as the main part, or at least as part, of its chemical structure. Accordingly, P in formula [III] represents a trivalent or pentavalent phosphorus atom. In formula [III], W is an oxygen or sulfur atom or $NR^2$, and $W^1$ is an oxygen or sulfur atom or $NR^3$. W and $W^1$ may be the same or different. Generally, it is advantageous that W and $W^1$ are the same. $R^2$ and $R^3$ are the same or different and each is a hydrogen atom or a hydrocarbyl group. The hydrocarbyl group represented by $R^2$ and/or $R^3$ includes, among others, alkyl*, cycloalkyl*, alkenyl*, cycloalkenyl*, alkynyl*, aryl* and aralkyl*. As the alkyl*, cycloalkyl*, alkenyl*, cycloalkenyl*, aryl* and aralkyl* groups, those mentioned for the symbols $R^5-R^{19}$ are preferredly used. The alkynyl group is preferably a straight or branched lower alkynyl containing 2-6 carbon atoms, such as ethynyl, 1-propynyl or 2-propynyl. The alkynyl may be substituted by such a substituent as mentioned as the substituent for the alkyl* and alkenyl* groups represented by $R^5-R^{19}$.

Such cyclic trivalent or pentavalent phosphorus compound may be represented, for example, by the formula

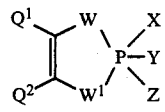 [XIII]

or by the formula

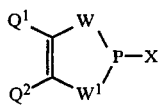 [XIV]

wherein $Q^1$ and $Q^2$ are the same or different and each is a hydrocarbyl group or a heterocyclic* group or $Q^1$ and $Q^2$ combinedly together with

represent a cyclic hydrocarbyl group or a heterocyclic* group, X, Y and Z are the same or different and each is a group represented by the formula

$$-W^2-Q^3$$

in which $W^2$ is an oxygen or sulfur atom, $NR^{28}$ ($R^{28}$ being a hydrogen atom or a hydrocarbyl group) or a bond and $Q^3$ is a halogen atom or a hydrocarbyl or heterocyclic* group and in which, when $Q^3$ is a halogen atom, $W^2$ is a bond, or two of X, Y and Z combinedly represent an oxo group or a group represented by the formula

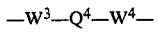
$$-W^3-Q^4-W^4-$$

in which $Q^4$ is a hydrocarbon or heterocyclic* group and $W^3$ and $W^4$ are the same or different and each is an oxygen or sulfur atom, $NR^{29}$ ($R^{29}$ being a hydrogen atom or a hydrocarbyl group) or a bond valence), X further represents a group of the formula

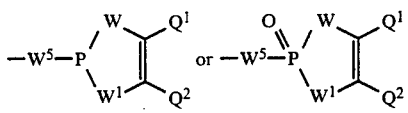

in which $W^5$ is an oxygen or sulfur atom or $NR^{30}$ ($R^{30}$ being a hydrogen atom or a hydrocarbyl group) and other symbols are as defined previously, and the remaining symbols W and $W^1$ are as defined above. In formulas [XIII] and [XIV], $Q^1$ and $Q^2$ are the same or different and each is a hydrocarbyl or heterocyclic* group. The hydrocarbyl group represented by $Q^1$ and/or $Q^2$ includes those examples mentioned above for $R^2$ and $R^3$, for instance, and the heterocyclic* group includes those mentioned above for $R^5$-$R^{19}$, among others. Furthermore, $Q^1$ and $Q^2$ may, combinedly together with the adjacent hydrocarbon group

represent a cyclic hydrocarbyl or heterocyclic* group. Said cyclic hydrocarbyl group is, for example, a cycloalkenyl* or aryl* group. The cycloalkenyl* and aryl groups each includes those examples given above for $R^2$ and $R^3$, among others. Generally, it is advantageous that $Q^1$ and $Q^2$ are the same or that they combinedly represent a cyclic hydrocarbyl group. X, Y and Z are the same or different and each is a group of the formula

$$-W^2-Q^3$$

wherein $W^2$ is an oxygen or sulfur atom, $NR^{28}$ ($R^{28}$ being a hydrogen atom or a hydrocarbyl group) or a bond valence and $Q^3$ is a halogen atom or a hydrocarbyl or heterocyclic* group and wherein, when $Q^3$ is a halogen atom, $W^2$ is a bond valence. $R^{28}$ in $NR^{28}$ represented by $W^2$ is a hydrogen atom or a hydrocarbyl group. The hydrocarbyl group represented by $R^{28}$ and the hydrocarbyl and heterocyclic* groups represented by $Q^3$ respectively include the examples mentioned above for $Q^1$ and $Q^2$, for instance. $W^2$ may be the same as or different from the above-mentioned W and/or $W^1$. The halogen atom represented by $Q^3$ includes those examples given above for $R^5$-$R^{19}$. Two of X, Y and Z, for example X and Y, or Y and Z, may combinedly represent a group of the formula $-W^3-Q^4-W^4-$. $Q^4$ is a hydrogen or heterocyclic* group, and such hydrocarbon and heterocyclic groups include those examples mentioned above for $Q^1$ and $Q^2$, for instance. $W^3$ and $W^4$ may be the same or different and such is an oxygen or sulfur atom, $NR^{29}$ or a bond valence. $R^{29}$ is a hydrogen atom or a hydrocarbyl group. The hydrocarbyl group represented by $R^{29}$ includes those examples mentioned above for $R^2$ and $R^3$, among others. $W^3$ and $W^4$ each may be the same or different from the above-mentioned W and/or $W^1$. Furthermore, X may be a group represented by the formula

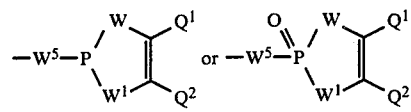

wherein W, $W^1$, $Q^1$ and $Q^2$ are as defined above. $W^5$ is an oxygen or sulfur atom or $NR^{30}$ in which $R^{30}$ is a hydrogen atom or a hydrocarbyl group. The hydrocarbyl group represented by $R^{30}$ includes those examples mentioned above for $R^2$ and $R^3$, for instance. Preferred among such cyclic trivalent or pentavalent phosphorus compounds are cyclic phosphorus compounds represented, for example, by the formula

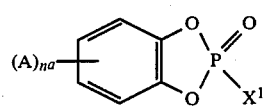 [XV]

wherein A is a substituent on the benzene ring, $n^a$ is an integer of 0 to 4 and $X^1$ is halogen, alkyl*, aralkyl*, alkyl*oxy, aryl*oxy, aralkyl*oxy, alkyl*amino, aryl*amino, aralkyl*amino or aryl* or by the formula

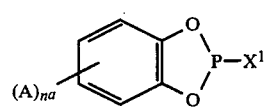 [XVI]

wherein A, $n^a$ and $X^1$ are as defined above, or by the formula

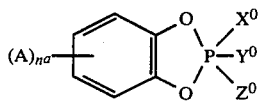 [XVII]

wherein A and $n^a$ are as defined above and $X^0$, $Y^0$ and $Z^0$ are the same or different and each has the same meaning as $X^1$. A in formulas XV, XVI, and XVII is a substituent on the benzene ring and may be any one inert to the reaction, for instance, alkyl*, alkyl*oxy, alkyl*thio, halogen atom, nitro, cyano, hydroxyl, carboxyl, alkyl*oxycarbonyl, alkyl*sulfonyl, carbamoyl, alkyl*carbamoyl, aliphatic acyl (e.g. acetyl, propionyl) or aromatic acyl (e.g. benzoyl, p-chlorobenzoyl). Furthermore, A may be methylenedioxy, a group of the formula

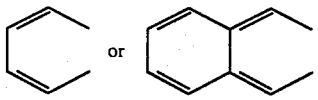

or a like group, which may be substituted by halogen (e.g., chlorine, bromine, etc.), nitro, cyano and/or the like. Referring to A, $X^1$, $X^0$, $Y^0$ and $Z^0$, the halogen atom, and alkyl*, aryl* and aralkyl* groups each includes the corresponding examples such as mentioned for $R^5$–$R^{19}$. Preferred examples of $X^1$, $X^0$, $Y^0$ and $Z^0$ are halogen atoms such as chlorine, bromine and fluorine, $C_{1-5}$ lower alkyloxy groups, which may be substituted, such as methoxy, ethoxy, 2,2,2-trichloroethoxy, 2-cyanoethoxy and 2-methylsulfonylethoxy, aryloxy groups, which may be substituted, such as phenoxy, 4-chlorophenoxy and 4-nitrophenoxy, aralkyloxy groups, which may be substituted, such as benzyloxy, aryloxy, p-nitrobenzyloxy and 1,1-dimethylaryloxy, alkyl groups which may be substituted, such as methyl, ethyl, propyl, 2-chloroethyl and 2-methoxyethyl, and aryl groups which may be substituted, such as phenyl, tolyl and chlorophenyl. Two of $X^0$, $Y^0$ and $Z^0$, for instance $X^0$ and $Y^0$, or $Y^0$ and $Z^0$, may combinedly represent o-phenylenedioxy, ethylenedioxy or the like. In formulas [XV] and [XVI], $X^1$ may also represent a linking group —O—, so that the cyclic phosphorus compound may be in the form of dimer.

A frequently used one of the trivalent or pentavalent cyclic phosphorus compound is a compound of the formula

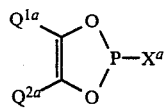 [E]

or

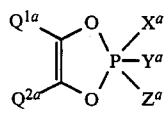 [F]

wherein $Q^{1a}$ and $Q^{2a}$ are a $C_{1-6}$ alkyl or $Q^{1a}$ and $Q^{2a}$ combinedly together with represent benzene which may be substituted with a $C_{1-6}$ alkyl, hydroxyl or $C_{1-6}$ alkoxycarbonyl, and $X^a$, $Y^a$ and $Z^a$ are the same or different and each is a halogen atom, a $C_{1-6}$ alkylamino, $C_{6-10}$ aryl or a group of the formula —O—$Q^{3a}$ wherein $Q^{3a}$ is an unsubstituted or substituted $C_{1-6}$ alkyl, $C_{2-6}$ alkenyl, $C_{3-8}$ cycloalkyl or $C_{6-10}$ aryl, the substituent being a halogen atom or nitro group, or two of $X^a$, $Y^a$ and $Z^a$ combinedly represent an oxo group or a group of the formula

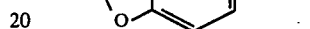

wherein $A^a$ is a halogen atom and $n^a$ is an integer of 0 to 4.

A preferable one of the pentavalent cyclic phosphorus compound is a compound of the formula

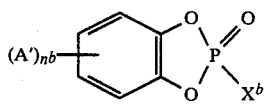

wherein A' is hydroxyl, $C_{1-6}$ alkyl or $C_{1-6}$ alkoxycarbonyl, $n^b$ is zero or 1 and $X^b$ is a $C_{1-6}$ alkoxy, phenyl or phenoxy.

Examples of the cyclic phosphorus compound are o-phenylene phosphorochloridate, o-phenylene phosphorofluoridate, methyl o-phenylene phosphate, ethyl o-phenylene phosphate, n-propyl o-phenylene phosphate, isopropyl o-phenylene phosphate, n-butyl o-phenylene phosphate, isobutyl o-phenylene phosphate, sec-butyl o-phenylene phosphate, cyclohexyl o-phenyelen phosphate, phenyl o-phenylene phosphate, p-chlorophenyl o-phenylene phosphate, p-acetylphenyl o-phenylene phosphate, 2-chloroethyl o-phenylene phosphate, 2,2,2-trichloroethyl o-phenylene phosphate, ethoxycarbonylmethyl o-phenylene phosphate, carbamoylmethyl o-phenylene phosphate, 2-cyanoethyl o-phenylene phosphate, 2-methylsulfonylethyl o-phenylene phosphate, benzyl o-phenylene phosphate, 1,1-dimethyl-2-propenyl o-phenylene phosphate, 2-propenyl o-phenylene phosphate, 3-methyl-2-butenyl o-phenylene phosphate, 2-thienylmethyl o-phenylene phosphate, 2-furfurylmethyl o-phenylene phosphate, bis-o-phenylene pyrophosphate, 2-phenyl-1,3,2-benzodioxaphosphole-2-oxide, 2-(p-chlorophenyl)-1,3,2-benzodioxaphosphole-2-oxide, 2-(n-butyl)-1,3,2-benzodioxaphosphole-2-oxide, 2-anilino-1,3,2-benzodioxaphosphole-2-oxide, 2-phenylthio-1,3,2-benzodioxaphosphole-2-oxide, 2-methoxy-5-methyl-1,3,2-benzodioxaphosphole-2-oxide, 2-chloro-5-ethoxycarbonyl-1,3,2-benzodioxaphosphole-2-oxide, 2-methoxy-5-ethoxycarbonyl-1,3,2-benzodioxaphosphole-2-oxide, 5-ethoxycarbonyl-2-phenyl-1,3,2-benzodioxaphosphole-2-oxide, 2,5-dichloro-1,3,2-benzodioxaphosphole-2-oxide, 4-chloro-2-methoxy-1,3,2-benzodioxaphosphole-2-oxide, 2-methoxy-4-methyl-1,3,2-benzodioxaphosphole-2-oxide, 2,3-naphthylene methyl phosphate, 5,6-dimethyl- 2-methoxy-1,3,2-benzodioxaphosphole-2-oxide, 2,2,-dihydro-4,5,6,7-tetrachloro-2,2,2-trimethoxy-1,3,2-benzodioxaphosphole, 2,2-dihydro-4,5,6,7-tetrachloro-2,2,2-triphenoxy-1,3,2-benzodioxaphosphole, 2,2-dihydro-2,2-ethylenedioxy-2-methoxy-1,3,2-benzodioxaphosphole, 2,2-dihydro-2-benzyl-2,2-dimethoxy-1,3,2-benzodioxaphosphole, 2,2-dihydro-4,5-benzo-2,2,2-trimethoxy-1,3,2-benzodioxaphosphole, 2,2-dihydro-2,2,2-triphenoxy-1,3,2-benzodioxaphosphole, 2,2-dihydro-2,2-(o-phenylenedioxy)-2-phenoxy-1,3,2-benzodioxaphosphole, 2-chloro-2,2-dihydro-2,2-(o-phenylenedioxy)-1,3,2-benzodioxaphosphole, 2,2-dihydro-2-methoxy-2,2-(o-phenylenedioxy)-1,3,2-benzodioxaphosphole, 2,2-dihydro-2,2,2-trichloro-1,3,2-benzodioxaphosphole, 9,10-phenanthrenedioxytrimethoxyphosphorus, o-phenylene phosphorochloridite, o-phenylene phosphorobromidite, o-phenylene phosphorofluoridite, methyl o-phenylene phosphite, n-butyl o-phenylene phosphite, methoxycarbonylmethyl o-phenylene phosphite, phenyl o-phenylene phosphite, p-chloro (or p-nitro)phenyl o-phenylene phosphite, 2-phenyl-1,3,2-benzodioxaphosphole, bis-o-phenylene pyrophosphite, 2-methoxy-5-methyl-1,3,2-benzodioxaphosphole, 5-acetyl-2-phenoxy-1,3,2-benzodioxaphosphole, 9,10-phenanthrene phosphorochloridite, 2-chloro-4-methyl-1,3,2-benzodioxaphosphole, 5-ethoxycarbonyl-2-phenyl-1,3,2-benzodioxaphosphole, 2-chloro-2-thioxo-1,3,2-benzodioxaphosphole, 2-phenoxy-2-oxo-1,3,2-benzodiazaphosphole, 2-phenoxy-1,3,2-benzoxazaphosphole, 2,2-dihydro-2-oxo-2-methoxy-4,5-dimethyl-1,3,2-dioxaphosphole, 2,2-dihydro-2-oxo-2-chloro-4,5-dimethyl-1,3,2-dioxaphosphole, 2,2-dihydro-2-oxo-2-(1-imidazolyl)-4,5-dimethyl-1,3,2-dioxaphosphole, 2,2-dihydro-2,2-ethylenedioxy-2-methoxy-4,5-dimethyl-1,3,2-dioxaphosphole, 2,2-dihydro-2,2-dimethoxy-2-phenoxy-4,5-dimethyl-1,3,2-dioxaphosphole, 2,2-dihydro-2,2,2-trimethoxy-4,5-dimethyl-1,3,2-dioxaphosphole, 2,2-dihydro-2,2,2-triphenoxy-4,5-dimethyl-1,3,2-dioxaphosphole, 2,2-dihydro-2,2,2-triethoxy-4,5-diphenyl-1,3,2-dioxaphosphole, 2,2-dihydro-2,2,2-trimethoxy-4,5-diphenyl-1,3,2-dioxaphosphole, 2,2-dihydro-2-oxo-2-methoxy-4,5-diphenyl-1,3,2-dioxaphosphole, 2,2-dihydro-2,2,2-trimethoxy-1,3,2-dioxaphosphole, 2,2-dihydro-2,2,2-trimethoxy-4-phenyl-1,3,2-dioxaphosphole, 2,2-dihydro-2,2,2-trimethoxy-4-methyl-1,3,2-dioxaphosphole, 2,2-dihydro-2,2,2-trimethoxy-4-methyl-5-phenylcarbamoyl-1,3,2-dioxaphosphole, 2,2,4,5,6,7-hexahydro-2,2,2-trimethoxy-1,3,2-benzodioxaphosphole, 2,2'-oxybis(4,5-dimethyl-2,2-dihydro-1,3,2-dioxaphosphole), and 2,2'-oxybis(4,5-dimethyl-2,2-dihydro-1,3,2-dioxaphosphole-2-oxide).

These cyclic phosphorus compounds are either available commercially or per se known compounds [R. S. Edmundson et al., Chemistry and Industry, 1962, 1770–1778; K. Darell Berlin et al., Tetrahedron, 1964, 20, 2709–2716; F. Ramirez et al., Tetrahedron, 1968, 24, 5041–5051; L. Anschütz et al., Annalen, 1927, 454, 109–120; T. Koizumi et al., Tetrahedron Letters, 1973, 4763–4766; P. C. Crofts et al., J. Chem. Soc., 1958, 4250–4254; Marianne M. C. F. Castelijins et al., J. Org. Chem., 1981, 46, 47–53] or can be produced by the known methods. They may be used either in a purified form or as yielded by the reaction.

In the practice of the invention, a product resulting from the reaction of a compound having the partial structure [IV] with a phosphorus oxyhalide, phosphorus trihalide or phosphorus pentahalide may be used in place of the cyclic trivalent or pentavalent phosphorus compound mentioned above. The compound having the partial structure [IV] is, for example, a compound of the formula

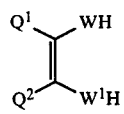

[XVIII]

wherein the symbols are as defined above. A preferred example is a compound of the formula

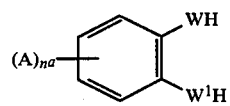

[XIX]

wherein the symbols are as defined above. And, a frequently used one is a compound of the formula

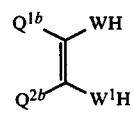

[G]

wherein $Q^{1b}$ and $Q^{2b}$ is combinedly represent an aryl group which may be substituted with a $C_{1-6}$ alkoxycarbonyl group. Specific examples are catechol, ethyl 3,4-dihydroxybenzoate, 2,3-dihydroxynaphthalene, 3,4-dihydroxytoluene, 2,3-dihydroxytoluene, 3,4-dihydroxychlorobenzene and o-aminophenol. The halogen in said phosphorus oxyhalide, phosphorus trihalide and phosphorus pentahalide is, for example, chlorine or bromine. Thus, specifically, phosphorus oxychloride, phosphorus trichloride, phosphorus pentachloride, phosphorus tribromide and phosphorus oxybromide, for instance, are used. The reaction product from a compound having the partial structure [IV] and a phosphorus oxyhalide, phosphorus trihalide or phosphorus pentahalide is, for example, the reaction mixture as obtained from the reaction therebetween. Generally, an about equimolar amount of a phosphorus oxyhalide or phosphorus trihalide or about ⅓ to 1.0 mole equivalent of a phosphorus pentahalide is used per mole of the compound having the partial structure [IV]. The reaction is preferably carried out in a solvent, such as methylene chloride, 1,2-dichloroethane, acetonitrile, ethyl acetate, tetrahydrofuran, dioxane, ether, benzene or bromobenzene. Among others preferred are methylene chloride, acetonitrile and tetrahydrofuran. In some cases, favorable results are obtained by carrying out the reaction in the presence of a base. Usable bases are, for example, triethylamine, dicyclohexylamine, diisobutylamine and di-n-butylamine, and preferred amines are, for example, triethylamine, tri-n-butylamine and di-n-butylamine. The reaction is carried out generally at −50° C. to +100° C., preferably at −20° C. to +50° C., for 5–120 minutes, preferably 10–60 minutes. However, the reaction temperature and period are not limited to the above provided that the desired reaction product is obtained. Generally, the reaction mixture is used as it is as a raw material for the reaction proper without isolation. However, if necessary, the unreacted starting material, namely the compound having the partial structure [IV], the phosphorus oxyhalide, phosphorus trihalide or phosphorus pentahalide and/or the hydrogen halide resulting from the reaction or the salt thereof with the base may be separated prior to the reaction proper in accordance with the invention.

Some of the compounds having the partial structure [IV] are commercially available and others can be produced by known methods or modifications thereof.

In accordance with the invention, the desired products [I] can be produced by reacting a compound [II] with a nucleophilic ompound and (1) a cyclic trivalent or pentavalent phosphorous compound having the partial structure [III] or (2) a reaction product from a compound having the partial structure [IV] and a phosphorus oxyhalide, phosphorua trihalide or phosphorus pentahalide (such reaction product hereinafter also referred to simply as "reaction product"), in an organic solvent.

The compound [II] may be used either in the free form with regard to the acidic group such as carboxyl or sulfo or in the form of salt with a nontoxic cation such as sodium or potassium or an organic amine such as triethylamine, tri-n-butylamine, di-n-butylamine, dicyclohexylamine, pyridine, collidine or 2,6-lutidine. When the basic group is contained in R and/or $R^1$, said group may be in the form of salt with an organic acid such as acetic acid, tartaric acid or methanesulfonic acid or an inorganic acid such as hydrochloric acid, hydrobromic acid, sulfuric acid or phosphoric acid or the like. The nucleophilic compound may take the form of basic salt or acidic salt depending on the kind thereof, and such basic salt and acidic salt may also be used as a raw material in practicing the invention. The basic salt and acidic salts are, for example, of the same kind as those mentioned above for compound [II].

The compound [II], the nucleophilic compound and (1) the cyclic trivalent or pentavalent phosphorus compound having the partial structure [III] or (2) the reaction product from the compound having the partial structure [IV] and phosphorus oxyhalide, phosphorus trihalide or phosphorus pentahalide as well as the organic solvent may be charged in the optional order. When the compound [II], nucleophilic compound, cyclic phosphorus compound and organic solvent are used, the reaction is generally carried by mixing the compound [II] with the nucleophilic compound in the organic solvent followed by addition of the cyclic phosphorus compound or a solution thereof in an organic solvent, or by mixing the cyclic phosphorus compound with the nucleophilic compound in the organic solvent followed by addition of the compound [II] or an organic solvent solution thereof. Also when the reaction product from the compound having the partial structure [IV] the phosphorus oxyhalide, phosphorus trihalide or phosphorus pentahalide is used, the reaction is carried out in the same manner as in the case where the cyclic phosphorus compound is used. As for the mixing ratio, it is preferably to use the nucleophilic compound in an amount of not less than 1.0 mole, more preferably 1.0–10.0 moles, per mole of the compound [II] and the cyclic phosphorus compound in an amount of not less than 1.0 mole, more preferably 1.0–6.0 moles, on the same basis. When the reaction product from the compound having the partial structure [IV] and phosphorus oxyhalide, phosphorus trihalide or phosphorus pentahalide is used, it is preferable to use not less than 1.0 mole, more preferably 1.0–10.0 moles, of the nucleophilic compound, 1.0–6.0 moles of the compound having the partial structure [IV] and 1.0–6.0 moles of the phosphorus oxyhalide or phosphorus trihalide or $\frac{1}{3}$–2.0 moles of the phosphorus pentahalide per mole of the compound [II].

Any organic solvent inert to the reaction may be used as the solvent in the reaction. Thus, usable are, for instance, amides such as formamide, dimethylformamide and dimethylacetamide, halogenated hydrocarbons such as chloroethane, isobutyl chloride, methylene chloride, chloroform, 1,2-dichloroethane, carbon tetrachloride, 1,1,1-trichloroethane, 1,1,2-trichloroethane, 1,1,2,2-tetrachloroethane, fluorobenzene and dichlorobenzene, ethers such as dimethyl ether, diethyl ether, tetrahydrofuran and dioxane, carboxylic acids such as glacial acetic acid and propionic acid, esters such as methyl acetate, ethyl acetate, isobutyl acetate, methyl propionate and ethylene carbonate, nitriles such as acetonitrile, propionitrile and benzonitrile, nitro compounds such as nitromethane and nitroethane, ketones such as acetone and methyl ethyl ketone, and hydrocarbons such as benzene, toluene and mesitylene, and mixtures of these. In particular, favorable results can be obtained when the reaction is carried out in such an organic solvent as methylene chloride, acetonitrile, formamide, formamide-acetonitrile mixture, methylene chloride-tetrahydrofuran mixture or methylene chloride-acetonitrile mixture. When the reaction product from the compound having the partial structure [IV] and phosphorus oxyhalide, phosphorus trihalide or phosphorus pentahalide is used, said reaction mixture itself may serve as the organic solvent. Depending on the kind of each starting material and/or organic solvent, the addition of a base may advantageously influence the reaction. The addition of such base can be made in an adequate manner at the time of mixing of the starting materials and organic solvent. Generally, said base is mixed with the organic solvent together with the compound [II] or nucleophilic compound. The base is preferably used generally in an amount of 0–5 moles per mole of the compound [II]. Any base capable of accelerating the reaction of neutralizing the acid resulting from the reaction or solubilizing any of the starting materials but inert to the reaction may be used as the base. For instance, $C_{1-6}$ alkylamine such as triethylamine, tri-n-butylamine, di-n-butylamine and diisobutylamine, $C_{3-8}$ cycloalkylamine such as dicyclohexylamine, cyclic amine such as pyridine and lutidine are preferably used. The reaction temperature and period may be varied depending on the kind and amount of compound [II], cyclic phosphorus compound or reaction product, nucleophilic compound, organic solvent and/or base. In some cases, the reaction is complete in a moment at a temperature as low as −60° C. Generally, however, the reaction is carried out under mild conditions at −80° C. to 50° C. and is complete in several seconds to ten and odd hours. In particular, the reaction is preferably carried out at −40° C. to 40° C. for 5–120 minutes. Although it is a general rule that a higher reaction temperature results in a shorter reaction time, the reaction is preferably carried out at relatively low temperature for prevention of side or secondary reactions, among others. The thus-obtained cephalosporin compound [I] can be isolated and purified by per se known methods, such as solvent extraction, pH adjustment, phase transfer, salting out, crystallization, recrystallization and chromatography. When the acyl group represented by $R^1$ is of a specific kind, it is also possible to convert [I], without isolation thereof, into the corresponding 7-aminocephem compound (compound of formula [I] wherein $R^1$ is a hydrogen atom), which is useful as an intermediate for the production of antibacterial substances, by a known method of cleaving acyl group at position 7 which comprises adding to the reaction mixture dimethylaniline, trimethylsilyl chloride, phosphorus pentachloride, methanol and water in that order. When the product [I] is in the free form, it may be converted into a salt in a conventional manner. The desired product of formula [I] also includes such a salt form. The salt forming component of such salt of product [I] may be of the same kind as that mentioned for the starting material [II]. Thus, the salt includes salts of the acidic group of [II] with alkali metals such as lithium, sodium and potassium, alklaine earth metals such as magnesium and calcium and amines such as di-n-butylamine, dicyclohexylamine, diisobutylamine, di-tert-butylamine, triethylamine, pyridine, 2,6-lutidine and tributylamine, and salts of the basic group of [II] with inorganic acids such as hydrochloric acid and sulfuric acid, organic acids such as oxalic acid, formic acid, trichloroacetic acid and trifluoroacetic acid, sulfonic acids such as methanesulfonic acid, toluenesulfonic acid, naphthalenesulfonic acid and camphor-sulfonic acid, phosphoric acids such as methylphosphoric acid, dimethylphosphoric acid and diphenylphosphoric acid, and phosphonic acids such as phenylphosphonic acid. Some of the thus-obtained products [I] are per se useful as antibacterial agents and others are useful as raw materials for the production of more potent antibacterial agent. For instance, the cephalosporin compound [I] which has a 5-phthalimido-5-carboxyvaleryl group as R¹ can be converted to the 7-[2-(2-aminothiazol-4-yl)acetamido] or 7-[2-(2-aminothiazol-4-yl)-2-methoxyiminoacetamido] compound by cleavage of the acyl group at position 7 of [I] by a conventional method, followed by reaction with (2-aminothiazol-4-yl)acetic or 2-(2-aminothiazol-4-yl)-2-methoxyiminoacetic acid or a reactive derivative thereof. An antibiotic substance, 7-[2-(2-aminothiazol-4-yl)acetamido]-3-[1-(2-dimethylaminoethyl)-1H-tetrazol-5-yl]thiomethyl-3-cephem-4-carboxylic acid, 7-[2-(2-aminothiazol-4-yl)-2-methoxyiminoacetamido]-3-(1-methyl-1H-tetrazol-5-yl)thiomethyl-3-cephem-4-carboxylic acid, for instance, can further be produced therefrom.

Preparation of some of the starting compounds [XV], i.e. 1,3,2-dioxaphospholes

The following concerns with the preparation of 1,3,2-dioxaphospholes of the formula

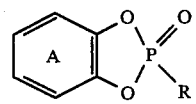

[I]B wherein

represents a benzene ring which may optionally be substituted and R represents an aryl, alkoxy or aralkyloxy group which may optionally be substituted.

The compounds of formula [I]B are useful, for example as neutral catalysts in deriving cephalosporin antibiotics, which have important value in the treatment of bacterial diseases, or intermediates therefor from penicillin compounds by ring expansion (Japanese Published Unexamined Patent Application No. 4091/1975) and are also useful in the production of cephalo compounds having a position 3 a methyl group substituted with a nucleophilic group, which compounds are important as antibiotics or intermediates therefor, by reaction of deacetylcephalosporin C (DCPC) obtainable by fermentative culture or a derivative thereof or of cephalosporin C also obtainable by fermentation, which derivative has a —CH₂OH group at position 3, with a nucleophilic reagent as mentioned hereinbefore.

A number of investigations have so far been made for the production of such 1,3,2-dioxaphospholes of formula [I]B, and [1] the route involving ①→②→③ [L. Anschutz, Annalen, 454, 109–120 (1927)], [2] the route ①→②→⑤→⑥ [T. A. Khwaja et al., J. Chem. Soc. (C), 1970, 2092–2100], and [3] the route ①→④→② [H. Gross et al., Chem. Ber., 96, 1387–1394 (1963) and East German Patent No. 50606 (laid open May 5, 1971)], for instance, are known, as illustrated in the following:

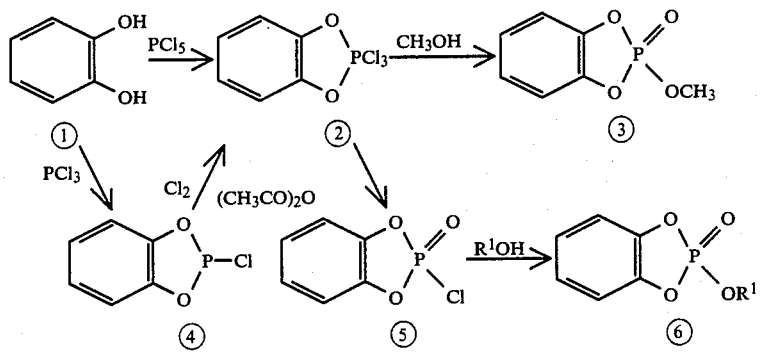

wherein R¹ is an alcohol residue. However, method [1] is disadvantageous in that the raw material PCl₅ is sublimable, hence can be handled with difficulty, that the yield is low and that methylchloride, which has an offensive odor and is hazardous, is produced, method [2] is also disadvantageous in that the number of steps involved is large, that the yield is low and that distillation of intermediates ② and ⑤ gives large amounts of residue having a tendency toward solidification, hence difficult to handle, and even method [3] is problematic in that the yield is low. Moreover, for all methods ①-③, intermediates ②, ④ and ⑤ and hygroscopic and easily decompose upon absorption of moisture, so that they are difficult to handle. For these and other reasons, these methods are all disadvantageous for large scale commercial production of [I]B. A more advantageous method for the production of [I]B has been longed for to be developed.

The present inventors conducted various investigations on the production of compounds [I]B and have no unexpectedly found that compounds [I]B can be obtained in one step in an industrially very advantageous manner in good yields in a short period of time by reacting a compound of the formula

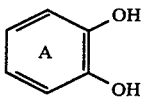   [II]B wherein

is as defined above, with a compound of the formula

   [III]B wherein X is a halogen atom and R is as defined above, at a temperature not higher than about 30° C. in the presence of a base.

Thus, the method of the preparation producing 1,3,2-dioxaphospholes [I]B, comprises reacting compound [II]B with compound [III]B at a temperature not higher than about 30° C. in the presence of a base.

In the above formulas,

is a benzene ring which may optionally be substituted and the benzene ring may have one to four substitutents, which are inert to the reaction, each selected from among a straight or branched $C_1$-$C_6$ lower alkyl group (e.g. methyl, ethyl, n-propyl, isopropyl, n-butyl, pentyl), a straight or branched $C_1$-$C_6$ lower alkoxy group (e.g. methoxy, ethoxy, isopropyloxy), a straight or branched $C_1$-$C_6$ lower alkylthio group (e.g. methylthio, ethylthio, n-propylthio, isopropylthio), a $C_2$-$C_6$ lower acyl group (e.g. acetyl, propionyl), a $C_2$-$C_6$ lower acyloxy group (e.g. acetoxy, propionyloxy), a $C_2$-$C_6$ lower acylamino group (e.g. acetylamino), a di-lower ($C_1$-$C_6$) alkylamino-lower ($C_1$-$C_6$) alkyl group (e.g. dimethylaminomethyl, dimethylaminoethyl, diethylaminomethyl, diethylaminoethyl), a $C_1$-$C_6$ lower alkoxycarbonyl or $C_6$-$C_{10}$ aryloxycarbonyl group (e.g. methoxycarbonyl, ethoxycarbonyl, phenoxycarbonyl), nitro, halogen (Br, Cl, I, F), cyano, carboxy, hydroxy or a like monovalent group. Furthermore, the benzene ring may have such a divalent substituent as methylenedioxy, ethylenedioxy,

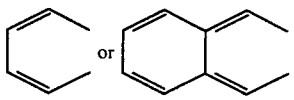

which substituent may further be substituted, for example with halogen, cyano, nitro, oxo and/or carboxyl. Specific examples of the compound of formula [II]B are pyrocatechol, homocatechol, pyrogallol, methyl 3,4-dihydroxybenzoate, 2-hydroxy-4-propionylphenol, 3,4-dihydroxychlorobenzene, 3,4-dihydroxymethoxybenzene and 1,2-dihydroxynaphthalene. In particular, pyrocatechol, for instance, is preferred.

In the above formula [III]B, X is a halogen atom such as F, Cl or Br. In particular, when X is Cl, good results are obtainable. R is an aryl, alkoxy or aralkyloxy group which may optionally be substituted. The aryl group includes, among others, phenyl, tolyl, xylyl, biphenylyl and naphthyl. The alkoxy group is, for example, a straight or branched $C_1$-$C_6$ lower alkoxy group such as mentioned above for

.

The aralkyloxy group includes benzyloxy, phenethyloxy, phenylpropyloxy, naphthylmethyloxy, etc. These aryl, alkoxy and aralkyloxy groups may optionally be substituted and the optional substituents include such halogen, nitro, cyano, oxo, $C_1$-$C_6$ lower alkoxy, $C_1$-$C_6$ lower alkylthio and alkoxycarbonyl groups as mentioned above for

and further a $C_1$-$C_6$ lower alkylsulfonyl group (e.g. methylsulfonyl, ethylsulfonyl, n-propylsulfonyl, isopropylsulfonyl, n-butylsulfonyl), allylsulfonyl, etc. Specific and preferred examples of R are methoxy, ethoxy, propyloxy, isopropyloxy, butyloxy, n-hexyloxy, benzyloxy, phenethyloxy, 2-cyanoethoxy, 2-methylsulfonylethoxy, 2-methoxycarbonylethoxy and 2-methoxyethoxy. In particular, when R is, for example, a lower alkoxy such as methoxy or ethoxy, good results are obtained.

The method of the preparation is carried out by reacting compound [II]B with compound [III]B at a temperature not higher than about 30° C. in the presence of a base.

Compound [II]B is submitted to the reaction either in the free or in the form of a salt with a base such as mentioned hereinbelow. The base to be used in practicing the method includes, among others, tertiary amines such as trimethylamine, triethylamine, tri-n-butylamine, N-methylpiperidine, cyclohexyldimethylamine and N-methylmorpholine, dialkylamines such as di-n-butylamine, diisobutylamine and dicyclohexylamine, aromatic amines such as pyridine, lutidine and γ-collidine, other organic amines, alkali metals such as lithium, sodium and potassium, alkaline earth metals such as calcium and magnesium, quaternary ammonium such as tetraethylammonium and tetrabutylammonium, and other inorganic bases. Said base may be used in the form of a salt with the phenol hydroxyl group of compound [II]B or may be added in carrying out the reaction or may be used in admixture with compound [II]B. Preferable bases are tri-lower ($C_1$-$C_6$) alkylamines such as trimethylamine, triethylamine and tri-n-butylamine and aromatic amines having a six-membered ring such as pyridine and lutidine. In particular, triethylamine, tri-n-butylamine, pyridine and the like are preferred.

The reaction is preferably carried out by mixing compound [II]B with compound [III]B and then mixing the mixture with a base at below about 30° C., by mixing compound [II]B with a base and then mixing the mixture with compound [III]B at below about +° C., or by mixing a salt of compound [II]B and a base such as mentioned above with compound [III]B at below about 30° C. The reaction temperature is preferably 0° C. or below, more preferably −5° C. to −40° C. The reaction can be carried out in a more advantageous manner by using a solvent. As the solvent, an organic which is inert to the reaction is used. Since the starting compound [III]B and the product [I]B are easily hydrolyzable upon contact with water, the use of an anhydrous aprotic solvent is practical. Examples of such solvent incapable of reacting with compound [III]B are halogenated hydrocarbons such as methylene chloride, chloroform, carbon tetrachloride, 1,2-dichloroethane and 1,1,2-trichloroethane, ethers such as dimethyl ether, methyl ethyl ether, diethyl ether, tetrahydrofuran and dioxane, organic nitriles such as acetonitrile and propionitrile, nitroalkanes such as nitromethane and nitroethane, esters such as methyl acetate, ethyl acetate and methyl propionate, ketones such as acetone and methyl ethyl ketone, aromatic hydrocarbons such as benzene, toluene, chlorobenzene and bromobenzene, aliphatic hydrocarbons such as petroleum ether, hexane and cyclohexane, sulfones such as sulfolane, and mixtures of these. Among such usable solvents, preferred are halogenated hydrocarbons such as methylene chloride and chloroform, ethers such as diethyl ether and tetrahydrofuran and organic nitriles such as acetonitrile and propionitrile. Especially preferred are diethyl ether, methylene chloride and acetonirile, among others. When such an organic solvent is used, the reaction is generally carried out by mixing compound [II]B with compound [III]B in the organic solvent and mixing the mixture with a base at below about 30° C., by mixing compound [II]B with a base in the organic solvent and mixing the mixture with compound [III]B at below about 30° C., or by by mixing a salt of compound [II]B and a base such as mentioned above with compound [III]B in the organic solvent at below about 30° C. Compound [III]B is used generally in an amount of 0.8 to 1.2 moles, preferably 0.95 to 1.05 moles, per mole of compound [II]B. Stoichiometrically, 2 moles of the base is required per mole of compound [II]B, since the reaction yields 2 moles of a hydrogen halide per mole of compound [II]B and the hydrogen halide forms a salt with the base. However, the base is used, unless the reaction is adversely affected, in an amount of 1.6 to 2.4 moles, preferably 1.8 to 2.2 moles, per mole of compound [II]B. When an organic solvent is used, it is used in an amount of 0.1 to 20 liters, preferably 0.5 to 10 liters, per mole of compound [II]B. The reaction temperature is desired to be low and is generally about 30° C. or below since higher temperatures tend to cause easy formation of byproducts. Considering the yields of byproducts and the extent of cooling realizable in the commercial practice, it lies generally within the range of 30° C. to −100° C. When the purity and yield of the desired product and the efficiency of cooling are taken into consideration, it is advantageous from the industrial viewpoint to carry out the reaction at a temperature within the range of 10° C. to −50° C., more preferably −10° C. to −30° C. The reaction is exothermic and vigorous in the step of mixing compound [II]B with compound [III]B in the presence of a base and therefore it is advisable to perform the mixing portionwise under cooling. The reaction time is several minutes to several hours depending on the efficiency of cooling and other factors. Furthermore, since the starting compound [III]B and the product [I]B can easily react with water, it is preferable that the starting materials and solvent to be used contain only a minimal amount of water and it is also preferable to conduct the reaction under protection from moisture.

The product [I]B produced by the reaction may be used in the form of a reaction mixture. As necessary, the reaction mixture containing [I]B is stored at a low temperature, namely at below about 30° C., preferably at 10° C. to −50° C., under protection from moisture, since, in the presence of a base or hydrochloride thereof, [I]B is unstable at higher temperatures and furthermore can easily react with water. If desired, [I]B can easily be isolated from the reaction mixture, for example by removing the hydrohalide salt of the base (precipitate) by filtration or other means with or without adding to the reaction mixture a hydrogen halide or a solvent in which the salt of the base and hydrogen halide as yielded by the reaction is sparingly soluble but [I]B is readily soluble, adequately selected from among ether, benzene, methylene chloride, acetonitrile, ethyl acetate, etc., and then concentrating the filtrate or the like. The thus-obtained [I]B may further be purified by distillation, crystallization or other purification procedures.

The starting compound [III]B to be used in the method of the preparation can easily be prepared, for example by reacting a compound of the formula R—H (R being as defined above) with a phosphorus oxyhalide or a diphosphoryl tetrahalide [Mizuma et al., Yakugaku Zasshi, 81, 51-52 (1961) and H. Grunze, Chem. Ber., 92, 850-854 (1959)] or by using a modification of such reaction.

Thus, in accordance with the method of the preparation, the desired product [I]B can be produced in high purity and good yield in one step under mild conditions in a short period of time from raw materials which can be handled with ease in industrial operations and are inexpensive. Therefore, the method of the preparation is an industrially very advantageous method for the production of [I]B.

REFERENCE EXAMPLE 1

Pyrocatechol (1.691 g, 15.36 mM) was dissolved in 60 ml of ether. Triethylamine (3.109 g, 30.72 mM) was added dropwise. The dropping funnel was washed with 10 ml of ether. The mixture, together with the washings, was stirred, and 2.287 g (15.36 mM) of methyl dichlorophosphate was added dropwise with cooling at −40° C. to −35° C. The dropping funnel was washed with 10 ml of ether and the mixture, together with the washings, was stirred at the same temperature for 10 minutes. The cooling bath was then removed and, after the temperature returned to room temperature (20°-25°

C.), the reaction mixture was place in a glass filter and filtered under a nitrogen pressure. The residue on the filter was washed with two 15-ml portions of ether. The filtrate and washings were concentrated under reduced pressure on a water bath at 20° C. There was obtained 1.847 g (96.0% yield) of methyl o-phenylene phosphate as a colorless viscous oil. Upon standing in a refrigerator, it crystallized.

NMR (CDCl$_3$)δ: 3.82 and 4.03 (3H, each s, P—OCH$_3$), 7.09

(4H, s, 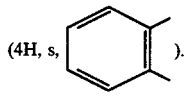 ).

Signals for trace amounts of ether and triethylamine were also observed. R$_f$ in TLC: 0.31 (Kieselgel) 60F-254, acetonitrile:water:99% formic acid=220:20:1).

REFERENCE EXAMPLE 2

Pyrocatechol (1.249 g, 11.35 mM) was dissolved in 42 ml of ether and, using 2.297 g (22.70 mM) of triethylamine and 1.849 g (11.35 mM) of ethyl dichlorophosphate, the reaction was carried out at −40° C. to −35° C. and the reaction mixture treated in the same manner as in Reference Example 1. There was obtained 2.159 g (95.0% yield) of ethyl o-phenylene phosphate as a colorless viscous oil.

NMR(CDCl$_3$)δ: 1.42 (3H, t, J=7 Hz, C—CH$_3$), 4.23 and 4.40 (2H, each q, J=7 Hz, P—O—CH$_2$), 7.08

(4H, s, 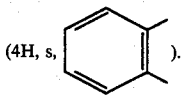 ).

Signals for trace amounts of ether and triethylamine were also observed. R$_f$ in TLC: 0.36 (under the same conditions as in Reference Example 1).

REFERENCE EXAMPLE 3

Pyrocatechol (0.993 g, 9.02 mM) was dissolved in 50 ml of ether and, using 1.825 g (18.04 mM) of triethylamine and 1.723 (9.02 mM) of n-butyl dichlorophosphate, the reaction was carried out at −5° C. to 0° C. and the reaction mixtured treated in the same manner as in Reference Example 1. There was obtained 1.914 g (93.0% yield) of n-butyl o-phenylene phosphate as a colorless viscous oil.

$^1$H-NMR(CDCl$_3$)δ: 0.7~2.0 (5H, m, C—CH$_2$CH$_2$CH$_3$), 4.13 and 4.28 (2H, each t, J=6.5 Hz, P—O—CH$_2$), 7.10

(4H, s, 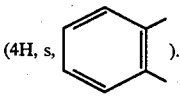 ).

Signals for trace amounts of ether and triethylamine were also observed. R$_f$ in TLC: 0.45 (under the same conditions as in Reference Example 1).

REFERENCE EXAMPLE 4

Pyrocatechol (0.856 g, 7.77 mM) was dissolved in 32 ml of ether and, using 1.573 g (15.54 mM) of triethylamine and 1.484 g (7.77 mM) of n-propyl dichlorophosphate, the reaction was carried out at −30° C. to −25° C. and the reaction mixture treated in the same manner as in Reference Example 1. There was obtained 1.695 g (95.6% yield) of n-propyl o-phenylene phosphate as a viscous oil (slightly turbid).

NMR (CDCl$_3$)δ: 0.97 (3H, t, J=7 Hz, C—CH$_3$), 1.77 (2H, q, J=7×7.5 Hz, O—C—CH$_2$), 4.15 and 4.29 (2H, each q, J=7.5 Hz, P—O—CH$_2$), 7.08

(4H, s, 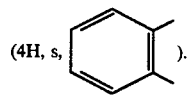 ).

Signals for trace amounts of ether and triethylamine were also observed. R$_f$ in TLC: 0.41 (under the same conditions as in Reference Example 1).

REFERENCE EXAMPLE 5

Triethylamine (2.211 g, 21.86 mM) was added to a solution of 1.989 g (10.93 mM) of ethyl 3,4-dihydroxybenzoate in 30 ml of ether. The mixture was cooled to −30° C. to −20° C. and a solution of 1.627 g (10.93 mM) of methyl dichlorophosphate in 10 ml of ether was added thereto dropwise with stirring over 10 minutes. The reaction mixture was stirred at the same temperature for 5 minutes, the bath was then removed and the temperature was allowed to rise to 20° C. Filtration and washing were carried out by the procedure of Reference Example 1, and the filtrate and washings were concentrated at room temperature (20°~25° C.) under reduced pressure. There was obtained 2.387 g (84.6% yield) of 5-ethoxycarbonyl-2-methoxy-2-oxo-1,3,2-benzo-dioxaphosphole as a viscous oil.

NMR (CH$_2$Cl$_2$)δ: 1.26 (3H, t, J=7 Hz, C—CH$_3$), 3.84 and 4.05 (3H, each s, P—O—CH$_3$), 4.34 (2H, q, J=7 Hz, C—CH$_2$), 7.0~8.0

(3H, m, 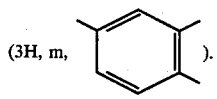 ).

Signals for CH$_2$Cl$_2$ and a trace amount of ether were also observed. R$_f$ in TLC: 0.38 (under the same conditions as in Reference Example 1).

REFERENCE EXAMPLE 6

3,4-Dihydroxytoluene (1.686 g, 13.58 mM) was dissolved in 40 ml of ether and, using 2.748 g of triethylamine and 2.022 g of methyl dichlorophosphate, the reaction mixture was treated in the same manner as in Reference Example 5. There was obtained 2,400 g (88.4% yield) of 2-methoxy-5-methyl-2-oxo-1,3,2-benzodioxaphosphole as a viscous oil.

NMR (CH$_2$Cl$_2$)δ: 2.32 (3H, s, C—CH$_3$), 3.78 and 3.99 (3H, each s, P—O—CH$_3$), 6.8~7.1

(3H, m, 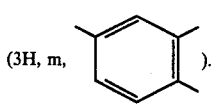 ).

Signals for CH$_2$Cl$_2$ and a trace amount of ether were also observed. R$_f$ in TLC: 0.31 (under the same conditions as in Reference Example 1).

REFERENCE EXAMPLE 7

2,3-Dihydroxynaphthalene (1.747 g, 10.91 mM) was dissolved in 40 ml of ether and, using 2.208 g of triethylamine and 1.625 g of methyl dichlorophosphate, the porcedure of Reference Example 5 was followed to give 2.20 g (85.4% yield) of 6-benzo-2-methoxy-2-oxo-1,3,2-benzodioxaphosphole as a white powder.

NMR (CH$_2$Cl$_2$)δ: 3.82 and 4.03 (3H, each s, P—OCH$_3$), 7.1~7.9

(6H, m, 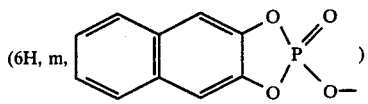 )

R$_f$ in TLC: 0.30 (under the same conditions as in Reference Example 1).

REFERENCE EXAMPLE 8

To 1.180 g (10.72 mM) of pyrocatechol were added 11 ml of methylene chloride and 1.596 g of methyl dichlorophosphate, the mixture was stirred at room temperature (20°-25° C.) for 20 minutes and then cooled to −30° C. Thereto was added 2.169 g of triethylamine dropwise with stirring at −30° C. to −20° C. over 7 minutes. The dropping funnel was washed with 1 ml of methylene chloride and the washings were added to the mixture. The reaction mixture was stirred at the same temperature for 15 minutes. and, after it returned to 10° C., filtered to remove the triethylamine hydrochloride precipitate, which was washed with methylene chloride. The filtrate and washings were analyzed by NMR spectrometry, by which it was revealed that the yield of methyl o-phenylene phosphate as found in the filtrate and washings was 89%.

NMR (CH$_2$Cl$_2$)δ: 3.81 and 4.02 (3H, each s, P—OCH$_3$), 7.16

(4H, s, 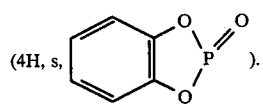 ).

Signals due to the presence of CH$_2$Cl$_2$ and triethylamine hydrochloride as well as a weak signal (multiplet) at 6.2-7.6 ppm due to

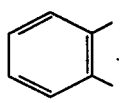

The yield of the desired product was calculated based on the ratio (89%) between the signal (7.16 ppm) of

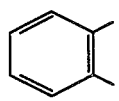

of the desired product and the signal in the 6.2-7.6 ppm region.

REFERENCE EXAMPLE 9

To 0.710 g (6.45 mM) of pyrocatechol was added 7 ml of methylene chloride. Then, 0.960 g of methyl dichlorophosphate and 1 ml of methylene chloride were added. The mixture was cooled to −15° C. to −10° C. with stirring and 2.390 g of tri-n-butylamine was added dropwise thereto over 8 minutes. The dropping funnel was washed with 3 ml of methylene chloride and the washings were added to the reaction mixture. The mixture was stirred at the same temperature for 5 minutes and then allowed to return to 10° C. Analysis of the liquid reaction mixture by NMR spectrometry indicated that the yield of methyl o-phenylene phosphate was 89%.

NMR (CH$_2$Cl$_2$)δ: 3.81 and 4.02 (3H, each s, P—OCH$_3$), 7.14

(4H, s, 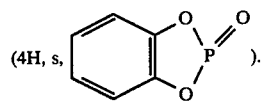 ).

Signals due to the presence of CH$_2$Cl$_2$ and tributylamine hydrochloride as well as a weak signal (multiplet) at 6.2-7.6 ppm due to

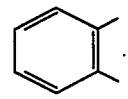

The yield of the desired product was determined in the same manner as in Reference Example 8.

REFERENCE EXAMPLE 10

The procedure of Reference Example 9 was followed using di-n-butylamine or phridine in place of tri-n-butylamine, the yield of methyl o-phenylene phosphate in the liquid reaction mixture as determined in the same manner as in Reference Example 9 being 71% or 91%, respectively.

REFERENCE EXAMPLE 11

To 1.418 g of pyrocatechol were added 1.917 g of methyl dichlorophosphate and 11 ml of acetonitrile. The mixture was cooled to −25° C. and 2.605 g of triethylamine was added dropwise at −25° C. to −20° C. with stirring. The dropping funnel was washed with 1 ml of acetonitrile and the washings were added to the mixture. After stirring at the same temperature for 10 minutes, the reaction mixture was allowed to return to 10° C. and then filtered. The filtration residue was washed with a 5-ml and 3-ml portion of acetonitrile. The filtrate and washings were concentrated under reduced pressure on a water bath at 15° C. to 20° C. to give 3.102 g of methyl o-phenylene phosphate as a slightly turbid oil.

NMR (CH$_2$Cl$_2$)δ: 3.81 and 4.01 (3H, each s, P—OCH$_3$), 7.12

(4H, s, 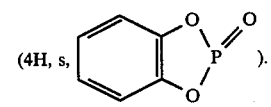 ).

Signales for contaminants, CH$_2$Cl$_2$ and triethylamine hydrochloride (about 0.25 mole per mole of the desired product), were also obserbed.

REFERENCE EXAMPLE 12

To 0.963 g of pyroacatechol were added 7 ml of methylene chloride and 1.30 g of methyl dichlorophosphate. The mixture was stirred at room temperature (20°–25° C.) for 10 minutes and then, with cooling to −20° C. to −15° C., 1.86 g of triethylamine was added dropwise. The dropping funnel was washed with 1 ml of methylene chloride and the washings were added to the mixture. The resulting mixture was stirred at the same temperature for 5 minutes to give a reaction mxiture containing methyl o-phenylene phosphate and triethylamine hydrochloride.

REFERENCE EXAMPLE 13

To a solution of 3.11 g of phenylphosphonic acid dichloride in 10 ml of ether were added 1.76 g of pyrocatechol and 20 ml of ether. The resulting solution was cooled to −25° C. to −28° C. and a solution of 3.23 g of triethylamine in 10 ml of ether was added dropwise thereto with stirring over 8 minutes. Thereafter, the reaction mixture was allowed to return to room temperature (20°–25° C.), and the precipitate was filtered off under nitrogen atmosphere and washed with 30 ml of ether. The filtrate and washings were combined and the ether was distilled off under reduced pressure to give 3.46 g (94.4% yield) of 2-phenyl-2-oxo-1, 3,2-benzodioxaphosphole as a colorless oil. Upon standing in a refrigerator overnight, it crystallized.

NMR (CDCl$_3$)δ: 7.11

(4H, s, 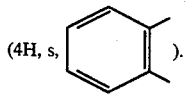 ).

7.2~8.1

(5H, m, 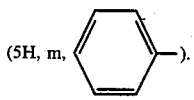 ).

Signals for a trace amount of ether were also observed. R$_f$ in TLC: 0.35 (under the same conditions as in Reference Example 1).

REFERENCE EXAMPLE 14

A solution of 1.75 g of 7β-(D-5-carboxy-5-phthalimidovaleramido)-3-hydroxymethyl-3-cephem-4-carboxylic acid di-tri-n-butylamine salt and 0.35 g of 5-mercapto-1-methyl-1H-tetrazole in 20 ml of methylene chloride was cooled to −25° C., 0.74 g of methyl o-phenylene phosphate was added thereto, and the mixture was stirred at −25° C. to −20° C. for 2 hours. To the reaction mixture, there were added 15 ml of tetrahydrofuran and 15 ml of water, followed by adequate stirring and phase separation. The aqueous layer was extracted with 5 ml of tetrahydrofuran and 10 ml of methylene chloride. The organic layers were combined, washed with 20 ml of water, and dried over anhydrous magnesium sulfate. The solvents were distilled off under reduced pressure, and the residue was dissolved in a small amount of acetone and the solution was added to 100 ml of ether. The resulting precipitate was collected by filtration, washed with ether and dried in vacuo to give 1.14 g (94.7% yield) of 7β-(D-5-carboxy-5-phthalimidovaleramido)-3-(1-methyl-1H-tetrazol-5-yl)thiomethyl-3-cephem-4-carboxylic acid.

IR (KBr)cm$^{-1}$: 3340, 2950, 1775, 1715, 1534, 1394.

NMR (DMSO-d$_6$)δ: 1.40~2.40 (6H, m, —(CH$_2$)$_3$—), 3.62 (2H, broad, 2-CH$_2$), 3.94 (3H, s, N—CH$_3$), 4.30 (2H, ABq, J=15 Hz, 3—CH$_2$), 4.73 (1H, t, J=8 Hz, >CH—), 5.01 (1H, d, J=5 Hz, 6—H), 5.62 (1H, q, J=5&8 Hz, 7—H), 7.91

(4H, s, 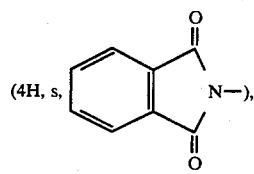 N—), 8.77 (1H, d, J=8 Hz, —CONH—).

REFERENCE EXAMPLE 15

A solution of 3.52 g of 7β-(D-5-carboxy-5-phthalimidovaleramido)-3-hydroxymethyl-3-cephem-4-carboxylic acid ditriethylamine salt and 1.00 g of 5-mercapto-1-methyl-1H-tetrazole in 25 ml of methylene chloride was cooled to −20° C., and 0.25 g of triethylamine was added thereto with stirring. To this solution was added the whole reaction prepared in Reference Example 12 dropwise with stirring at −20° C. to −15° C. The dropping funnel was washed with 6 ml of methylene chloride and the washings were added to the reaction mixture. The mixture was stirred at the same temperature for 20 minutes and then at −5° C. to 0° C. for 60 minutes. Following addition of 10 ml of water to the reaction mixture, the solvent was distilled off under reduced pressure, and a new 30-ml portion of methylene chloride and 15 ml of tetrahydrofuran were added to the residue. After phase separation, the organic layer was washed with 1N hydrochloric acid and then with saturated aqueous solution of sodium chloride, and dried over magnesium sulfate. The solvents were distilled off under reduced pressure, the residue was dissolved in a small amount of acetone, the solution was poured into ether, and the resulting precipitate was collected by filtration, washed with ether and dried in vacuo to give 2.82 g (93.8% yield) of the same product as obtained in Reference Example 14. The IR and NMR spectra for this product confirmed the identity thereof with the substance obtained in Reference Example 14.

The present invention is illustrated in further detail below with Examples, but it is to be understood that the examples are solely for the purpose of illustration and not to be construed as limitations of the invention, and that many variations may be resorted to without departing from the spirit and scope of the invention.

In the Reference Examples and Examples, the elution in column chromatography was carried out with observation of TLC (Thin Layer Chromatography). In the TLC, were employed Merck pre-coated TLC plate 60F$_{254}$ and UV lamp for detection.

For silica gel chromatography, "silica gel 60 for column chromatography "manufactured by E. Merck in Germany was used. The resin named "Amberlite XAD-2" is a product manufactured by Rohm & Haas Co. in U.S.A. All the temperatures are uncorrected and the expression "room temperature" means 20°–25° C. The percentages are all on weight basis, except the cases of solvents. In those cases, the percentages are all on volume basis. The NMR spectra given therein were measured using a Varian Model EM 390 (90 MHz) or Hitachi Perkin-Elmer R-20 spectrometer with tetramethylsilane or sodium 2,2-dimethyl-2-silapentane-5-sulfonate as the internal or external reference and all δ values are in ppm. The symbol s stands for a singlet, d a doublet, q a quarter, ABq a AB type quartet, t a triplet, dd a double doublet, m a multiplet, br broad and J a coupling constant. Infrared (IR) spectra were recorded on a Hitachi EPI-S2 spectrometer. And, symbols in Examples and Reference Examples have the following meanings, respectively;

mg: milligram
g: gram
ml: milliliter
%: percent
mM: millimole
Hz: Herz
°C.: centigrade degree
NMR: Nuclear Magnetic Resonance absorption
IR: Infra-Red absorption
DMSO: dimethysulfoxide
D$_2$O: heavy water
v/v: volume per volume
THF: tetrahydrofuran
TLC: Thin layer chromatography

EXAMPLE 1

To 0.70 g of 5-mercapto-1-methyl-1H-tetrazole were added 30 ml of methylene chloride and 0.61 g of triethylamine and 1.14 g of o-phenylene phosphorochloridate was added at room temperature (20°-25° C.). The solution was cooled to −60° C. and a solution of 2.12 g of 7β-(D-5-carboxy-5-phthalimidovaleramido)-3-hydroxymethyl-3-cephem-4-carboxylic acid ditriethylamine salt in 10 ml of methylene chloride was added all at once. The mixture was once warmed to 15° C. and, then, cooled, and 20 ml of tetrahydrofuran (THF) and 20 ml of water were added. After phase separation, the aqueous layer was extracted with 5 ml of THF and 10 ml of methylene chloride. The organic layer and the extract were combined, dried with anhydrous magnesium sulfate, concentrated to about 10 ml under reduced pressure, and added to 100 ml of ether. The precipitate was collected by filtration, washed with ether and dried in vacuo to give 1.33 g (yield 73.7%) of 7β-(D-5-carboxy-5-phthalimidovaleramido)-3-(1-methyl-1H-tetrazol-5-yl)thiomethyl-3-cephem-4-carboxylic acid.

IR (KBr) cm$^{-1}$; 3340, 2950, 1775, 1715, 1534, 1394.

NMR (DMSO—d$_6$); δ 1.40∼2.40 (6H, m, —(CH$_2$)$_3$—), 3.62 (2H, br, 2—CH$_2$) 3.94 (3H, s, >N—CH$_3$), 4.30 (2H, ABq, J=15 Hz, 3—CH$_2$), 4.73 (1H, t, J=8 HZ, >CH—), 5.01 (1H, d, J=5 Hz, 6—H), 5.62 (1H, q, J=5 & 8 Hz, 7—H), 7.91

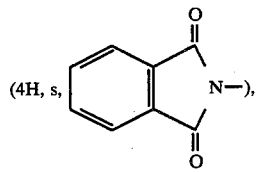

(4H, s,                N—), 8.77 (1H, d, J=8 Hz, —CONH—).

EXAMPLE 2

To 1.04 g of 1-(2-dimethylaminoethyl)-5-mercapto-1H-tetrazole were added 60 ml of methylene chloride and 0.61 g of triethylamine, and 1.14 g of o-phenylene phosphorochloridate was added at room temperature.

The mixture was cooled to −60° C. and a solution of 2.12 g of 7β-(D-5-carboxy-5-phthalimidovaleramido)-3-hydroxymethyl-3-cephem-4-carboxylic acid ditriethylamine salt in 10 ml of methylene chloride was added all at once. The mixture was warmed to 15° C. and the precipitate was collected by filtration and washed with methylene chloride. The solid substance was suspended in 30 ml of methylene chloride and 0.71 g of triethylamine was added under ice-cooling. The suspension was stirred for 30 minutes and the insoluble matter was filtered off. Then, at 0° C. or below, 10 ml of 1N ethanolic hydrochloric acid and 20 ml of ether were added dropwise to the filtrate. The precipitate was collected by filtration, washed with methylene chloride and dried in vacuo to give 1.51 g (yield 72.4%) of 7β-(D-5-carboxy-5-phthalimidovaleramido)-3-[1-(2-dimethylaminoethyl)-1H-tetrazol-5-yl]-thiomethyl-3-cephem-4-carboxylic acid hydrochloride.

IR (KBr) cm$^{-1}$; 1775, 1715, 1640.

NMR (DMSO—d$_6$); δ 1.30-2.40 (6H, m, —(CH$_2$)$_3$—), 2.83

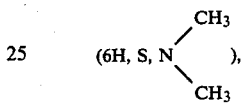

(6H, S, N(CH$_3$)(CH$_3$) ), 3.5∼3.8 (4H, m, 2—CH$_2$ & —CH$_2$N<), 4.30 (2H, br, 3—CH$_2$), 4.5∼4.9 (3H, m, —CH< & =N>$^{N-CH2}$), 5.0 (1H, d, J=5 Hz, 6—H), 5.60 (1H, q, J=5 and 8 Hz, 7—H), 7.90

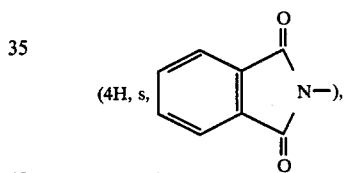

(4H, s,               N—), 8.77 (1H, d, 8 Hz, —CONH—).

EXAMPLE 3

To a mixture of 2.12 g of 7β-(D-5-carboxy-5-phthalimidovaleramido)-3-hydroxymethyl-3-cephem-4-carboxylic acid ditriethylamine salt and 0.52 g of 5-mercapto-1-methyl-1H-tetrazole were added 30 ml of methylene chloride and 0.61 g of triethylamine, and the resultant solution was cooled to −15° C. To this solution was added 1.67 g of methyl o-phenylene phosphate and the reaction was allowed to proceed at −15° C. to −10° C. for 30 minutes. To the reaction mixture were added 20 ml of THF and 20 ml of water and the whole mixture was adjusted to pH 2 with 6N-hydrochloric acid. After phase separation, the aqueous layer was extracted with 5 ml of THF and 10 ml of methylene chloride. The organic layer and the extract were combined and dried over anhydrous magnesium sulfate.

The above product was further treated as in Example 1 to give 1.64 g (yield 90.9%) of the desired product. The IR and NMR spectra of this product were identical with those of the compound obtained in Example 1.

EXAMPLE 4

To a solution of 1.71 g of o-phenylene phosphorochloridate in 15 ml of methylene chloride was added 0.91 g of triethylamine. Then, at room temperature, 0.29 g of methanol was added and the reaction was allowed to proceed at room temperature for 10 minutes. Using the thus-obtained methyl o-phenylene phosphate solution in place of 1.67 g of methyl o-phenylene phosphate, the reaction and after-treatment were carried out in the same manner as Example 3 to give 1.62 g (yield 89.8%) of the desired product. The IR spectrum of this product was identical with that of the compound obtained in Example 1.

EXAMPLE 5

A solution of 1.75 g of 7$\beta$-(D-5-carboxy-5-phthalimidovaleramido)-3-hydroxymethyl-3-cephem-4-carboxylic acid ditri-n-butylamine salt and 0.35 g of 5-mercapto-1-methyl-1H-tetrazole in 20 ml of methylene chloride was cooled to $-20°$ C. To this solution was added 0.74 g of methyl o-phenylene phosphate and the reaction was allowed to proceed at $-25°$ to $-20°$ C. for 2 hours. To the reaction mixture were added 15 ml of THF and 15 ml of water and the whole mixture was thoroughly stirred and allowed to stand for phase separation. The aqueous layer was extracted with 5 ml of THF and 10 ml of $CH_2Cl_2$. The organic layer and the extract were combined, washed with 20 ml of water and dried over anhydrous magnesium sulfate. The solvent was then distilled off under reduced pressure and the residue was dissolved in a small amount of acetone and added to 100 ml of ether. The precipitate was collected by filtration, washed with ether and dried in varuo to give 1.14 g (yield 94.7%) of the desired product. The IR spectrum of this product was identical with that of the compound obtained in Example 1.

EXAMPLE 6

To 0.52 g of 1-(2-dimethylaminoethyl)-5-mercapto-1H-tetrazole were added 40 ml of methylene chloride and 0.40 g of triethylamine, followed by addition of 1.41 g of 7$\beta$-(D-5-carboxy-5-phthalimidovaleramido)-3-hydroxymethyl-3-cephem-4-carboxylic acid ditriethylamine salt. To the mixture was added 1.12 g of methyl o-phenylene phosphate and the reaction was allowed to proceed at 20°-25° C. for 10 minutes. The reaction mixture was cooled, and 5 ml of 1N ethereal hydrochloric acid was added dropwise at 0° C. or below. The precipitate was collected by filtration and washed with methylene chloride. The solid matter was suspended in 20 ml of methylene chloride and 0.47 g triethylamine was added under ice-cooling. The mixture was stirred for 30 minutes and the insoluble matter was filtered off. Then, at 0° C. or below, 6.7 ml of 1N alcoholic hydrochloric acid and 10 ml of ether were added dropwise to the filtrate. The precipitate was collected by filtration, washed with methylene chloride and dried in vacuo to give 1.00 g (yield 71.9%) of the desired product. The IR and NMR spectra of this compound were identical with those of the compound obtained in Example 2.

EXAMPLE 7

In 10 ml of methylene chloride was dissolved 0.76 g of o-phenylene phosphorochloridate, followed by addition of 0.40 g triethylamine. Then, at room temperature, 0.56 g of p-nitrophenol was added portionwise, and the reaction was allowed to proceed at room temperature for 10 minutes. The reaction mixture was added to a solution cooled to $-20°$ C. of 1.41 g of 7$\beta$-(D-5-carboxy-5-phthalimidovaleramido)-3-hydroxymethyl-3-cephem-4-carboxylic acid ditriethylamine salt, 0.35 g of 5-mercapto-1-methyl-1H-tetrazole and 0.20 g of triethylamine in 20 ml of methylene chloride, and the reaction was allowed to proceed at $-20°\pm2°$ C. for 20 minutes. The reaction mixture was further treated in the same manner as Example 3 to give 0.911 g (yield 75.7%) of the desired product. The IR spectrum of this product was identical with that of the compound obtained in Example 1.

EXAMPLE 8

In 10 ml of methylene chloride was dissolved 0.74 g of 2,2,2-trichloro-1,3,2-benzodioxaphosphole, followed by addition of 0.30 g of triethylamine. Then, at room temperature, 0.10 g of methanol was added and the reaction was allowed to proceed at room temperature for 10 minutes. The reaction mixture was ice-cooled, and 0.20 g of triethylamine, 0.17 g of 5-mercapto-1-methyl-1H-tetrazole and 0.71 g of 7$\beta$-(D-5-carboxy-5-phthalimidovaleramido)-3-hydroxymethyl-3-cephem-4-carboxylic acid ditriethylamine salt were added in that order. The reaction was allowed to proceed under ice-cooling for 30 minutes. The reaction mixture was treated in the same manner as described in Example 3 to give 0.404 g of (yield 66.8%) of the desired product. The IR spectrum of this product was identical with that of the compound obtained in Example 1.

EXAMPLE 9

In 10 ml of methylene chloride was dissolved 0.74 g of 2,2,2-trichloro-1,3,2-benzodioxaphosphole, followed by addition of 0.4 g of triethylamine. Then, at room temperature, 0.51 g of p-chlorophenol was added portionwise, and 0.2 g of triethylamine, 0.17 g of 5-mercapto-1-methyl-1H-tetrazole and 0.71 g of 7$\beta$-(D-5-carboxy-5-phthalimidovaleramido)-3-hydroxymethyl-3-cephem-4-carboxylic acid ditriethylamine salt were added in that order. The reaction was allowed to proceed at room temperature for 40 minutes. The reaction mixture was further treated in the same manner as described in Example 3 to give 0.436 g (yield 72.0%) of the desired product. The IR spectrum of this product was identical with that of the compound obtained in Example 1.

EXAMPLE 10

In 10 ml of methylene chloride was dissolved 1.13 g of bis(o-phenylenedioxo)chlorophosphorus and, under ice-cooling, 0.2 g of triethylamine, 0.17 g of 5-mercapto-1-methyl-1H-tetrazole and 0.71 g of 7$\beta$-(D-5-carboxy-5-phthalimidovaleramido)-3-hydroxymethyl-3-cephem-4-carboxylic acid ditriethylamine salt were added in that order. The reaction was allowed to proceed under ice-cooling for 30 minutes. The reaction mixture was further treated in the same manner as described in Example 3 to give 0.43 g of the desired product. The IR spectrum of this product was identical with that of the compound obtained in Example 1.

EXAMPLE 11

In 5 ml of methylene chloride was dissolved 0.71 g of 7$\beta$-(D-5-carboxy-5-phthalimidovaleramido)-3-hydroxymethyl-3-cephem-4-carboxylic acid ditriethylamine salt and 0.17 g of 5-mercapto-1-methyl-1H-tetrazole. To this solution were added 0.2 g of triethylamine and 0.51 g of methyl o-phenylene phosphite and the reaction was allowed to proceed at room temperature for 22 hours. The reaction mixture was further treated in the same manner as described in Example 3 to give 0.41 g (yield 67.7%) of the desired product. The IR and NMR spectra of this product were identical with those of the compound obtained in Example 1.

EXAMPLE 12

A solution of 874 mg of 7β-(D-5-carboxy-5-phthalimidovaleramido)-3-hydroxymethyl-3-cephem-4-carboxylic acid ditri-n-butylamine salt and 251 mg of 2-mercaptobenzothiazole in 10 ml of methylene chloride was cooled to −10° C., and 400 mg of ethyl o-phenylene phosphate was added. The mixture was stirred at −10° C. to −5° C. for 2 hours. To the reaction mixture were added 8 ml of THF and 8 ml of water and the whole mixture was stirred and allowed to stand for phase separation. The aqueous layer was extracted with 5 ml of methylene chloride, and the organic layer and the extract were combined, followed by addition of 10 ml of water. After phase separation, the organic layer was dried over anhydrous magnesium sulfate. The solvent was then distilled off under reduced pressure and the residue was dissolved in a small amount of a mixture of acetonitrile, water and formic acid (20:2:0.1) and subjected to silica gel column chromatography. The fractions ($R_f$: about 0.43) containing the desired product were collected and concentrated under reduced pressure. To the oily residue was added ether and the resultant powder was collected by filtration, washed with ether and dried to give 555 mg (yield 85.0%) of 7β-(D-5-carboxy-5-phthalimidovaleramido)-3-[(benzothiazol-2-yl)thiomethyl]-3-cephem-4-carboxylic acid.

IR(KBr) cm$^{-1}$: 3320, 1775, 1715.

NMR(DMSO—d$_6$): δ 1.30~2.40(6H, m, —CH$_2$CH$_2$CH$_2$—), 3.62(2H, ABq, J=18 Hz, 2—CH$_2$), 4.38(2H, ABq, J=14 Hz, 3—CH$_2$), 4.73(1H, t, J=7 Hz, >CH—), 5.04(1H, d, J=5 Hz, C$_6$—H), 5.63 (1H, q, J=5&8 Hz, C$_7$—H) 7.86

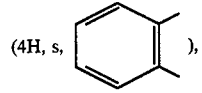

8.80(1H, d, J=8 Hz, —COHN—).

EXAMPLE 13

A solution of 874 mg of 7β-(D-5-carboxy-5-phthalimidovaleramido)-3-hydroxymethyl-3-cephem-4-carboxylic acid ditri-n-butylamine salt and 198 mg of 5-mercapto-2-methyl-1,3,4-thiadiazole in 10 ml of methylene chloride was cooled to −20° C. to −15° C. To this solution was added 375 mg of methyl o-phenylene phosphate and the mixture was stirred under ice-cooling for 1.5 hours. The reaction mixture was further treated in the same manner as Example 12 to give 502 mg (yield 81.3%) of 7β-(D-5-carboxy-5-phthalimidovaleramido)-3-[(2-methyl-1,3,4-thiadiazol-5-yl)thiomethyl]-3-cephem 4-carboxylic acid.

IR(KBr) cm$^{-1}$: 3300, 1775, 1715.

NMR(DMSO—d$_6$): δ 1.30~2.40(6H, m, —CH$_2$CH$_2$CH$_2$—), 2.21(3H, s, —CH$_3$), 3.62(2H, ABq, J=19 Hz, 2—CH$_2$), 4.37(2H, ABq, J=13 Hz, 3—CH$_2$), 4.76(1H, t, J=7 Hz, >CH—), 5.06(1H, d, J=5 Hz, C$_6$—H), 5.65(1H, q, J=5&8 Hz, C$_7$—H).

EXAMPLE 14

A solution of 477 mg of o-phenylene phosphorochloridate in 5 ml of methylene chloride was cooled to −20° C. to −10° C. To the solution were added 463 mg of tri-n-butylamine and 235 mg of phenol and the mixture was stirred at the same temperature for 5 minutes to make a phenyl o-phenylene phosphate solution. On the other hand, with stirring and ice-cooling, 278 mg of tri-n-butylamine was added to a solution of 874 mg of 7β-(D-5-carboxy-5-phthalimidovaleramido)-3-hydroxymethyl-3-cephem-4-carboxylic acid ditri-n-butylamine salt and 312 mg of 2-carboxymethylthio-5-mercapto-1,3,4-thiadiazole in 5 ml of methylene chloride. The mixture was cooled to −10° C. to −5° C. and the above-mentioned phenyl o-phenylene phosphate solution was added. The whole mixture was stirred at room temperature for 2 hours. The reaction mixture was treated further in the same manner as Example 12 to give 501 mg (yield 72.2%) of 7β-(D-5-carboxy-5-phthalimidovaleramido)-3-[(2-carboxymethylthio-1,3,4-thiadiazole-5-yl)thiomethyl]-3-cephem-4-carboxylic acid.

IR(KBr) cm$^{-1}$: 3300, 1775, 1713.

NMR(DMSO—d$_6$): δ 1.30~2.40(6H, m, —CH$_2$CH$_2$CH$_2$—), 3.59(2H, br, 2—CH$_2$), 4.13(2H, s, —SCH$_2$COO—), 4.33(2H, ABq, J=13 Hz, 3—CH$_2$), 4.72

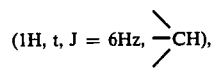

5.04(1H, d, J=5 Hz, C$_6$—H), 5.40~5.80(1H, br, C$_7$—H), 7.90

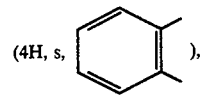

8.78(1H, d, J=8 Hz, —CONH—).

EXAMPLE 15

To a mixture of 874 mg of 7β-(D-5-carboxy-5-phthalimidovaleramido)-3-hydroxymethyl-3-cephem-4-carboxylic acid ditri-n-butylamine salt and 312 mg of 1-carboxymethyl-5-mercapto-1H-tetrazole was added 10 ml of methylene chloride and 278 mg of tri-n-butylamine was added under ice-cooling. The mixture was stirred for 10 minutes, after which 372 mg of methyl o-phenylene phosphate was added at −25° to −20° C. and the whole mixture was stirred at the same temperature for 2 hours. The reaction mixture was further treated in the same manner as Example 12 to give 476 mg (yield 73.7%) of 7β-(D-5-carboxy-5-phthalimidovaleramido)-3-[(1-carboxymethyl-1H-tetrazol-5-yl)thiomethyl]-3-cephem-4-carboxylic acid.

IR(KBr) cm$^{-1}$: 3300, 1773, 1713.

NMR(DMSO—d$_6$): δ 1.40~2.40(6H, m, —CH$_2$CH$_2$CH$_2$—), 3.62(2H, br, 2—CH$_2$), 4.33 (2H, ABq, J=14 Hz, 3—CH$_2$), 4.71(1H, t, J=6 Hz, >CH—), 4.99(1H, d, J=5 Hz, C$_6$—H), 5.28(2H, s, >NCH$_2$CO—), 5.62(1H, q, J=5&8 Hz, C$_7$—H), 7.89

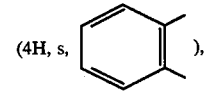

8.77(1H, d, J=8 Hz, —CONH—).

EXAMPLE 16

Using 354 mg of 2-ethoxycarbonylmethylthio-5-mercapto-1,3,4-thiadiazole in place of 2-mercaptobenzothiazole, the procedure of Example 12 was repeated to give 600 mg (yield 83.2%) of 7β-(D-5-carboxy-5-phthalimidovaleramido)-3-[(2-ethoxycarbonylmethylthio-1,3,4-thiadiazol-5-yl)thiomethyl]-3-cephem-4-carboxylic acid.

IR(KBr) cm$^{-1}$: 3320, 1775, 1715.

NMR(DMSO—d$_6$): δ 1.00~2.40(9H, m, —CH$_3$&—CH$_2$CH$_2$CH$_2$—), 2.9~4.5(8H, m, 2—CH$_2$, 3—CH$_2$, —S—CH$_2$CO—, CO$_2$CH$_2$), 4.75(1H, t, J=6 Hz, >CH—), 5.06(1H, d, J=5 Hz, C$_6$—H), 5.40~5.90(1H, br, C$_7$—H), 7.90

(4H, s, 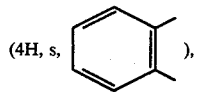 ), 8.60~9.10(1H, br, —CONH—).

EXAMPLE 17

In 10 ml of methylene chloride was dissolved 874 mg of 7β[D-5-carboxy-5-(benzamido)valeramido]-3-hydroxymethyl-3-cephem-4-carboxylic acid ditri-n-butylamine salt and, under cooling at −50° C. to −40° C., 198 mg of pyridine and a solution of 372 mg of methyl o-phenylene phosphate in 3 ml of methylene chloride were added in that order. Then, at −10° C. to 0° C., the mixture was stirred for 2 hours. To the reaction mixture was added 15 ml of water and the mixture was adjusted to pH 7.0 and allowed to stand for phase separation. The aqueous layer was washed twice with 5 ml portions of methylene chloride, adjusted again to pH 6.0 and concentrated under reduced pressure. The residue was subjected to Amberlite XAD-2 column chromatography (XAD-2 of 100–200 mesh: 100 ml, column height: 32 cm), elution being carried out with water and water-methanol (10:2). The fractions were checked by TLC (developing solvent: acetonitrile 15:water 5:99% formic acid 0.25) and the fractions (R$_f$: about 0.24) containing the desired product were pooled and concentrated to give 410 mg (yield 73.1%) of N-[7β-[D-5-(benzamido)adipinamido]-3-cephem-3-ylmethyl]pyridinium-4-carboxylic acid monosodium salt.

IR(KBr) cm$^{-1}$: 3360, 3250, 1765, 1645, 1630, 1605.

NMR(D$_2$O): δ 1.50~2.60(6H, m, —(CH$_2$)$_3$—), 3.14(2H, ABq, J=19 Hz, 2—CH$_2$), 4.36(1H, m, >CH—), 5.05(1H, d, J=5 Hz, C$_6$—H), 5.32(2H, ABq, J=15 Hz, 3—CH$_2$), 5.60(1H, d, J=5 Hz, C$_7$—H), 7.0~9.0

(10H, m, —N  )

EXAMPLE 18

To a solution of 286 mg of o-phenylene phosphorochloridate in 3 ml of methylene chloride was added 174 mg of 5-mercapto-1-methyl-1H-tetrazole and the mixture was cooled to −20° C. to −10° C. A solution of 152 mg of triethylamine in 1 ml of methylene chloride was added under stirring and then the mixture was allowed to stand at 20° C. to 25° C. The mixture was poured into a solution of 710 mg of 7β-[D-5-carboxy-5-(benzyloxycarbonylamino)valeramido]-3-hydroxymethyl-3-cephem-4-carboxylic acid ditriethylamine salt in 7 ml of methylene chloride under cooling at −30° C. to −20° C. and stirring. The whole mixture was stirred at the same temperature for 5 minutes and 15 ml of 2N HCl and 10 ml of tetrahydrofuran were added. The organic layer was taken, washed twice with 5 ml portions of saturated aqueous sodium chloride, dried over anhydrous magnesium sulfate, concentrated under reduced pressure and added to ether. The powdery precipitate was collected by filtration, dissolved in acetonitrile-water and subjected to silica gel column chromatography (silica gel: 20 g, column height: 24 cm), elution being carried out with acetonitrile-water-formic acid (20:2:0:1). The fractions were checked by TLC (developing solvent: the same as the above eluent) and the fractions (R$_f$: about 0.24) containing the desired product were collected and concentrated and ether was added. The resultant powder was collected by filtration and dried to give 370 mg (yield 61.1%) of 7β-[D-5-carboxy-5-(benzyloxycarbonylamino)valeramido]-3-[(1-methyl-1H-tetrazol-5-yl)thiomethyl]-3-cephem-4-carboxylic acid.

IR(KBr) cm$^{-1}$: 3300, 1775, 1715.

NMR(DMSO—d$_6$): δ 1.30~1.90(4H, m, CH$_2$×2) 2.00~2.30(2H, m, CH$_2$), 3.67(2H, br, 2—CH$_2$), 3.93(3H, s, N—CH$_3$), 4.30(2H, br, 3—CH$_2$), 4.80~5.20(4H, m, —CH$_2$O—, >CH—&C$_6$—H), 5.63(1H, q, J=5&8 Hz, C$_7$—H), 7.10~7.60

(m, 6H, 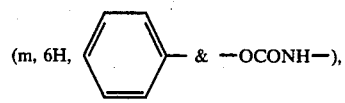 & —OCONH—),

8178(1H, d, J=8 Hz, —CONH—).

EXAMPLE 19

Using 1.81 g of 7β-[D-5-(p-t-butylbenzamido)-5-carboxyvalerylamido]-3-hydroxymethyl-3-cephem-4-carboxylic acid ditri-n-butylamine salt in place of 1.75 g of 7β-(D-5-carboxy-5-phthalimidovaleramido)-3-hydroxymethyl-3-cephem-4-carboxylic ditri-n-butylamine salt, the procedure of Example 5 was repeated to give 1.18 g (yield 93.4%) of 7-[D-5-(p-t-butylbenzamido)-5-carboxyvalerylamido]-3-(1-methyl-1H-tetrazol-5-yl)thiomethyl-3-cephem-4-carboxylic acid.

IR(KBr) cm$^{-1}$: 1776, 1727, 1640.

NMR(d$_6$—DMSO): δ 1.28(9H, s, CH$_3$×3), 1.70&2.21(6H, CH$_2$×3), 3.54&3.77(2H, ABq, J=18 Hz, 2—CH$_2$), 3.91(3H, s, >N—CH$_3$), 4.20&4.37(2H, ABq, J=13 Hz, 3—CH$_2$), 4.39(1H, >CH—), 5.02(1H, d, J=5 Hz, C$_6$—H), 5.64(1H, q, J=5&8 Hz, C$_7$—H), 7.43&7.81

(4H, 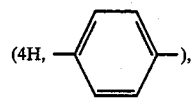 ), 8.42

(1H, d, J = 8Hz, 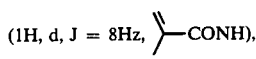—CONH), 8.79(1H, d, J=8 hz, —CONH—).

EXAMPLE 20

In 2 ml of methylene chloride was dissolved 0.450 g of o-phenylene phosphorochloridate, and at 0°–5° C., a solution of 0.437 g of tri-n-butylamine in 1 ml of methylene chloride and a solution of 7.60 mg of methanol in 2 ml of methylene chloride were added in that order. The mixture was stirred at room temperature for 20 minutes to make a methyl o-phenylene phosphate solution. This solution was added to a solution of 1.032 g of 7β-(D-5-carboxy-5-phthalimidovaleramido)-3-hydroxymethyl-3-cephem-4-carboxylic acid ditri-n-butylamine salt and 0.267 g of 2-mercaptobenzoxazole in 5 ml of methylene chloride under cooling at −20° C. to −25° C. and stirring, and the reaction was allowed to proceed at −20° C. to −10° C. for 80 minutes. To the reaction mixture was added 15 ml of water and, after phase separation, 15 ml of water was added to the organic layer. The pH was adjusted to 9.0 with N-NaOH and, after phase separation, the organic layer was further extracted twice with 5 ml of water. The aqueous layers were combined and washed with 5 ml of methylene chloride. The aqueous layer was adjusted to pH 2 with 2N HCl and extracted with a 1:1 mixture of methylene chloride and THF. The organic layer was washed twice with saturated aqueous sodium chloride and dried over anhydrous magnesium sulfate. The solvent was then distilled off and ether was added. The resulting powder was collected by filtration and dried to give 588 mg (yield 78.2%) of 7β-(D-5-carboxy-5-phthalimidovaleramido)-3-(benzoxazol-2-yl)thiomethyl-3-cephem-4-carboxylic acid.

IR(KBr) cm$^{-1}$: 3310, 2930, 1775, 1715, 1530, 1500.

NMR(d$_6$—DMSO): δ 1.30~2.40(6H, m, —CH$_2$CH$_2$CH$_2$—), 3.68(2H, ABq, 2—CH$_2$), 4.23&4.66(2H, ABq, J=14 Hz, 3—CH$_2$), 4.73(1H, t, J=7 Hz, >CH—), 5.04(1H, d, J=5 Hz, C$_6$—H), 5.63(1H, q, J=5&8 Hz, C$_7$—H), 7.20~7.77

(4H, m, 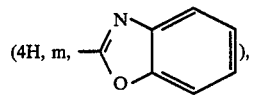), 7.87

(4H, s, 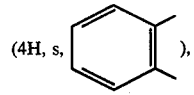), 8.78(1H, d, J=8 Hz, —CONH—).

EXAMPLE 21

Under cooling at −20° C. to −10° C. with stirring, a solution of 57.0 mg of methanol and 365 mg of tri-n-butylamine in 6 ml of methylene chloride was added to a solution of 376 mg of o-phenylene phosphorochloridate in 5 ml of methylene chloride and, then, at room temperature, the mixture was stirred for an hour to make a methyl o-phenylene phosphate solution. On the other hand, 874 mg of 7β-(D-5-carboxy-5-phthalimidovaleramido)-3-hydroxymethyl-3-cephem-4-carboxylic acid ditri-n-butylamine salt was dissolved in 5 ml of methylene chloride and a solution of 158 mg of pyridine in 2 ml of methylene chloride was added at 5°–0° C. Then, under cooling at −40° C. to −30° C., the above-mentioned methyl o-phenylene phosphate solution was added and the mixture was stirred at −30° C. to −10° C. for 45 minutes and at 0°–10° C. for 30 minutes. The powdery precipitate was collected by filtration, washed with methylene chloride and dried to give 465 mg (yield 82.4%) of 7β-(D-5-carboxy-5-phthalimidovaleramido)-3-cephem-3-pyridinium methyl-4-carboxylate.

IR(KBr) cm$^{-1}$: 3375, 3020, 2920, 1772, 1710, 1390.

NMR(D$_2$O+NaOD): δ 1.30~2.60(6H, m, —CH$_2$CH$_2$CH$_2$—), 2.90&3.55(2H, ABq, J=18 Hz, 2—CH$_2$), 5.10(1H, d, J=5 Hz, C$_6$—H), 5.32&5.66(2H, ABq, J=17 Hz, 3—CH$_2$), 5.63(1H, d, J=5 Hz, C$_7$—H), 7.78

(4H, s, 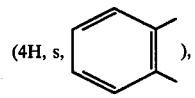), 8.03~9.06

(5H, m, 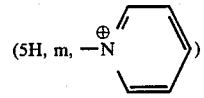)

EXAMPLE 22

Under ice-cooling and stirring, a solution of 646 mg of 2,6-lutidine and 96.8 mg of methanol in 7 ml of methylene chloride was added to a solution of 528 mg of o-phenylene phosphorochloridite in 3 ml of methylene chloride and the reaction was allowed to proceed for 5 minutes to make a methyl o-phenylene phosphite solution. To this solution was added 376 mg of isonicotinamide and the mixture was stirred for 10 minutes. Then, 923 mg of 7β-(D-5-carboxy-5-phthalimidovaleramido)-3-hydroxymethyl-3-cephem-4-carboxylic acid 2,6-lutidine salt was added and the mixture was stirred under ice-cooling for 2 hours and at room temperature for 5 hours. The reaction mixture was allowed to stand at −20° C. to −10° C. overnight. To this reaction mixture was added 15 ml of water and the mixture was adjusted to pH 7.0 with 1N NaOH. The aqueous layer was washed with methylene chloride, adjusted to pH 6.0 and concentrated under reduced pressure. The concentrate was subjected to Amberlite XAD-2 column chromatography, elution being carried out with water and water-methanol. The active fractions were collected, concentrated, and lyophilized to give 560 mg (yield 63.1%) of 7β-(D-5-carboxy-5-phthalimidovaleramido)-3-cephem-3-(4-carbamoylpyridinium)methyl-4-carboxylate sodium salt.

IR(KBr) cm$^{-1}$: 3350, 1773, 1708, 1613, 1463.

NMR(D$_2$O): δ 1.30~2.60(6H, m, —CH$_2$CH$_2$CH$_2$—), 2.90&3.55(2H, ABq, J=18 Hz, 2—CH$_2$), 5.10(1H, d, J=5 Hz, C$_6$—H), 5.34&5.68(2H, ABq, J=14 Hz, 3—CH$_2$), 5.60(1H, d, J=5 Hz, C$_7$—H), 7.79

(4H, s, 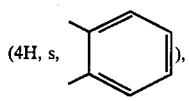), 8.41&9.14

(4H, dd, —N⊕ 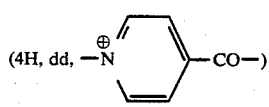 —CO—)

EXAMPLE 23

Under cooling at −50° to −40° C. and stirring, a solution of 0.455 g of tri-n-butylamine and 78.8 mg of methanol in methylene chloride was added to a solution of 0.469 g of o-phenylene phosphorochloridate in 5 ml of methylene chloride. The reaction was allowed to proceed to room temperature for 20 minutes to make a methyl o-phenylene phosphate solution. On the other hand, 0.339 g of tri-n-butylamine was added to a suspension of 1.066 g of 7β-(D-5-carboxy-5-phthalimidovaleramido)-3-hydroxymethyl-3-cephem-4-carboxylic acid ditri-n-butylamine salt and 0.322 g of 4,6-dimethyl-2-meraptopyrimidine hydrochloride in 5 ml of methylene chloride to prepare a solution. Then, under cooling at −30° C. to −35° C. and stirring, the above-mentioned methyl o-phenylene phosphate solution was added and the reaction was allowed to proceed at 0°–5° C. for an hour. To the reaction mixture was added 15 ml of water and the mixture was allowed to stand for phase separation. To the organic layer was added 15 ml of water and the mixture was adjusted to pH 6.0. After phase separation, 20 ml of water was added to the organic layer and the mixture was adjusted to pH 9.0 with 1N NaOH. The aqueous layer was taken and washed twice with 5 ml portions of methylene chloride. To the aqueous layer was added 45 ml of methylene chloride-tetrahydrofuran (1:1) and the mixture was adjusted to pH 2.0 with 2N HCl. After phase separation, the organic layer was washed with saturated aqueous sodium chloride and dried over anhydrous magnesium sulfate. The solvent was then distilled off and ether was added to the residue. The powdery precipitate was collected by filtration and dried to give 0.630 g (yield 82.5%) of 7β-(D-5-carboxy-5-phthalimidovaleramido)-3-(4,6-dimethylpyrimidin-2-yl)thiomethyl-3-cephem-4-carboxylic acid.

IR(KBr) cm$^{-1}$: 3290, 2930, 2560, 1773, 1710, 1580, 1530.

NMR(d$_6$—DMSO): δ  1.30~2.40(6H, m, —CH$_2$CH$_2$CH$_2$—), 2.35(6H, s, CH$_3$×2), 3.55(2H, 2—CH$_2$), 3.93&4.36(2H, ABq, J=14 Hz, 3—CH$_2$), 4.78

(1H, t, J = 7Hz, —CH), 4.99(1H, d, J=5 Hz, C$_6$—H), 5.56(1H, d, J=5×8 Hz, C$_7$—H), 6.93

(1H, s, 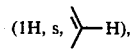—H), 7.87

(4H, s, 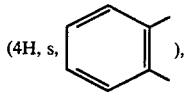), 8.22(1H, d, J=8 Hz, —CONH—).

EXAMPLE 24

(1) In 5 ml of methylene chloride was dissolved 0.195 g of 5-mercapto-1-methyl-1H-tetrazole and the solution was cooled to −10° C. Then, a solution of 0.268 g of o-phenylene phosphorochloridate in 5 ml of methylene chloride was added and, under cooling at −20° to −25° C., a solution of 1.170 g of diphenylmethyl 7β-(5-diphenylmethyloxycarbonyl-5-phthalimidovaleramido)-3-hydroxymethyl-3-cephem-4-carboxylate in 8 ml of methylene chloride was added dropwise. The mixture was stirred at the same temperature for 20 minutes. To the reaction mixture was added 10 ml of water and, then, the mixture was allowed to stand at room temperature for phase separation. The organic layer was washed with water, dried over anhydrous sodium sulfate, concentrated and poured into 80 ml of ether. The powdery precipitate was collected by filtration and subjected to silica gel column chromatography (silica gel: 30 g, column height: 36 cm), elution being carried out with ethyl acetate-n-hexane (4:1). The fractions were checked by TLC (developing solvent: the same as the above eluent) and the fractions (R$_f$: about 0.71) containing the desired product were collected and concentrated. To the concentrate was added ether to give diphenylmethyl 7β-(5-diphenylmethyloxycarbonyl-5-phthalimidovaleramido)-3-(1-methyl-1H-tetrazol-5-yl)thiomethyl-3-cephem-4-carboxylate.

IR(KBr) cm$^{-1}$: 3350, 3030, 2930, 1780, 1717.

NMR(d$_6$—DMSO): δ  1.30~2.40(6H, m, —CH$_2$CH$_2$CH$_2$—), 3.68(2H, broad s, 2—CH$_2$), 3.88

(3H, s, —N̶—CH$_3$), 4.24(2H, broad s, 3—CH$_2$), 4.90~5.20(2H, m, C$_6$—H&->CH—), 5.73(1H, q, J=5&8 Hz), 6.83&6.90(2H, s, —COOCH<×2), 7.10~7.60

(20H, m, ( 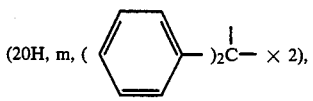 )$_2$C— × 2), 7.91

(4H, s, 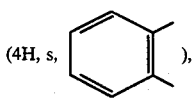), 8.87(1H, d, J=8 Hz, —CONH—).

(2) In 5 ml of methylene chloride were dissolved 0.182 g of 5-mercapto-1-methyl-1H-tetrazole and 0.485 g of tri-n-butylamine and the solution was cooled to −10° C. A solution of 0.250 g of o-phenylene phosphorochloridate in 5 ml of methylene chloride was added and the mixture was cooled to −20° to −25° C. To this mixture was added 1.09 g of diphenylmethyl 7β-(5-diphenylmethyloxycarbonyl-5-phthalimidovaleramido)-3-hydroxymethyl-3-cephem-4-carboxylate and the whole mixture was further treated in the same manner as described in 1) above to give the desired product, whose IR and NMR spectra were identical with those of the compound obtained in 1).

EXAMPLE 25

(1) To 10 ml of ethyl acetate were added 0.540 g of 7β-(2-thienylacetamido)-3-hydroxymethyl-3-cephem-4-carboxylic acid tri-n-butylamine salt and 0.175 g of 5-mercapto-1-methyl-1H tetrazole and, under cooling at −20° C. and stirring, a solution of 0.370 g of methyl o-phenylene phosphorochloridate in 5 ml of ethyl acetate was added. The mixture was stirred under ice-cooling for 1.5 hours and 10 ml of water was added. After phase separation, 20 ml of water was added to the organic layer and the mixture was adjusted to pH 9.0. The aqueous layer was taken and washed with 5 ml of ethyl acetate. To the aequous layer was added 20 ml of ethyl acetate and the mixture was adjusted to pH 2.0. After phase separation, the organic layer was washed with saturated aqueous sodium chloride and dried over anhydrous sodium sulfate. The ethyl acetate was distilled off under reduced pressure and ether was added. The powdery precipitate was collected by filtration to give 0.380 g (yield 84.1%) of 7β-(2-thienylacetamido)-3-(1-methyl-1H-tetrazol-5-yl)thiomethyl-3-cephem-4-carboxylic acid. The IR and NMR spectra of this product were identical with those of the authentic sample.

(2) Using 0.477 g of 7β-phenylacetamido-3-hydroxymethyl-3-cephem-4-carboxylic acid di-n-butylamine salt, the procedure of 1) above was repeated to give 0.361 g (yield 80.9%) of 7-phenylacetamido-3-(1-methyl-1H-tetrazol-5-yl)thiomethyl-3-cephem-4-carboxylic acid. The IR and NMR spectra of this product were identical with those of the authentic sample.

EXAMPLE 26

To 180 mg of 5-mercapto-1-methyl-1H-tetrazole was added a solution of 271 mg of o-phenylene phosphorochloridite in 4 ml of methylene chloride, followed by addition of a solution of 157 mg of triethylamine in 3 ml of methylene chloride. Then, under cooling at −5° C. and stirring, 732 mg of 7β-(D-5-carboxy-5-phthalimidovaleramido)-3-hydroxymethyl-3-cephem-4-carboxylic acid ditriethylamine salt was added and the mixture was stirred at the same temperature for 5 minutes. To the reaction mixture were added 10 ml of water and 7 ml of tetrahydrofuran and the mixture was adjusted to pH 2. After phase separation, 20 ml of water was added to the organic layer and the mixture was adjusted to pH 7.0. The methylene chloride and tetrahydrofuran were distilled off under reduced pressure and 10 ml of methylene chloride was added. The mixture was adjusted to pH 9.0 with 1N NaOH. The aqueous layer was taken, washed with 10 ml of methylene chloride, and 20 ml of methylene chloride-tetrahydrofuran (1:1) was added. The mixture was adjusted to pH 2.0 with 2N HCl. After phase separation, the organic layer was washed with saturated aqueous sodium chloride, dried over sodium sulfate and concentrated. To the residue was added ether and the powdery precipitate was collected by filtration and dried to give 410 mg (yield 65.7%) of 7β-(D-5-carboxy-5-phthalimidovaleramido)-3-(1-methyl-1H-tetrazol-5-yl)thiomethyl-3-cephem-4-carboxylic acid. The IR and NMR spectra of this product were identical with those of the compound obtained in Example 1.

EXAMPLE 27

(1) To a solution of 762 mg (4 mM) of o-phenylene phosphorochloridate in 10 ml of methylene chloride was added 741 mg (4 mM) of tri-n-butylamine and a solution of 128 mg (4 mM) of methanol in 5 ml of methylene chloride was added dropwise to make a methyl o-phenylene phosphate solution. On the other hand, 874 mg of 7β-(D-5-carboxy-5-phthalimidovaleramido)-3-hydroxymethyl-3-cephem-4-carboxylic acid ditri-n-butylamine salt and 174 mg of 5-mercapto-1-methyl-1H-tetrazole were dissolved in 5 ml of methylene chloride and, under cooling at −15° to −10° C., the solution was added dropwise to the above-mentioned methyl o-phenylene phosphate solution. The mixture was stirred at the same temperature for 40 minutes and the methylene chloride was distilled off under reduced pressure. The residue was dissolved in water-acetonitrile (3:2, v/v). The solutoin was assayed for 7β-(D-5-carboxy-5-phthalimidovaleramido)-3-(1-methyl-1H-tetrazol-5-yl)thiomethyl-3-cephem-4-carboxylic acid by high performance liquid chromatography. The yield was 537 mg or 89.3%.

(2)–(18)

In the reaction procedure described above in (1), 4 mM of each hydroxy compound specifically given in Table 1 was employed in place of 128 mg of methanol for the preparation of a solution containing the corresponding o-phenylene phosphorochloridate esterification product. Using this solution and following the above procedure (1), the reaction was carried out at a temperature of −15° C. to −10° C. and the reaction mixture was assayed. The reaction time and yield of 7β-(D-5-carboxy-5-phthalimidovaleramido)-3-(1-methyl-1H-tetrazol-5-yl)thiomethyl-3-cephem-4-carboxylic acid were as shown in Table 1.

TABLE 1

| No. | Hydroxy compound | Reaction time (min.) | Yield (mg) | Yield (%) |
|---|---|---|---|---|
| (2) | $CH_3OH$ | 35 | 493 | 82.0 |
| (3) | $CH_3OH$ | 40 | 511 | 84.9 |
| (4) | $C_2H_5OH$ | 60 | 505 | 84.0 |
| (5) | $C_2H_5OH$ | 120 | 507 | 84.3 |
| (6) | $Cl_3CCH_2OH$ | 5 | 493 | 84.9 |
| (7) | $BrCH_2CH_2OH$ | 20 | 509 | 84.6 |
| (8) | $n\text{-}C_3H_7OH$ | 140 | 531 | 88.3 |
| (9) | $i\text{-}C_3H_7OH$ | 180 | 434 | 72.1 |
| (10) | $BrCH_2CH(Br)CH_2OH$ | 20 | 475 | 79.0 |
| (11) | $n\text{-}C_4H_9OH$ | 150 | 493 | 82.0 |
| (12) | $i\text{-}C_4H_9OH$ | 150 | 502 | 83.5 |
| (13) | $sec\text{-}C_4H_9OH$ | 210 | 513 | 85.3 |
| (14) | 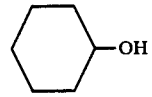 | 270 | 505 | 83.9 |

TABLE 1-continued

| No. | Hydroxy compound | Reaction time (min.) | Yield (mg) | Yield (%) |
| --- | --- | --- | --- | --- |
| (15) | ⟨benzene⟩—OH | 10 | 495 | 82.3 |
| (16) | ⟨benzene⟩—OH | 5 | 509 | 84.6 |
| (17) | $CH_2=CH-CH_2OH$ | 40 | 498 | 82.8 |
| (18) | $CH_2=C(CH_3)CH_2OH$ | 40 | 490 | 81.5 |

EXAMPLE 28

Under cooling at −10° C. to 0° C., 741 mg of tri-n-butylamine was added to a solution or 762 mg of o-phenylene phosphorochloridate in 12 ml of methylene chloride and, then, at room temperature, 236 mg of n-propylamine was added. The reaction was allowed to proceed at the same temperature for 10 minutes to make an 2-oxo-2-propylamino-1,3,2-benzodioxaphosphole solution. Then, under cooling at −15° C. to −10° C., a solution of 874 mg of 7β-(D-5-carboxy-5-phthalimidovaleramido)-3-hydroxymethyl-3-cephem-4-carboxylic acid ditri-n-butylamine salt and 174 mg of 5-mercapto-1-methyl-1H-tetrazole in 5 ml of methylene chloride was added dropwise to the above-mentioned solution. The reaction was allowed to proceed at the same temperature for 150 minutes and the methylene chloride was distilled off under reduced pressure. The residue was treated and assayed in the same manner as Example 27 (1). The yield of 7β-(D-5-carboxy-5-phthalimidovaleramido)-3-(1-methyl-1H-tetrazol-5-yl)thiomethyl-3-cephem-4-carboxylic acid was 454 mg (75.5%).

EXAMPLE 29

(1) To 5.5 g of pyrocatechol were added 110 ml of methylene chloride and 15.2 g of triethylamine. Then, under stirring at 10°-20° C., 7.29 g of phosphorus oxychloride was added dropwise to the above solution over 10 minutes. The reaction mixture was filtered in a nitrogen gas stream and washed with a small amount of methylene chloride to give 124 ml of a substantially clear filtrate.

(2) Under cooling at −10° C. to 0° C. and stirring, 9.4 ml of the filtrate as obtained in (1) was added dropwise to a solution of 7β-(D-5-carboxy-5-phthalimidovaleramido)-3-hydroxymethyl-3-cephem-4-carboxylic acid ditriethylamine salt and 168 mg of 5-mercapto-1-methyl-1H-tetrazole in 6 ml of methylene chloride and the reaction was allowed to proceed at the same temperature for 2 hours. The reaction mixture was left standing at 0°-5° C. overnight. Then, under ice-cooling, 10 ml of 2N HCl was added and the mixture was adjusted to pH 2. To this mixture was added 18 ml of tetrahydrofuran-water (1:1, v/v), and the insoluble matter was filtered off and washed with 2 ml of the above tetrahydrofuran-water mixture. The filtrate and washings were combined and allowed to stand for phase separation. The organic layer was washed with 10 ml of water and the aqueous layer was extracted with 2 ml of methylene chloride. The extract and the previous organic layer were combined, dried over anhydrous magnesium sulfate, concentrated to about 5 ml, and poured into 70 ml of ether. The powdery precipitate was collected by filtration, washed with ether and dried to give 514 mg (yield 71.0%) of 7β-(D-5-carboxy-5-phthalimidovaleramido)-3-(1-methyl-1H-tetrazol-5-yl)thiomethyl-3-cephem-4-carboxylic acid, the NMR and IR spectra of which were identical with those of the authentic sample.

EXAMPLE 30

In 6 ml of methylene chloride were dissolved 849 mg of 7β-(D-5-carboxy-5-phthalimidovaleramido)-3-hydroxymethyl-3-cephem-4-carboxylic acid ditriethylamine salt and 194 mg of 2-mercaptobenzothiazole and, under stirring at −10° C. to 0° C., 9.4 ml of the filtrate as obtained in Example 29 (1) was added dropwise. The reaction was allowed to proceed at room temperature for 40 minutes and the reaction mixture was left standing at 0°-5° C. overnight. This reaction mixture was further treated in the same manner as Example 29 (2) to give 467 mg (yield 59.6%) of 7β-(D-5-carboxy-5-phthalimidovaleramido)-3-[(benzothiazol-2-yl)thiomethyl]-3-cephem-4-carboxylic acid. The IR and NMR spectra of this product were identical with those of the compound obtained in Example 12.

EXAMPLE 31

(1) To 3.64 g of ethyl 3,4-dihydroxybenzoate were added 44 ml of methylene chloride and 6.06 g of triethylamine. Then, at 10°-20° C., 2.92 g of phosphorus oxychloride was added dropwise to the above solution over 10 minutes. The mixture was filtered in a nitrogen gas stream and the residue on the filter was washed with 20 ml of methylene chloride. The filtrate and washings were combined and the solution thus obtained amounted to 62 ml.

(2) To 168 mg of 5-mercapto-1-methyl-1H-tetrazole was added 17.6 ml of the solution as obtained in (1). Then, under cooling at 0°-5° C. and stirring, 849 mg of 7β-(D-5-carboxy-5-phthalimidovaleramido)-3-hydroxymethyl-3-cephem-4-carboxylic acid ditriethylamine salt was added and the reaction was allowed to proceed at the same temperature for 2 hours. To the reaction mixture were added 10 ml of water and 10 ml of methylene chloride and the mixture was adjusted to pH 2. After phase separation, the organic layer was washed with 5 ml of water. To the organic layer was added 20 ml of water and the mixture was adjusted to pH 8.5 with 1N NaOH and allowed to stand for phase separation. The organic layer was washed with 10 ml of water. The aqueous layers were then combined and washed twice with 5 ml portions of methylene chloride. To the aqueous layer were added 15 ml of methylene chloride and 15 ml of tetrahydrofuran and the mixture was adjusted to pH 2 with 4N HCl and allowed to stand for phase separation. The aqueous layer was washed with 10 ml of methylene chloridetetrahydrofuran (1:1, v/v). The organic layers were combined, washed twice with 10 ml portions of saturated aqueous sodium chloride and dried over anhydrous magnesium sulfate. The solvent was then distilled off and ether was added to the residue. The powdery precipitate was collected by filtration, washed with ether and dried to give 510 mg (yield 70.5%) of 7β-(D-5-carboxy-5-phthalimidovaleramido)-3-(1-methyl-1H-tetrazol-5-yl)thiomethyl-3-cephem-4-carboxylic acid. The IR spectrum of this product was identical with that of the authentic sample.

EXAMPLE 32

(1) To 3.27 g of 2,3-dihydroxynaphthalene were added 44 ml of methylene chloride and 6.06 g of triethylamine and, under cooling at 10°–20° C. and stirring, 2.92 g of phosphorus oxychloride was added dropwise to the resultant solution. The mixture was filtered in a nitrogen gas stream and the residue on the filter was washed with 20 ml of methylene chloride. The filtrate and washings were combined and the solution thus obtained amounted to 56 ml.

(2) To 168 mg of 5-mercapto-1-methyl-1H-tetrazole was added 15.9 ml of the solution as obtained in (1). To the resultant solution was added 849 mg of 7β-(D-5-carboxy-5-phthalimidovaleramido)-3-hydroxymethyl-3-cephem-4-carboxylic acid ditriethylamine salt under cooling at 0°–5° C. and stirring. The reaction was allowed to proceed at the same temperature for 2 hours and then at room temperature for 5 hours. The reaction mixture was left standing at 0°–5° C. overnight and further treated in the same manner as Example 31 (2) to give 7β-(D-5-carboxy-5-phthalimidovaleramido)-3-(1-methyl-1H-tetrazol-5-yl)thiomethyl-3-cephem-4-carboxylic acid. The NMR spectrum of this product was identical with that of the authentic sample.

EXAMPLE 33

(1) To a mixture of 44 ml of methylene chloride and 6.06 g of triethylamine was added 2.20 g of pyrocatechol and, under ice-cooling, 2.61 g of phosphorus trichloride was added portionwise to the resultant solution. The mixture was further treated in the same manner as Example 32 (1) and the solution thus obtained amounted to 52 ml.

(2) Using 14.8 ml of the solution as obtained in (1) and following the procedure of Example 32 (2), the reaction was carried out for 30 minutes. The reaction mixture was further treated in the same manner as Example 32 (2) to give 433 mg (60.0%) of 7β-(D-5-carboxy-5-phthalimidovaleramido)-3-(1-methyl-1H-tetrazol-5-yl)thiomethyl-3-cephem-4-carboxylic acid. The IR and NMR spectra were identical with those of the authentic sample.

EXAMPLE 34

(1) In a mixture of 44 ml of methylene chloride and 10.1 g of triethylamine was dissolved 2.20 g of pyrocatechol and, under ice-cooling and stirring, 3.96 g of phosphorus pentachloride was added portionwise. The mixture was further treated in the same manner as Example 32 (1) and the solution thus obtained amounted to 48 ml.

(2) Using 13.7 ml of the solution as obtained in (1), the procedure of Example 31 (2) was repeated to give 7β-(D-5-carboxy-5-phthalimidovaleramido)-3-(1-methyl-1H-tetrazol-5-yl)thiomethyl-3-cephem-4-carboxylic acid. The IR spectrum of this product was identical with that of the authentic sample.

EXAMPLE 35

(1) In a mixture of 40 ml of methylene chloride and 7.76 g of diisobutylamine was dissolved 2.20 g of pyrocatechol and, under ice-cooling, 2.92 g of phosphorus oxychloride was added portionwise over 10 minutes. The mixture was stirred at room temperature for 10 minutes and the red-brown solution thus obtained amounted to 50 ml.

(2) Using 14.2 ml of the reaction mixture as obtained in (1) and following the procedure of Example 31 (2), the reaction was carried out under ice-cooling fo 50 minutes and then at room temperature for 2.5 hours. The reaction mixture was further treated in the same manner as Example 31 (2) to give 471 mg (65.2%) of 7β-(D-5-carboxy-5-phthalimidovaleramido)-3-(1-methyl-1H-tetrazol-5-yl)thiomethyl-3-cephem-4-carboxylic acid. The NMR specturm of this product was identical with that of the authentic sample.

EXAMPLE 36

(1) In a mixture of 40 ml of methylene chloride and 6.06 g of triethylamine was dissolved 2.20 g of pyrocatechol. Then, under ice-cooling, 2.61 g of phosphorus trichloride was added portionwise and 4 ml of methylene chloride was further added. The mixture was stirred at room temperature for 10 minutes and cooled again to 5° C. On addition of 0.64 g of methanol, the temperature of the solution increased to 18° C. The reaction mixture was stirred at room temperature for 10 minutes and filtered in a nitrogen gas stream. The residue on the filter was washed with methylene chloride and the filtrate and washings were combined. The solution thus obtained amounted to 55 ml.

(2) To 168 mg of 5-mercapto-1-methyl-1H-tetrazole was added 15.6 ml of the solution as obtained in (1). To the resultant solution was added 849 mg of 7β-(D-5-carboxy-5-phthalimidovaleramido)-3-hydroxymethyl-3-cephem-4-carboxylic acid ditriethylamine salt under ice-cooling, and the mixture was stirred at the same temperature for 1.5 hours and then at room temperature for 2.0 hours. The reaction mixture was left standing at 0°–5° C. overnight and the reaction was allowed to proceed at room temperature for 6 hours. The reaction mixture was further treated in the same manner as Example 31 (2) to give 482 mg (66.8%) of 7β-(D-5-carboxy-5-phthalimidovaleramido)-3-(1-methyl-1H-tetrazol-5-yl)thiomethyl-3-cephem-4-carboxylic acid. The IR spectrum of this product was identical with that of the authentic sample.

EXAMPLE 37

In 10 ml of methylene chloride were dissolved 450 mg of 5-mercapto-1-methyl-1H-tetrazole and 437 mg of 7β-(D-5-carboxy-5-phthalimidovaleramido)-3-hydroxymethyl-3-cephemcarboxylic acid ditributylamine salt and, under cooling at −25° C. to −20° C., 0.5 ml of 2,2-dihydro-4,5-dimethyl-2,2,2-trimethoxy-1,3,2-dioxaphosphole was added dropwise over 5 minutes. The mixture was stirred at the same temperature for 5 minutes and 15 ml of water was added. After phase separation, the aqueous layer was washed with 5 ml of methylene chloride and the organic layers were combined. Then, 15 ml of water was added and the mixture was adjusted to pH 8.5 with 1N NaOH and allowed to stand for phase separation. The aqueous layer was washed with 5 ml of methylene chloride, and 10 ml of tetrahydrofuran and 15 ml of methylene chloride were added. The mixture was adjusted to pH 2.8 with 2N HCl and allowed to stand for phase separation. The organic layer was washed with 5 ml of water and 5 ml of saturated aqueous sodium chloride in that order and dried over anhydrous magnesium sulfate. The solvent was then distilled off and a small amount of acetone was added to the residue. To the resultant solution was added ether and the powdery precipitate was collected by filtration, washed with ether and dried to give 215 mg (71.5%) of 7β-(D-5-carboxy-5-phthalimidovaleramido)-3-(1-methyl-1H-tetrazol-5-yl)thiomethyl-3-cephem-4-carboxylic acid. The IR and NMR spectra of this product were identical with those of the authentic sample.

EXAMPLE 38

(1) To a solution of 1.86 g of triphenyl phosphite in 12 ml of methylene chloride was added a solution of 1.476 g of o-chloranil in 10 ml of methylene chloride at room temperature. The thus-obtained solution of 2,2-dihydro-4,5,6,7-tetrachloro-2,2,2-triphenoxy-1,3,2-benzodioxaphosphole in methylene chloride amounted to 23 ml.

(2) Using 3.0 ml of the solution as obtained in (1) in place of 0.5 ml of 2,2-dihydro-4,5-dimethyl-2,2,2-trimethoxy-1,3,2-dioxaphosphole, the procedure of Example 37 was repeated to give 220 mg (73.1%) of 7β-(D-5-carboxy-5-phthalimidovaleramido)-3-(1-methyl-1H-tetrazol-5-yl)thiomethyl-3-cephem-4-carboxylic acid. The IR and NMR spectra of this product were identical with those of the authentic sample.

EXAMPLE 39

In 15 ml of acetonitrile was suspended 0.173 g of 1-(2-dimethylaminoethyl)-5-mercapto-1H-tetrazole, followed by addition of 0.152 g of triethylamine. Then, 0.874 g of 7β-(D-5-carboxy-5-phthalimidovaleramido)-3-hydroxymethyl-3-cephem-4-carboxylic acid ditri-n-butylamine salt was added and the resultant solution was cooled to −25° C. Under cooling at −25° C. to −20° C., a solution of 0.744 g of methyl o-phenylene phosphate in 5 ml of methylene chloride was added dropwise and the mixture was stirred at the same temperature for 20 minutes. To the reaction mixture was added 5 ml of water and the mixture was concentrated under reduced pressure. The residue was diluted to exactly 50 ml with water-acetonitrile (3:2, v/v) and the solution was assayed for 7β-(D-5-carboxy-5-phthalimidovaleramido)-3-[1-(2-dimethylaminoethyl)-1H-tetrazol-5-yl]thiomethyl]-3-cephem-4-carboxylic acid by high performance liquid chromatography. The yield was 0.593 g (90.0%). To a 45.0 ml portion of the above dilution (50 ml) was added 4.0 ml of 1N HCl and the mixture was concentrated and lyophilized. The resultant syrupy solid was dissolved in ethanol, followed by addition of ether. The powdery precipitate was collected by filtration, washed with ether and dried to give 0.54 g of the hydrochloride of the above-indicated desired compound. The NMR spectrum of this product was identical with that of the compound obtained in Example 2.

EXAMPLE 40

In a mixture of 4 ml of formamide and 6 ml of acetonitrile were dissolved 1.75 g of 7β-(D-5-carboxy-5-phthalimidovaleramido)-3-hydroxymethyl-3-cephem-4-carboxylic acid ditri-n-butylamine salt and 0.293 g of isonicotinamide and the solution was cooled to −20° C. Then, under stirring and cooling at −20° C. to −15° C., a solution of 0.74 g of methyl o-phenylene phosphate in 2 ml of methylene chloride was added dropwise and the reaction was allowed to proceed at the same temperature for 30 minutes. The reaction mixture was warmed to 10° C. and 50 ml of acetonitrile and 50 ml of ether were added. The powdery precipitate was collected by filtration, washed with acetonitrile and dried to give 1.04 g (yield 85.5%) of 7β-(D-5-carboxy-5-phthalimidovaleramido)-3-cephem-3-(4-carbamoylpyridinium)methyl-4-carboxylate.

NMR (D$_2$O+K$_2$CO$_3$): Identical with that of the compound obtained in Example 22

EXAMPLE 41

Using a solution of 0.93 g of 2-phenyl-1,3,2-benzodioxaphosphole-2-oxide in 4 ml of methylene chloride in place of 0.74 g of methyl o-phenylene phosphate and following the procedure of Example 5, the reaction was carried out for 10 minutes. The reaction mixture was further treated in the same manner as Example 5 to give 1.12 (yield 93.1%) of the desired product. The IR and NMR spectra of this product were identical with those of the compound obtained in Example 1.

EXAMPLE 42

In 5 ml of water was dissolved 0.670 g of 7β-(D-5-carboxy-5-phthalimidovaleramido)-3-hydroxymethyl-3-cephem-4-carboxylic acid dipotassium salt.5 H$_2$O, followed by addition of 5 ml of tetrahydrofuran. The mixture was adjusted to pH 2.5 with 4N HCl at 5° C. or below and 10 ml of methylene chloride was added. After phase separation, the aqueous layer was extracted with 2.5 ml of tetrahydrofuran and 5 ml of methylene chloride and the organic layers were combined, dried over anhydrous magnesium sulfate and concentrated under reduced pressure. To the concentrate were added 10 ml of tetrahydrofuran and 50 ml of methylene chloride and the mixture was concentrated. The residue was dissolved in 10 ml of tetrahydrofuran, followed by addition of 0.174 g of 5-mercapto-1-methyl-1H-tetrazole. Then, at −15° C. to −10° C., a solution of 0.744 g of methyl o-phenylene phosphate in 4 ml of tetrahydrofuran was added and the mixture was stirred at the same temperature for 50 minutes and concentrated under reduced pressure. The residue was dissolved in a small amount of tetrahydrofuran and poured into 100 ml of ether. The powdery precipitate was collected by filtration, washed with ether and dried to give 0.560 g (93.1%) of 7β-(D-5-carboxy-5-phthalimidovaleramido)-3-(1-methyl-1H-tetrazol-5-yl)thiomethyl-3-cephem-4-carboxylic acid. The NMR and IR spectra of this product were identical with those of the compound obtained in Example 1.

EXAMPLE 43

Using a solution of 0.65 g of 2-oxo-4,5-dimethyl-2,2-dihydro-2-methoxy-1,3,2-dioxaphosphole in 4 ml of methylene chloride in place of 0.74 g of methyl o-phenylene phosphate and following the procedure of Example 5, the reaction was carried out for 30 minutes. The reaction mixture was further treated in the same manner as Example 5 to give 0.95 g (79.0%) of the desired product. The IR and NMR spectra of this product were identical with those of the compound obtained in Example 1.

EXAMPLE 44

(1) (24 ml) was added to 8.78 g of deacetylcephalosporin C sodium salt (purity: 90.1%) for dissolution of the later, followed addition of 8 ml of tetrahydrofuran (THF). To the mixture, there were added dropwise alternately 40% aqueous potassium carbonate solution and 3.76 g of phenyl chlorocarbonate while maintaining the mixture at pH 9.5–10.0 and at 15°–20° C. After the addition, the mixture was stirred for 10 minutes, then 40 ml of THF was added, and concentrated hydrochloric acid was added dropwise with cooling at 3°–5° C. until pH 2.5. Following addition of 65 ml of methylene chloride, the whole mixture was allowed to stand for phase separation. Then the aqueous layer was further extracted with a mixture of 17 ml of THF and 34 ml of methylene chloride. The organic layers were combined and dried over anhydrous magnesium sulfate and, following addition of 8.16 g of tri-n-butylamine, they were concentrated to dryness under reduced pressure. Methylene chloride was added to the residue and the solution was again evaporated to dryness. The residue was dissolved in methylene chloride and the solution was dropped into ether. The resulting powdery precipitate was collected by filtration to give 16.2 g of ditri-n-butylamine salt of 7β-(D-5-carboxy-5-phenoxycarbonylaminovaleramido)-3-hydroxymethyl-3-cephem-4-carboxylic acid.

IR (KBr) cm$^{-1}$; 3250, 2930, 1760, 1735, 1660, 1600.

NMR (d$_6$—DMSO): δ 0.7~2.9 and 2.6~3.1 (m, (CH$_3$CH$_2$CH$_2$CH$_2$)$_3$N & —(CH$_2$)$_3$CO—), 3.45 (br, 2—CH$_2$), 3.90 (t, J=6 Hz, >CH—), 4.15 (br, 3—CH$_2$), 4.94 (d, J=5 Hz, C$_6$—H), 5.52 (q, J=5×8 Hz, C$_7$—H), 6.9~7.6

(m,  ), 7.7~8.9 (m, —O—CONH—, C—CONH, —COOH).

(2) 7β-(D-5-carboxy-5-phenoxycarbonylaminovaleramido)-3-hydroxymethyl-3-cephem-4-carboxylic acid ditri-n-butylamine salt (8.64 g) was dissolved in 100 ml of methylene chloride, 1.74 g of 5-mercapto-1-methyl-1H-tetrazole was added to and dissolved in the solution. Thereto was added dropwise with cooling at −20° to −25° C. a solution of 3.72 g of methyl o-phenylene phosphate in 10 ml of methylene chloride over 5 minutes. Thereafter, the whole mixture was stirred at 0° to −5° C. for 60 minutes. Cold water (80 ml) was added to the reaction mixture, the resulting mixture was adjusted to pH 8.5 with 1N NaOH and, after phase separation, the aqueous layer was washed with two 20-ml portions of methylene chloride. THF (50 ml) and 50 ml of methylene chloride were added to the aqueous layer, the mixture was adjusted to pH 1.5 by adding concentrated hydrochloric acid dropwise and, after phase separation, the aqueous layer was further extracted with a mixture of 15 ml of THF and 15 ml of methylene chloride. The organic layers were combined, dried over anhydrous magnesium sulfate and concentrated until only a small amount of the solvent was remaining. The residue was added dropwise to 300 ml of ether and the powdery precipitate was collected by filtration, washed with ether and dried in vacuo to give 5.41 g (91.4% yield) of 7β-(D-5 carboxy-5-phenoxycarbonylaminovaleramido)-3-(1-methyl-1H-tetrazol-5-yl)thiomethyl-3-cephem-4-carboxylic acid.

IR (KBr) cm$^{-1}$; 3270, 3020, 2920, 1780, 1725, 1530.

NMR (d$_6$—DMSO); δ1.4~2.4 (6H, m—(CH$_2$)$_3$—), 3.69 (2H, br, 2—CH$_2$), 3.94 (3H, s, N—CH$_3$), 4.30 (2H, br, 3—CH$_2$), 5.05 (1H, d, J=5 Hz, C$_6$—H), 5.65 (1H, q, J=5×8 HZ, C$_7$—H), 6.9~7.6

(5H, m, 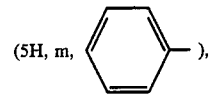 ), 8.03 (1H, d, J=8 HZ, —OCONH—), 8.83 (1H, d, J=8 HZ, —CONH—).

EXAMPLE 45

(1) Water (25 ml) was added to 10.95 g of deacetylcephalosporin C sodium salt (purity: 90.1%) for dissolution of the latter, followed by addition of 7 ml of acetonitrile. 40% Aqueous potassium carbonate solution and 3.38 g of ethyl chlorocarbonate were added dropwise and alternately to the mixture with stirring and cooling at 15°-20° C. and maintaining the pH at 9.5-10. The reaction mixture was concentrated under reduced pressure, whereby the acetonitrile was distilled off. The residue was cooled to 0°-5° C. and adjusted to pH 2.5 with concentrated hydrochloric acid. The resulting precipitate was collected by filtration, washed with cold water and then suspended in 200 ml of water. To the suspension was added 8 ml of triethylamine with stirring until dissolution. The mixture was then concentrated under reduced pressure. The residue was lyophilized and dried in vacuo in a desiccator containing phosphoric anhydride to give 15.2 g of 7β-(D-5-carboxy-5-ethoxycarbonylaminovaleramido)-3-hydroxymethyl-3-cephem-4-carboxylic acid ditriethylamine salt.

IR (KBr) cm$^{-1}$; 3550~3150, 2930, 2840, 2670, 2480, 1762, 1710~1660, 1600, 1535.

NMR (D$_2$O); δ1.14 (3H, t, J=7 Hz, —CH$_3$), 1.26 (18H, t, J=7 Hz, CH$_3$×6), 1.5~1.9 (4H, m, —CH$_2$CH$_2$—), 2.2~2.5 (2H, m, —CH$_2$CO—), 3.19 (12H, q, J=7 Hz, CH$_2$×6), 3.54 (2H, ABq, 2—CH$_2$), 4.08 (2H, q, J=7 Hz, —CO$_2$CH$_2$—), 4.26 (2H, s, 3—CH), 5.08 (1H, d, J=5 Hz, C$_6$—H), 5.59 (1H, d, J=5 Hz, C$_7$—H).

(2) Methylene chloride (15 ml), 5 ml of acetonitrile, 0.35 g of 5-mercapto-1-methyl-1H-tetrazole and 0.2 ml of tri-n-butylamine were added to 1.30 g of 7β-(D-5-carboxy-5-ethoxycarbonylaminovaleramido)-3-hydroxymethyl-3-cephem-4-carboxylic acid ditriethylamine salt. The resulting solution was cooled to −15° to −10° C. and thereto was added a solution of 0.74 g of methyl o-phenylene phosphate in 2 ml of methylene chloride dropwise with stirring over 5 minutes. Thereafter, the mixture was stirred at 0°-5° C. for 30 minutes and then concentrated under reduced pressure. To the residue were added 20 ml of methylene chloride and 15 ml of water, the mixture was cooled to 0°-5° C. and adjusted to pH 9.0 with 1N NaOH and, after phase separation, the organic layer was washed with 3 ml of water. The aqueous layer and extract were combined and washed with 5 ml of methylene chloride. To the thus-obtained aqueous layer were added 10 ml of tetrahydrofuran and 20 ml of methylene chloride. The mixture was cooled to 0°-5° C. and adjusted to pH 2 with 2N HCl. The organic layer was separated, and 5 ml of tetrahydrofuran and 10 ml of methylene chloride were added to the aqueous layer and the resulting mixture was allowed to stand for phase separation. The organic layers were combined, dried over anhydrous magnesium sulfate and concentrated. Addition of ether to the residue and collection of the resulting powder by filtration gave 0.97 g (89.2% yield) of 7β-(D-5-carboxy-5-ethoxycarbonylaminovaleramido)-3-(1-methyl-1H-tetrazol-5-yl)thiomethyl-3-cephem-4-carboxylic acid.

IR (KBr) cm$^{-1}$, 3280, 2950, 1775, 1710, 1530.

NMR (d$_6$—DMSO), δ1.08 (3H, t, J=7 Hz, —CH$_3$), 1.4~2.4 (6H, m, —CH$_2$CH$_2$CH$_2$—), 2.68 (3H, s, N—CH$_3$), 3.63 (2H, ABq, 2—CH$_2$), 3.97 (2H, q, J= 7 Hz, —O—CH$_2$—), 4.36 (2H, ABq, 3—CH$_2$), 5.06 (1H, d, J=5 Hz, C$_6$—H), 5.66 (1H, q, J=5×8 Hz, C$_7$—H), 7.25 (1H, d, J=8 Hz, —OCONH—), 8.79 (1H, d, J=8 Hz, —CONH—).

EXAMPLE 46

(1) In 20 ml of methylene chloride were dissolved 3.53 g of 7β-(D-5-carboxy-5-phthalimidovaleramido)-3-hydroxymethyl-3-cephem-4-carboxylic acid ditriethylamine salt and 0.87 g of 5-mercapto-1-methyl-1H-tetrazole. To this solution was added dropwise a solution of 1.50 g of ethyl o-phenylene phosphate in 3.8 ml of methylene chloride under stirring and cooling at −25° C. to −20° C. and the mixture was stirred for 1 hour at −5° C. to 0° C. To the reaction mixture were added 50 ml of water, 20 ml of THF and 20 ml of methylene chloride and the mixture was adjusted to pH2 with 4N-hydrochloric acid. After phase separation, the aqueous layer was extracted with a mixture of 20 ml of methylene chloride and 10 ml of THF. The organic layer and the extract were combined, washed with 20 ml of water, dried with anhydrous magnecium sulfate, concentrated under reduced pressure and the residue was dissolved in 20 ml of acetone. The solution was added dropwise into 300 ml of ether and the resultant precipitate was collected by filtration, washed with ether and dried in vacuo to give 2.86 g (yield 95.1%) of 7β-(D-5-carboxy-5-phthalimidovaleramido)-3-(1-methyl-1H-tetrazol-5-yl)thiomethyl-3-cephem-4-carboxylic acid. The IR and NMR spectra of this product were identical with those of the compound obtained in Example 1.

(2) In the above (1), methylene chloride solution of ethyl o-phenylene phosphate was added dropwise at 23°–27° C. and the mixture was stirred for about 39° C. for 5 minutes, cooled to 0° C. and treated thereafter in the same method as described in the above (1) to give 2.72 (yield 90.4%) of a white powder. IR spectrum of this product was identical with that of the compound obtained in the above (1).

EXAMPLE 47

(1) To the mixture of 1.10 g of pyrogallol and 1.30 g of methyl phosphorodichloridate was added 8 ml of methylene chloride. To the mixture was added dropwise 1.86 g of triethylamine under stirring and cooling at −35° C. to −30° C., followed by stirring at 0°–5° C. for 2 hours to afford the reaction mixture containing 4-hydroxy-2-methoxy-2-oxo-1,3,2-benzodioxaphosphole.

(2) In 20 ml of methylene chloride were dissolved 3.53 g of 7β-(D-5-carboxy-5-phthalimidovaleramido)-3-hydroxymethyl-3-cephem-4-carboxylic acid ditriethylamine salt and 0.87 g of 5-mercapto-1-methyl-1H-tetrazole. The whole reaction mixture obtained in (1) was added to the solution under stirring and cooling at −25° C. to −20° C., and the reaction mixture adhering to the reaction vessel was washed with 6 ml of methylene chloride and the washing was added. The resulting suspension was stirred for 1 hour at −5°–0° C. and the reaction mixture was treated in the same method as in Example 46-(1) to give 2.76 g (91.8%) of 7β-(D-5-carboxy-5-phthalimidovaleramido)-3-(1-methyl-1H-tetrazol-5-yl) thiomethyl-3-cephem-4-carboxylic acid. This product was identified by IR spectrum.

(3) Using the reaction mixture of 5-ethoxycarbonyl-2-methoxy-2-oxo-1,3,2-benzodioxaphosphole obtained by the same procedure as (1) except using 1.59 g of ethyl 3,4-dihydroxybenzoate in place of of pyrogallol, the same procedure as (2) was performed to give 2.85 g (yield 94.7%) of the same product as obtained in (2). This product was identified by IR spectrum.

(4) Using the reaction mixture of 2-methoxy-5-methyl-2-oxo-1,3,2-benzodioxaphosphole obtained by the same procedure as (1) except using 1.09 g of 3,4-dihydroxytoluene in place of pyrogallol, the same procedure as (2) was repeated to give 2.83 g (yield 94.1%) of the product. IR spectrum of this product was identical with that of the compound obtained in (2).

EXAMPLE 48

To the mixture of 87 mg of 5-mercapto-1-methyl-1H-tetrazole and 216 mg of sodium 7β-[2-(2-aminothiazol-4-yl)-2-(syn)-methoxyiminoacetamido]-3-hydroxymethyl-3-cephem-4-carboxylate were added 1 ml of formamide and 1 ml of acetonitrile and the mixture was stirred to obtain a clear solution. To this solution was added a solution of 280 mg of methyl o-phenylene phosphate in 0.75 ml of methylene chloride under stirring and cooling with ice bath and the mixture was stirred for 0.5 hour under cooling with ice bath. After addition of 1 ml of cold water, the reaction mixture was concentrated under reduced pressure. To the residual solution was added 2 ml of water and the pH of the solution was adjusted to 2.5. The resulting precipitate was collected by filtration, washed with 1 ml of cold water and dried in vacuo to give 210 mg (yield 82.6%) of 7β-[2-(2-aminothiazol-4-yl)-2-(syn)-methoxyiminoacetamido]-3-(1-methyl-1H-tetrazol-5-yl)thiomethyl-3-cephem-4-carboxylic acid.

NMR (DMSO-d6)δ: 3.67 (2H, br, 2—CH2) 3.83, 3.93 (6H, two singlets, N—CH3, O—CH3), 4.27 (2H, br, 3—CH2), 5.09 (1H, d, J=5 Hz, C6—H), 5.76 (1H, q, J=5×8 Hz, C7—H), 6.73

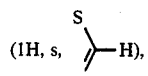

(1H, s,  >—H), 9.55 (1H, d, J=8 Hz, CONH).

EXAMPLE 49

To the mixture of 230 mg of 7β-amino-3-hydroxymethyl-3-cephem-4-carboxylic acid, 174 mg of 5-mercapto-1-methyl-1H-tetrazole, 4 ml of formamide and 1 ml of acetonitrile was added 253 mg of triethylamine under stirring and cooling with ice bath. To the resulting solution were added a solution of 650 mg of methyl o-phenylene phosphate in 2 ml of methylene chloride and 5 ml of acetonitrile under stirring and cooling at −10° C. to 0° C., followed by stirring for 0.5 hour at 0° C. to 5° C. The resulting precipitate was collected by filtration, washed with 5 ml of acetonitrile and suspended in a mixed solution of 6 ml of water and 2 ml of acetonitrile. To this suspension was added about 0.1 ml of 35% hydrochloric acid to obtain a clear solution. After adjusting the pH of the solution to 4 by addition of 25% ammonia-water under cooling with ice bath, the resulting crystals were collected by filtration, washed with 2 ml of cold water and dried in vacuo to give 280 mg (yield 85.3%) of 7β-amino-3-(1-methyl-1H-tetrazol-5-yl)thiomethyl-3-cephem-4-carboxylic acid.

IR (KBr) cm$^{-1}$: 1790, 1615, 1535, 1410.

NMR (D2O+CF3COOD)δ: 3.71 (2H, s, 2—CH2), 3.96 (3H, s, N—CH3), 4.22 (2H, s, 3—CH2), 5.06 (1H, d, J=5 Hz, C6—H), 5.17 (1H, d, J=5 Hz, C7—H).

EXAMPLE 50

To the mixture of 0.954 g of 7β-(D-5-carboxy-5-benzamidovaleramido)-3-hydroxymethyl-3-cephem-4-carboxylic acid and 0.244 g of 1-methyl pyrrole were added 2 ml of formamide and 4 ml of acetonitrile. To the resulting solution was added a solution of 0.744 g of methyl o-phenylene phosphate in 2 ml of methylene chloride under stirring and cooling at −5°-0° C. and the mixture was stirred for 0.5 hour at −5°-0° C. To the reaction mixture were added 24 ml of methylene chloride, 12 ml of THF and 20 ml of water and the pH was adjusted to 2 by 4N-hydrochloric acid. After phase separation, the aqueous layer was extracted with 15 ml of methylene chloride-THF (2:1). The organic layer and the extract were combined and treated by the similar method as described in example 46-(1) to give 0.944 g (yield 87.3%) of 7β-(D-5-carboxy-5-benzamidovaleramido)-3-(1-methylpyrrol-2-yl)methyl-3-cephem-4-carboxylic acid.

IR (KBr) cm$^{-1}$: 1770, 1725, 1645, 1530.

NMR (D$_2$O+NaHCO$_3$)δ: 1.5-2.7 (6H, m, —(CH$_2$)$_3$—), 2,80, 3.16 (2H, ABq, J=18 Hz, 2—CH$_2$), 3.44, 3.90 (2H, ABq, J=14 Hz, 3—CH$_2$), 3.46 (3H, s, N—CH$_3$), 4.42 (1H, m, >CH—), 4.96 (1H, d, J=5 Hz, C$_6$—H), 5.33 (1H, d, J=5 Hz, C$_7$—H), 5.8-6.2, 6.6-6.8

(3H, m, 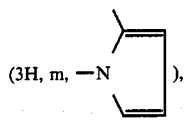), 7.2-8.0

(5H, m, 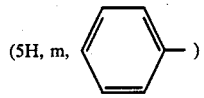)

EXAMPLE 51

(1) To the mixture of 0.430 g of 2-methyl-5-oxo-3-thioxo-2,3,4,5-tetrahydro-as-triazine, 4 ml of formamide and 4 ml of acetonitrile was added 0.416 ml of triethylamine. To the resulting solution was added 1.16 g of dipotassium salt of 7β-(D-5-carboxy-5-phthalimidovaleramido)-3-hydroxymethyl-3-cephem-4-carboxylic acid. To the mixture was added a solution of 1.12 g of methyl o-phenylenephosphate in 3 ml of methylene chloride under stirring and cooling at −20° C. to −15° C. followed by stirring for 0.5 hour at 0°-5° C. The reaction mixture was concentrated under reduced pressure and 80 ml of cold water was added to the residual solution. The resulting precipitate was collected by filtration, washed with 10 ml of cold water and dried in vacuo to give 1.14 g (yield 90.7%) of 7β-(D-5-carboxy-5-phtalimidovaleramido)-3-(2,5-dihydro-2-methyl-5-oxo-as-triazin-3-yl)thiomethyl-3-cephem-4-carboxylic acid.

IR (KBr) cm$^{-1}$: 1775, 1715, 1645.

NMR (D$_2$O+NaOD)δ: 1.8-2.6 (6H, m, —(CH$_2$)$_3$—), 3.04, 3.60 (2H, ABq, J=18 Hz, 2—CH$_2$), 3.86 (3H, s, N—CH$_3$), 4.02, 4.39 (2H, ABq, J=13 Hz, 3—CH$_2$), 4.99 (1H, d, J=5 Hz, C$_6$—H), 5,55 (1H, d, J=5 Hz, C$_7$—H), 7.75 (1H, s, triazin-H), 7.80

(4H, s, 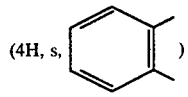)

(2) Using 0.384 g of 2-thiouracil in place of triazine the same procedure as in (1) afforded 1.10 g (yield 89.6%) of 7β-(D-5-carboxy-5-phthalimidovaleramido)-3-(4-hydroxypyrimidin-2-yl)thiomethyl-3-cephem-4-carboxylic acid.

IR (KBr) cm$^{-1}$: 1770, 1710, 1530.

NMR (D$_2$O+NaOD)δ: 1.3-2.6 (6H, m, —(CH$_2$)$_3$—), 3.02, 3.50 (2H, ABq, J=18 Hz, 2—CH$_2$), 3.97, 4.33 (2H, ABq, J=13 Hz, 3—CH$_2$), 5.01 (1H, d, J=5 Hz, C$_6$—H), 5.54 (1H, d, J=5 Hz, C$_7$—H), 6.23, 7.84

(2H, dd, J = 7Hz, 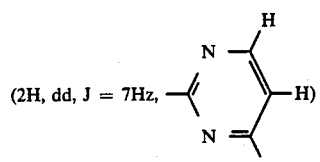)

7.82

(4H, s, 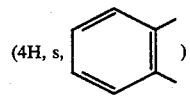)

EXAMPLE 52

To the mixture of 0.195 g of 2-mercaptobenzimidazole and 0.580 g of dipotassium salt of 7β-(D-5-carboxy-5-phthalimidovaleramido)-3-hydroxymethyl-3-cephem-4-carboxylic acid were added 2 ml of formamide and 2 ml of acetonitrile. To the resulting solution was added a solution of 0.558 g of methyl O-phenylene phosphate in 1.5 ml of methylene chloride was added under stirring and cooling at −10° C. to −5° C., followed by stirring at 0°-5° C. for 1 hour. The reaction mixture was treated in a similar manner as described in Example 51-(1) to give 0.560 g (yield 88.1%) of 7β-(D-5-carboxy-5-phthalimidovaleramido)-3-(benzimidazol-2-yl)-thiomethyl-3-cephem-4-carboxylic acid.

IR (KBr) cm$^{-1}$: 1785, 1770, 1710, 1640, 1390.

NMR (D$_2$O-NaHCO$_3$)δ: 1.3-2.6 (6H, m, —(CH$_2$)$_3$—), 2.96 3.23 (2H, ABq, J=18 Hz, 2—CH$_2$), 3.84, 4.40 (2H, ABq, J=13 Hz, 3—CH$_2$). 4.57 (1H, m, >CH—), 4.92 (1H, d, J=5 Hz, C$_6$—H), 5.52 (1H, d, J=5 Hz, C$_7$—H), 6.9-7.8

(8H, m, 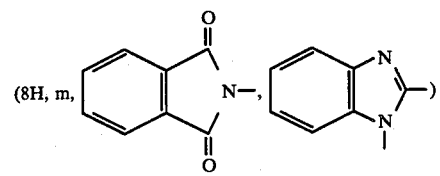)

EXAMPLE 53

(1) To the mixture of 1.637 g of 7β-(D-5-carboxy-5-phthalimidovaleramido)-3-hydroxymethyl-3-cephem-4-carboxylic acid ditriethylamine salt and 0.53 g of 2-mercaptobenzoic acid were added 14 ml of methylene chloride and 7 ml of THF. To the resulting solution was added a solution of 0.863 g of methyl o-phenylene phosphate in 2.3 ml of methylene chloride under stirring and cooling at −20° C. to −15° C., followed by stirring at 0°-5° C. for 0.5 hour. The reaction mixture was treated in a similar method to Example 46-(1) to give 1.36 g (yield 91.7%) of 7β-(D-5-carboxy-5-phthalimidovaleramido)-3-(2-carboxyphenyl)thiomethyl-3-cephem-4-carboxylic acid.

IR (KBr) cm⁻¹: 1770, 1710, 1535, 1465, 1390.

NMR (DMSO-d₆)δ: 1.2–2.4 (6H, m, —(CH₂)₃—), 3.55 (2H, br, 2—CH₂), 4.06 (2H, br, 3—CH₂), 4.75 (1H, t, J=7 Hz, >CH—), 5.06 (1H, d, J=5 Hz, C₆—H), 5.61 (1H, q, J=5 & 8 Hz, C₇—H), 7.0–7.7

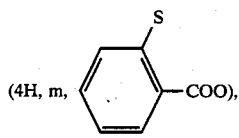

(4H, m, [structure with S and COO]), 7.89

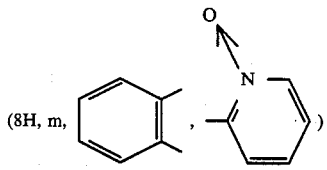

(4H, m, [phthalimide structure N—]), 8.79 (1H, d, J=8 Hz, CONH).

(2) Using 0.443 g of 2-mercaptopyridine N-oxide in place of 2-mercaptobenzoic acid, the same reaction as (1) was performed. The reaction mixture was concentrated under reduced pressure and the residual mixture was dissolved in 50 ml of water-acetonitrile (1:1). After evaporating acetonitrile, the resulting precipitate was collected by filtration, washed with 10 ml of cold water and dried in vacuo to give 1.31 g (yield 92.3%) of 7β-(D-5-carboxy-5-phthalimidovaleramido)-3-(N-oxidopyridin-2-yl)thiomethyl-3-cephem-4-carboxylic acid.

IR (KBr) cm⁻¹: 1775, 1715, 1530, 1470, 1390.

NMR (D₂O+NaOD)δ: 1.3–2.6 (6H, m, —(CH₂)₃—), 2.99, 3.53 (2H, ABq, J=18 Hz, 2—CH₂), 3.90, 4.25 (2H, ABq, J=14 Hz, 3—CH₂), 4.95 (1H, d, J=5 Hz, C₆—H), 5.53 (1H, d, J=5 Hz, C₇—H), 7.1–8.5

(8H, m, [two ring structures with N-oxide])

EXAMPLE 54

To 0.288 g of 1-carboxymethyl-5-mercapto-1H-tetrazole and 0.363 g of triethylamine was added 6 ml of methylene chloride. To the resulting solution was added 0.847 g of 7β-(D-5-carboxy-5-phthalimidovaleramido)-3-hydroxymethyl-3-cephem-4-carboxylic acid ditriethylamine salt. To the mixture was added a solution of 0.450 mg of methyl O-phenylene phosphate in 1.2 ml of methylene chloride under stirring and cooling at −20° C. to −15° C. The mixture was stirred at −5° C. to 0° C. for 1 hour and the reaction solution was treated in a similar method to Example 46-(1) to give 0.711 g (yield 91.8%) of 7β-(D-5-carboxy-5-phthalimidovaleramido)-3-(1-carboxymethyl-1H-tetrazol-5-yl)thiomethyl-3-cephem-4-carboxylic acid.

IR (KBr) cm⁻¹: 1770, 1710, 1530.

NMR (DMSO-d₆)δ: 1.3–2.4 (6H, m, —(CH₂)₃), 3.62 (2H, br, 2—CH₂), 4.17, 4.47 (2H, ABq, J=14 Hz, 3—CH₂), 4.71 (1H, t, J=6 Hz, >CH—), 4.99 (1H, d, J=5 Hz, C₆—H), 5.28 (2H, s, NCH₂COO), 5.62 (1H, q, J=5 & 8 Hz, C₇—H), 7.89

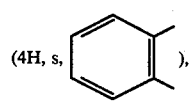

(4H, s, ), 8.77 (1H, d, J=8 Hz, CONH)

EXAMPLE 55

(1) To the solution of 0.975 g 7β-(D-5-carboxy-5-phthalimidovaleramido)-3-hydroxymethyl-3-cephem-4-carboxylic acid ditriethylamine salt and 0.172 g of ethanethiol in 10 ml of methylene chloride was added a solution of 0.514 g of methyl O-phenylene phosphate in 1.39 ml of methylene chloride under stirring and cooling at −20° C. to −15° C., followed by stirring for 1 hour at 0°-5° C. To the reaction mixture were added 20 ml of water and 20 ml of THF and the pH was adjusted to 2 by 35% aqueous hydrochloric acid. To the mixture was added 30 ml of methylene chloride. After phase separation, aqueous phase was extracted with 15 ml of methylene chloride-THF(2:1, v/v). The organic layer and the extract were combined, washed with two 10 ml portions of water and 10 ml of water was added. The pH of the mixture was adjusted to 7. After phase separation, organic layer was extracted with 5 ml of water. The water phase and extract were combined and concentrated under reduced pressure. The concentrated solution was subjected to Amberlite XAD-2 column chromatography (XAD-2 of 100–200 mesh,: 70 ml, column height: 40 cm) and eluted with water and then with water-acetone (20:1, v/v). The fractions were checked by TLC (developing solvent: acetonitrile 40: water 2: 99% formic acid 0.1) and the fractions (Rf: about 0.16) containing the desired product were combined, concentrated under reduced pressure and lyophilized to give 0.515 g (yield 63.0%) of 7β-(D-5-carboxy-5-phthalimidovaleramido)-3-ethylthiomethyl-3-cephem-4-carboxylic acid disodium salt.

IR (KBr) Cm⁻¹: 1760, 1710, 1610, 1390.

NMR (D₂O)δ: 1.18 (3H, t, CH₃), 1.4–2.7 (8H, m, —(CH₂)₃—, —CH₂CH₃), 2.93, 3.55 (2H, ABq, J=18 Hz, 2—CH₂), 3.23, 3.81 (2H, ABq, J=14 Hz, 3—CH₂), 4.98 (1H, d, J=5 Hz, C₆—H), 5.48 (1H, d, J=5 Hz, C₇—H), 7.88

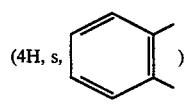

(4H, s, )

(2) To the mixture of 0.580 g of 7β-(D-5-carboxy-5-phthalimidovaleramido)-3-hydroxymethyl-3-cephem-4-carboxylic acid dipotassium salt and 0.165 g of thiophenol were added 2 ml of formamide and 2 ml of acetonitrile. To the resultant solution was added a solution of 0.558 g of methyl O-phenylene phosphate in 1.5 ml of methylene chloride under stirring and cooling at −30° C. to −20° C., followed by stirring for 45 minutes at 0°-5° C. The reaction mixture was concentrated under reduced pressure and 40 ml of cold water was added to the cocentrate. The resultant precipitate was collected by filtration, washed with 10 ml of cold water and dissolved in 20 ml of 50% aqueous acetonitrile. The solution was adjusted to pH 7 and concentrated under reduced pressure to remove acetonitrile. The concentrate was subjected to XAD-2 column chromatography (Rf of the desired product: about 0.36) in the same method as in above (1) to give 0.397 g (yield 62.1%) of 7β-(D-5-carboxy-5-phthalimidovaleramido)-3-phenylthiomethyl-3-cephem-4-carboxylic acid disodium salt.

IR (KBr) cm$^{-1}$: 1765, 1710, 1605, 1390.

NMR (DMSO-d$_6$)δ: 1.2–2.5 (6H, m, —(CH$_2$)$_3$—), 3.11, 3.49 (2H, ABq, J=18 Hz, 2—CH$_2$), 4.36 (1H, m, >CH—), 4.81 (1H, d, J=5 Hz, C$_6$—H), 5.42 (1H, d, J=5 Hz, C$_7$—H), 7.34

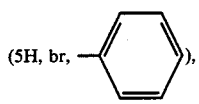

7.84

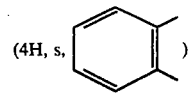

EXAMPLE 56

In 25 ml of methylene chloride were dissolved 3.53 g of 7β-(D-5-carboxy-5-phthalimidovaleramido)-3-hydroxymethyl-3-cephem-4-carboxylic acid ditriethylamine salt and 0.76 g of triethylamine. To this solution were added dropwise a solution of 2.79 g of methyl o-phenylene phosphate in 7.5 ml of methylene chloride under cooling at −45° C. to −40° C. with stirring and the mixture was stirred for 30 minutes at the same temperature. To this reaction mixture was added 50 ml of ether and the mixture was allowed to stand at 20° C. to 25° C. for 20 minutes. The resultant powderly precipitate was collected by filtration and washed with ether and dried. The resulting powder was dissolved in a mixture of 10 ml of water and 20 ml of acetonitrile and the mixture was adjusted to pH 7.0 with 1N-NaOH and acetonitrile was distilled off under reduced pressure. The concentrate was subjected to Amberlite XAD-2 column chromatography (XAD-2 of 100–200 mesh: 150 ml, column hight: 45 cm), elution being carried out with water. The eluate was checked by TLC (developing solvent: acetonitrile 80: water 15: 99% formic acid 2) and the fractions (Rf: about 0.12) containing the desired product were collected. The resultant solution was concentrated, adjusted to pH 6.0 with 1N NaOH and lyophilized to give 2.76 g (yield 90.7%) of sodium 7β-(D-5-carboxylato-5-phthalimidovaleramido)-3-cephem-3-triethylammoniomethyl-4-carboxylate.

IR(KBr) cm$^{-1}$: 3450, 1775, 1710, 1612, 1465.

NMR (D$_2$O)δ: 1.34 (9H, t, J=7 Hz, (—CH$_3$)×3), 1.30–2.60 (6H, m, —(CH$_2$)$_3$—), 3.28 (6H, q, J=7 Hz, —N(CH$_2$)$_3$), 3.38 & 4.08 (2H, ABq, J=18 Hz, 2—CH$_2$), 5.13 (1H, d, J=5 Hz, C$_6$—H), 5.61 (1H, d, J=5 Hz, C$_7$—H), 7.88

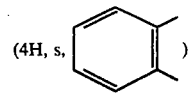

EXAMPLE 57

In 25 ml of methylene chloride were dissolved 3.53 g of 7β-(D-5-carboxy-5-phthalimidovaleramido)-3-hydroxymethyl-3-cephem-4-carboxylic acid ditriethylamine salt and 1.33 g of 1-(2-dimethylaminoethyl)-1H-tetrazole and 0.76 g of triethylamine. To this solution were added dropwise a solution of 2.79 g of methyl o-phenylene phosphate in 7.5 ml of methylene chloride under cooling at −45° C. to −40° C. with stirring and the mixture was stirred for 30 minutes at the same temperature. And then, the mixture was allowed to stand at 20° C. to 25° C. for 20 minutes. The resultant powdery precipitate was collected by filtration and washed with methylene chloride and dried in vacuo.

The above product (Rf; about 0.17) was further treated as in Example 56 to give 2.67 g (yield 82.3%) of sodium 7β-(D-5-carboxylato-5-phthalimidovaleramido)-3-cephem-3-[dimethyl[2-(1,2,3,4-tetrazol-1-yl]ethylammonio]methyl-4-carboxylate.

IR(KBr) cm$^{-1}$: 3450, 1770, 1710, 1613, 1390.

NMR(D$_2$O) δ: 1.30–2.60 (6H, m, —(CH$_2$)$_3$—), 3.00–4.30

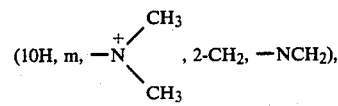

4.90–5.40 (3H, m, —NCH$_2$, C$_6$—H), 5.53 (1H, d, J=5 Hz, C$_7$—H), 7.82

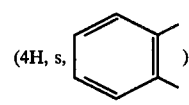

9.37

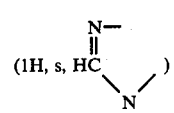

EXAMPLE 58

In 4 ml of formamide and 8 ml of acetonitrile were dissolved 1.20 g of dipotassium 7β-(D-5-carboxylato-5-phthalimidovaleramido)-3-hydroxymethyl-3-cephem-4-carboxylate monohydrate and 312 mg of 4-cyanopyridine. To this solution were added dropwise a solution of 1.12 g of methyl o-phenylene phosphate in 3 ml of methylene chloride under cooling at 0°-5° C. and stirring, and the mixture was stirred for 30 minutes at the same temperature. To this reaction mixture was added 3.5 ml of 1N NaOH and methylene chloride and acetonitrile were distilled off under reduced pressure. The concentrate was subjected to silica gel columnchromatography (50 g of silica gel was packed into a column with acetonitrile-water-formic acid (80:15:2), column height: 38 cm), elution being carried out with acetonitrile-water (2.5:1). The eluate was checked by TLC (developing solvent: acetonitrile 80: water 15:99% formic acid 2) and the fractions (Rf: about 0.22) containing the desired product were collected. The resultant solution was concentrated, adjusted to pH 6.0 with 1N NaOH and lyophilized to give 1.08 g (yield 88.3%) of sodium 7β-(D-5-carboxylato-5-phthalimidovaleramido)-3-cephem-3-(4-cyanopyridinium)methyl-4-carboxylate.

IR(KBr) cm$^{-1}$: 3420, 1770, 1710, 1613, 1395.

NMR(D$_2$O)δ: 1.40-2.70 (6H, m, —(CH$_2$)$_3$—), 3.04 & 3.68 (2H, ABq, J=18 Hz, 2—CH$_2$), 5.13 (1H, d, J=5 Hz, C$_6$—H), 5.44 & 5.70 (2H, ABq, J=15 Hz, 3—CH$_2$), 5.63 (1H, d, J=5 Hz, C$_7$—H), 7.82

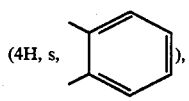

(4H, s,                ), 8.57 & 9.36

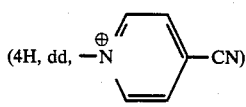

(4H, dd, —N⊕         —CN)

EXAMPLE 59

In 4 ml of formamide and 8 ml of acetonitrile were dissolved 1.20 g of dipotassium 7β-(D-5-carboxylato-5-phthalimidovaleramido)-3-hydroxymethyl-3-cephem-4-carboxylate monohydrate and 411 mg of methyl nicotinate. To this solution were added dropwise a solution of 1.49 g of methyl o-phenylene phosphate in 4 ml of methylene chloride under cooling at −10° C. to −5° C. with stirring and the mixture was stirred for 30 minutes at the same temperature. The above reaction mixture (Rf: about 0.23) was further treated as in Example 58 to give 1.18 g (yield 91.5%) of sodium 7β-(D-5-carboxylato-5-phthalimidovaleramido)-3-cephem-3-(3-methoxycarbonylpyridinium)methyl-4-carboxylate.

IR (KBr) cm$^{-1}$: 3445, 1770, 1708, 1613, 1395.

NMR (D$_2$O)δ: 1.30-2.60 (6H, m, —(CH$_2$)$_3$—), 2.95 & 3.62 (2H, ABq, J=18 Hz, 2—CH$_2$), 5.12 (1H, d, J=5 Hz, C$_6$, —H), 5.36 & 5.72 (2H, ABq, J=15 Hz, 3—CH$_2$), 5.62 (1H, d, J=5 Hz, C$_7$—H), 7.79

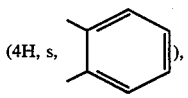

(4H, s,                ), 8.0-9.8

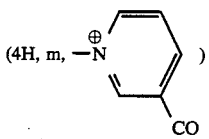

(4H, m, —N⊕         )
                    CO

What we claim is:

1. A method of producing a 1,3,2,-dioxaphosphole of the formula

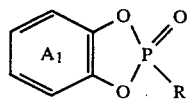

wherein

represents a benzene ring which may be substituted and R represents an aryl, alkoxy or aralkyloxy group which may be substituted, which comprises reacting a catechol compound of the formula

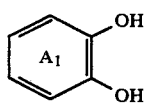

wherein

is as defined above, with a compound of the formula

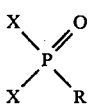

wherein X is a halogen atom and R is as defined above, at a temperature not higher than about 30° C. in the presence of a base.

2. A method according to claim 1, wherein

represents an unsubstituted benzene ring.

3. A method according to claim 1, wherein the 1,3,2-dioxaphosphole compound is ethyl o-phenylene phosphate.

4. A method according to claim 1, wherein R represents an alkoxy group having one to six carbon atoms.

5. A method according to claim 1, wherein X represents a chlorine atom.

6. A method according to claim 1, wherein the base represents a trialkylamine in which alkyl has one to six carbon atoms.

7. A method according to claim 1, wherein the reaction is carried out in an inert solvent.

8. A method according to claim 1, wherein the reaction is carried out at a temperature within the range of 30° C. to −100° C.

9. A method according to claim 7, wherein the reaction is carried out at a temperature within the range of 30° C. to −100° C.

10. The process of claim 1, wherein R is alkoxy or aralkyloxy.

* * * * *